(12) United States Patent
Murillo et al.

(10) Patent No.: US 10,524,779 B2
(45) Date of Patent: Jan. 7, 2020

(54) AUTOMATICALLY RELOADING SUTURE PASSER DEVICES AND METHODS

(71) Applicant: Ceterix Orthopaedics, Inc., Fremont, CA (US)

(72) Inventors: Michael Murillo, Menlo Park, CA (US); Michael J. Hendricksen, Redwood City, CA (US); Yoav Ben-Haim, San Francisco, CA (US)

(73) Assignee: Ceterix Orthopaedics, Inc., Fremont, CA (US)

( * ) Notice: Subject to any disclaimer, the term of this patent is extended or adjusted under 35 U.S.C. 154(b) by 245 days.

(21) Appl. No.: 15/289,054

(22) Filed: Oct. 7, 2016

(65) Prior Publication Data

US 2017/0027558 A1 Feb. 2, 2017

Related U.S. Application Data

(60) Division of application No. 14/572,485, filed on Dec. 16, 2014, now Pat. No. 9,492,162, which is a (Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0482* (2013.01); *A61B 17/0483* (2013.01); *A61B 17/062* (2013.01); *A61B 17/0485* (2013.01); *A61B 17/06066* (2013.01); *A61B 2017/0046* (2013.01); *A61B 2017/0053* (2013.01); (Continued)

(58) Field of Classification Search
CPC ...... A61B 17/04; A61B 17/0469–0491; A61B 2017/047–049; A61B 2017/0496
See application file for complete search history.

(56) References Cited

U.S. PATENT DOCUMENTS

| | | | |
|---|---|---|---|
| 1,037,864 | A | 9/1912 | Carlson et al. |
| 2,738,790 | A | 3/1956 | Todt, Sr. et al. |

(Continued)

FOREIGN PATENT DOCUMENTS

| | | |
|---|---|---|
| CN | 201263696 Y | 7/2009 |
| CN | 101961256 A | 2/2011 |

(Continued)

OTHER PUBLICATIONS

Ceterix; Novocut suture manager; retrieved from the internet (https://web.archive.org/web/20150314071511/http://www.ceterix.com:80/im-a-physician/products/) on Oct. 11, 2017; 1 page; Mar. 12, 2015.
(Continued)

*Primary Examiner* — Jonathan A Hollm
(74) *Attorney, Agent, or Firm* — Norman F. Hainer, Jr.

(57) ABSTRACT

Suture passers and methods of use. Described herein are suture passers preloaded with suture, including cartridges that couple to a suture passer to form a loaded suture passer; the suture passer may be operated to pass one or more lengths of suture without having to be manually reloaded. In particular, described herein are preloaded and automatically reloading apparatuses typically.

15 Claims, 73 Drawing Sheets

Related U.S. Application Data continuation-in-part of application No. PCT/US2014/030137, filed on Mar. 17, 2014.

(60) Provisional application No. 61/916,735, filed on Dec. 16, 2013.

(51) Int. Cl.
A61B 17/06 (2006.01)
A61B 17/00 (2006.01)
A61B 17/29 (2006.01)
A61B 90/00 (2016.01)

(52) U.S. Cl.
CPC ............... A61B 2017/00115 (2013.01); A61B 2017/0472 (2013.01); A61B 2017/0477 (2013.01); A61B 2017/06042 (2013.01); A61B 2017/06047 (2013.01); A61B 2017/06095 (2013.01); A61B 2017/2933 (2013.01); A61B 2090/0811 (2016.02)

(56) References Cited

U.S. PATENT DOCUMENTS

| | | |
|---|---|---|
| 2,748,773 A | 6/1956 | Vacheresse, Jr. |
| 3,470,875 A | 10/1969 | Johnson |
| 3,580,256 A | 5/1971 | Wilkinson et al. |
| 3,807,407 A | 4/1974 | Schweizer |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,553,543 A | 11/1985 | Amarasinghe |
| 4,605,002 A | 8/1986 | Rebuffat |
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,059,206 A | 10/1991 | Winters |
| 5,112,344 A | 5/1992 | Petros |
| 5,129,912 A | 7/1992 | Noda et al. |
| 5,139,520 A | 8/1992 | Rosenberg |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,320,633 A | 6/1994 | Allen et al. |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,383,877 A | 1/1995 | Clarke |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,431,669 A | 7/1995 | Thompson et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,756 A | 4/1996 | Hasson |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,748 A | 5/1997 | Beck et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,797,958 A | 8/1998 | Yoon |
| 5,800,445 A | 9/1998 | Ratcliff et al. |
| 5,814,054 A | 9/1998 | Kortenbach et al. |
| 5,814,069 A | 9/1998 | Schulze et al. |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,910,148 A | 6/1999 | Reimels et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 5,997,554 A | 12/1999 | Thompson |
| 6,039,753 A | 3/2000 | Meislin |
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |

(56) References Cited

U.S. PATENT DOCUMENTS

| | | |
|---|---|---|
| 6,099,568 A | 8/2000 | Simonian et al. |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |
| 6,159,224 A | 12/2000 | Yoon |
| 6,190,396 B1 | 2/2001 | Whitin et al. |
| 6,221,085 B1 | 4/2001 | Djurovic |
| 6,231,606 B1 | 5/2001 | Graf et al. |
| 6,238,414 B1 | 5/2001 | Griffiths |
| 6,264,694 B1 | 7/2001 | Weiler |
| 6,277,132 B1 | 8/2001 | Brhel |
| 6,322,570 B1 | 11/2001 | Matsutani et al. |
| 6,325,808 B1 | 12/2001 | Bernard et al. |
| 6,355,050 B1 | 3/2002 | Andreas et al. |
| 6,368,334 B1 | 4/2002 | Sauer |
| 6,368,343 B1 | 4/2002 | Bonutti et al. |
| 6,443,963 B1 | 9/2002 | Baldwin et al. |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,833,005 B1 | 12/2004 | Mantas |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,972,027 B2 | 12/2005 | Fallin et al. |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,153,312 B1 | 12/2006 | Torrie et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,481,826 B2 | 1/2009 | Cichocki |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,717,927 B2 | 5/2010 | Hahn et al. |
| 7,722,630 B1 | 5/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,972,344 B2 | 7/2011 | Murray et al. |
| 8,298,230 B2 | 10/2012 | Sutter et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 8,465,505 B2 | 6/2013 | Murillo et al. |
| 8,500,809 B2 | 8/2013 | Saliman |
| 8,562,631 B2 | 10/2013 | Saliman |
| 8,632,563 B2 | 1/2014 | Nagase et al. |
| 8,647,354 B2 | 2/2014 | Domingo |
| 8,663,253 B2 | 3/2014 | Saliman |
| 8,702,731 B2 | 4/2014 | Saliman |
| 8,808,299 B2 | 8/2014 | Saliman et al. |
| 8,821,518 B2 | 9/2014 | Saliman |
| 8,888,848 B2 | 11/2014 | Saliman et al. |
| 8,911,456 B2 | 12/2014 | McCutcheon et al. |
| 8,920,441 B2 | 12/2014 | Saliman et al. |
| 9,011,454 B2 | 4/2015 | Hendrickson et al. |
| 9,211,119 B2 | 12/2015 | Hendrickson et al. |
| 9,247,934 B2 | 2/2016 | Murillo et al. |
| 9,247,935 B2 | 2/2016 | George et al. |
| 9,314,234 B2 | 4/2016 | Hirotsuka et al. |
| 9,332,980 B2 | 5/2016 | George et al. |
| 9,492,162 B2 | 11/2016 | Murillo et al. |
| 2001/0041938 A1 | 11/2001 | Hein |
| 2002/0169477 A1 | 11/2002 | Demopulos et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0078617 A1 | 4/2003 | Schwartz et al. |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0117014 A1 | 6/2004 | Bryant |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0043746 A1 | 2/2005 | Pollak et al. |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0178680 A1 | 8/2006 | Beverly et al. |
| 2006/0282098 A1 | 12/2006 | Shelton et al. |
| 2007/0032799 A1 | 2/2007 | Pantages et al. |
| 2007/0038230 A1 | 2/2007 | Stone et al. |
| 2007/0156174 A1 | 7/2007 | Kaiser et al. |
| 2007/0185532 A1 | 8/2007 | Stone et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2007/0270885 A1* | 11/2007 | Weinert ............ A61B 17/0469 606/139 |
| 2008/0086147 A1 | 4/2008 | Knapp |
| 2008/0091219 A1 | 4/2008 | Marshall et al. |
| 2008/0097482 A1 | 4/2008 | Bain et al. |
| 2008/0097489 A1 | 4/2008 | Goldfarb et al. |
| 2008/0140091 A1 | 6/2008 | DeDeyne et al. |
| 2008/0140094 A1 | 6/2008 | Schwartz et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0275553 A1 | 11/2008 | Wolf et al. |
| 2008/0294256 A1 | 11/2008 | Hagan et al. |
| 2009/0012520 A1 | 1/2009 | Hixson et al. |

(56) References Cited

U.S. PATENT DOCUMENTS

| | | |
|---|---|---|
| 2009/0012538 A1 | 1/2009 | Saliman |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0112232 A1 | 4/2009 | Crainich et al. |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2011/0022061 A1 | 1/2011 | Orphanos et al. |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0071563 A1 | 3/2011 | Magliani |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0251626 A1 | 10/2011 | Wyman et al. |
| 2011/0270306 A1 | 11/2011 | Denham et al. |
| 2012/0101524 A1 | 4/2012 | Bennett |
| 2012/0283750 A1 | 11/2012 | Saliman et al. |
| 2012/0283753 A1 | 11/2012 | Saliman et al. |
| 2012/0303046 A1 | 11/2012 | Stone et al. |
| 2013/0072948 A1 | 3/2013 | States, III et al. |
| 2013/0085512 A1 | 4/2013 | Wyman et al. |
| 2013/0253536 A1 | 9/2013 | Harris et al. |
| 2014/0188136 A1 | 7/2014 | Cournoyer et al. |
| 2014/0222034 A1 | 8/2014 | Saliman |
| 2014/0276987 A1 | 9/2014 | Saliman |
| 2015/0034694 A1 | 2/2015 | Cappola |
| 2015/0039030 A1 | 2/2015 | Saliman et al. |
| 2015/0073442 A1 | 3/2015 | Saliman et al. |
| 2015/0157317 A1 | 6/2015 | Bagaoisan et al. |
| 2015/0173742 A1 | 6/2015 | Palese et al. |
| 2015/0173743 A1 | 6/2015 | Palese et al. |
| 2015/0209029 A1 | 7/2015 | Hendricksen et al. |
| 2015/0257756 A1 | 9/2015 | Sauer |
| 2015/0297215 A1 | 10/2015 | Hendricksen et al. |
| 2015/0313589 A1 | 11/2015 | Hendricksen et al. |
| 2016/0192926 A1 | 7/2016 | Hendricksen et al. |
| 2016/0220244 A1 | 8/2016 | Murillo et al. |
| 2016/0242765 A1 | 8/2016 | George et al. |
| 2016/0302789 A1 | 10/2016 | Hirotsuka et al. |
| 2018/0116651 A1 | 5/2018 | Saliman |
| 2018/0125479 A1 | 5/2018 | Saliman et al. |
| 2018/0303476 A1 | 10/2018 | Murillo et al. |

FOREIGN PATENT DOCUMENTS

| | | |
|---|---|---|
| CN | 103298503 A | 9/2013 |
| CN | 103717149 A | 4/2014 |
| EP | 0647431 A2 | 4/1995 |
| EP | 2030575 A1 | 3/2009 |
| EP | 2184015 A2 | 5/2010 |
| EP | 2081481 B1 | 11/2015 |
| JP | 3032847 U | 3/1991 |
| JP | 2009138029 A | 6/2009 |
| JP | 2009538190 | 11/2009 |
| SU | 376089 A | 4/1973 |
| SU | 728848 A1 | 4/1980 |
| SU | 1725847 A1 | 4/1992 |
| WO | WO 92/05828 A1 | 4/1992 |
| WO | WO 95/13021 A1 | 5/1995 |
| WO | WO98/11825 A1 | 3/1998 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO 01/56478 A1 | 8/2001 |
| WO | WO 02/07607 A1 | 1/2002 |
| WO | WO 02/096296 A1 | 12/2002 |
| WO | WO 03/077771 A1 | 9/2003 |
| WO | WO 2006/001040 A1 | 1/2006 |
| WO | WO 2006/040562 A1 | 4/2006 |
| WO | WO 2010/141695 A1 | 12/2010 |
| WO | WO 2011/057245 A2 | 5/2011 |

OTHER PUBLICATIONS

Ceterix; Novocut suture manager; retrieved from the internet (https://www.youtube.com/watch?v=6txqBJxvnuA) on Oct. 11, 2017; 1 page; Mar. 5, 2015.

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filing date and any foreign priority date) 1997.

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. is sufficiently earlier than the effective US filing date and any foreign priority date) 2007, 22 pages.

ArthroCare® Sportsmedicine, Sunnyvale, CA, SmartStitch® Suture Passing System with the PerfectPasserTM, Product brochure, (year of pub. is sufficiently earlier than the effective US filing date and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2 pgs.

Depuy Mitek, Inc; Raynham, MA, "Versalok Surgical Technique for Rotator Cuff Repair: The next generation in rotator cuff repair," Product brochure, (year of pub. is sufficiently earlier than the effective US filing date and any foreign priority date) 2007, 18 pages.

dictionary.com; Adjacent (definition); 5 pgs.; retrieved from the internet (http://www.dictionary.com/browse/adjacent) on Apr. 5, 2016.

Duerig, T. et al., "An overview of nitinol medical applications" Materials Science and Engineering A273-275, pp. 149-160; May 1999.

(56) References Cited

OTHER PUBLICATIONS

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.
Ma et al; "Biomechanical Evaluation of Arthroscopic Rotator Cuff Stitches," J Bone Joint Surg Am, Jun. 2004; vol. 86(6):1211-1216.
Medsfera; Suturing devices; accessed Dec. 4, 2012 at <http://www.medsfera.ru/shiv.html> 13 pages.
Nho et al; "Biomechanical fixation in Arthroscopic Rotator Cuff Repair," Arthroscopy: J of Arthroscop and Related Surg; vol. 23. No. 1, Jan. 2007: pp. 94-102.
Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).
Rimmer et al.; Failure Strength of Different Meniscal Suturing Techniques; Arthroscopy: The Journal of Arthroscopic and Related Surgery; vol. 11; No. 2; pp. 146-150; Apr. 1995.
Schneeberger, et al; "Mechanical Strength of Arthroscopic Rotator Cuff Repair Techniques: An in Vitro Study," J Bone Joint Surg Am., Dec. 2002; 84:2152-2160.
Smith&Nephew; Fast-Fix Meniscal Repair System (product webpage); 4 pgs.; downloaded Nov. 21, 2011 (http://endo.smith-nephew.com/fr/node.asp?NodeId=3562).
Strobel; Manual of Arthroscopic Surgery (1st Edition); Springer Verlag, Hiedelberg © 2002; pp. 127-129; Dec. 15, 2001.
USS SportsMedicine ArthoSewTM Single Use Automated Suturing Device with 8.6 mm ArthroPort Cannula Set, Instructions for Use, <http:www.uss-sportsmed.com/imageServer.aspx?contentID=5020&contenttype=application/pdf> accessed Apr. 25, 2007, 2 pages.
USS SportsMedicine ArthoSewTM Suturing Device, <http://www.uss-sportsmed.com/SportsMedicine/pageBuilder.aspx?webPageID=0&topicID=7141&xsl=xsl/productPagePrint.xsl>, product description, accessed Apr. 25, 2007, 3 pages.
Murillo et al.; U.S. Appl. No. 15/216,482 entitled "Automatically reloading suture passer devices that prevent entanglement," filed Jul. 21, 2016.
Peter et al.; U.S. Appl. No. 15/283,749 entitled "Knot tying accessory," filed Oct. 3, 2016.
Saliman et al.; U.S. Appl. No. 15/918,969 entitled "Transosteal anchoring methods for tissue repair," filed Mar. 12, 2018.

* cited by examiner

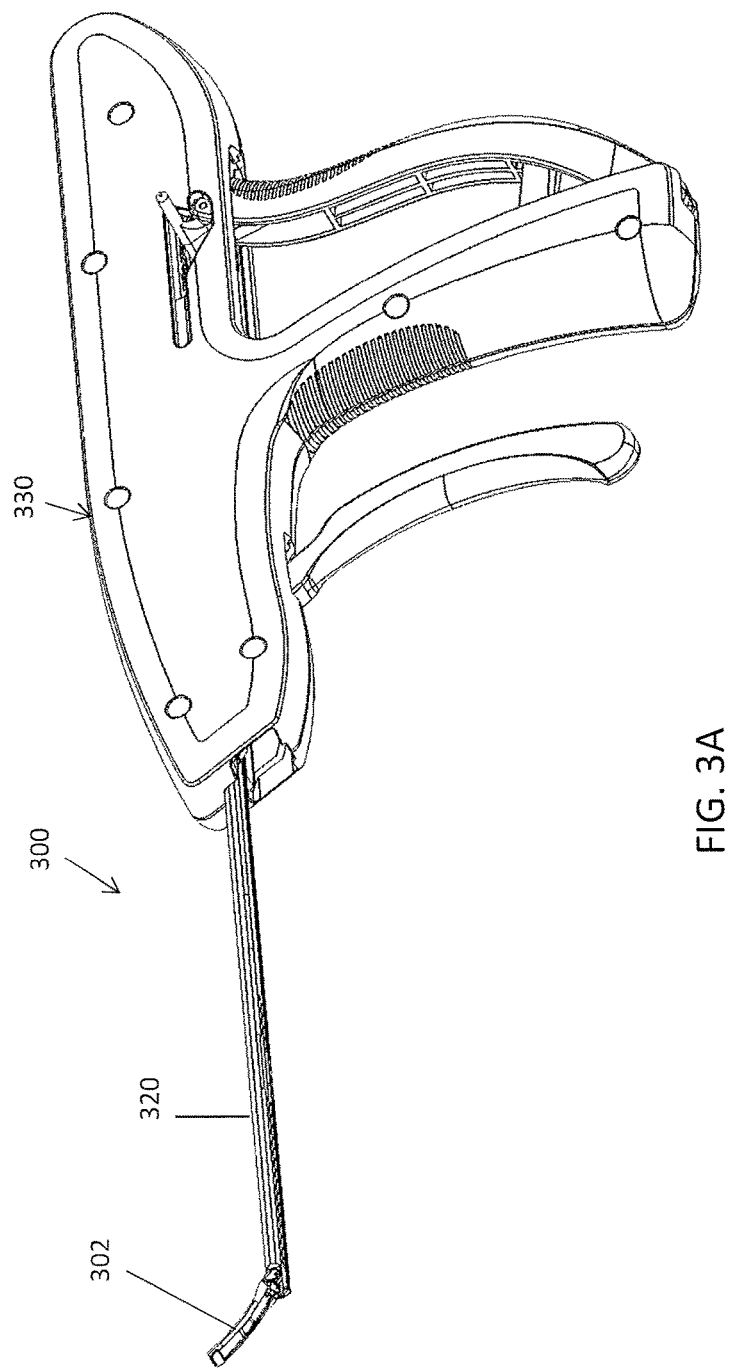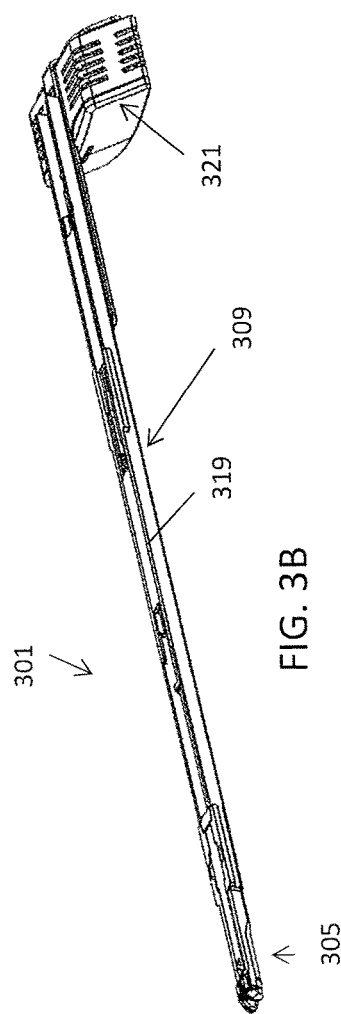
FIG. 3A
FIG. 3B

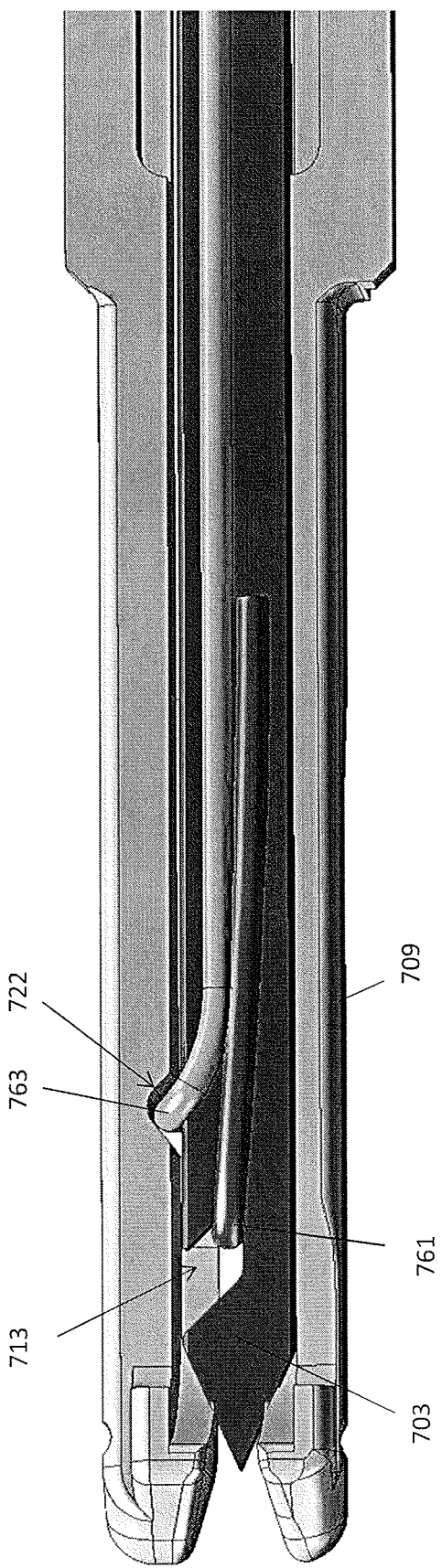
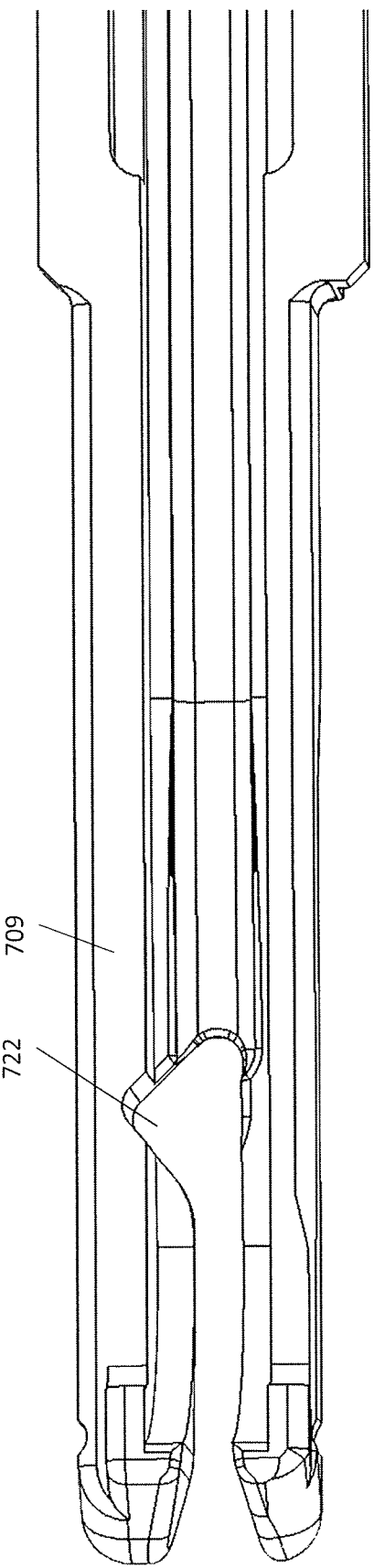
FIG. 7A
FIG. 7B

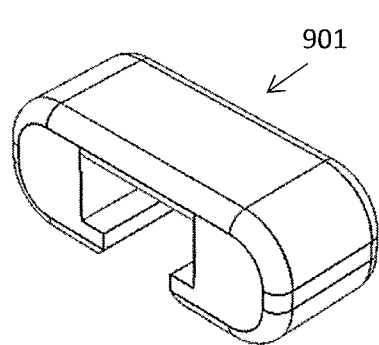
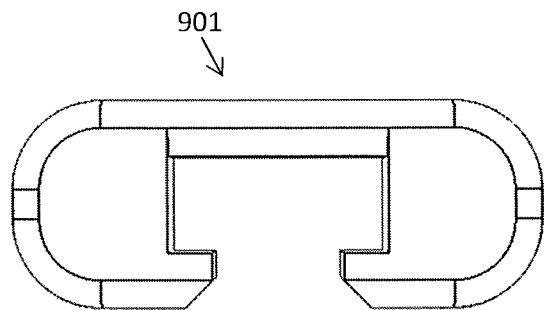
FIG. 9A    FIG. 9B
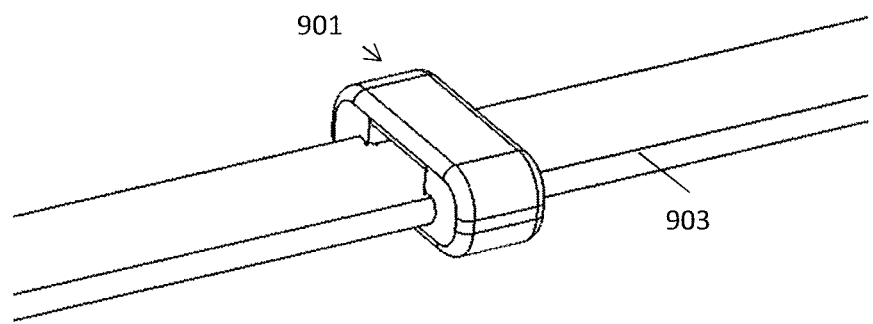
FIG. 9C
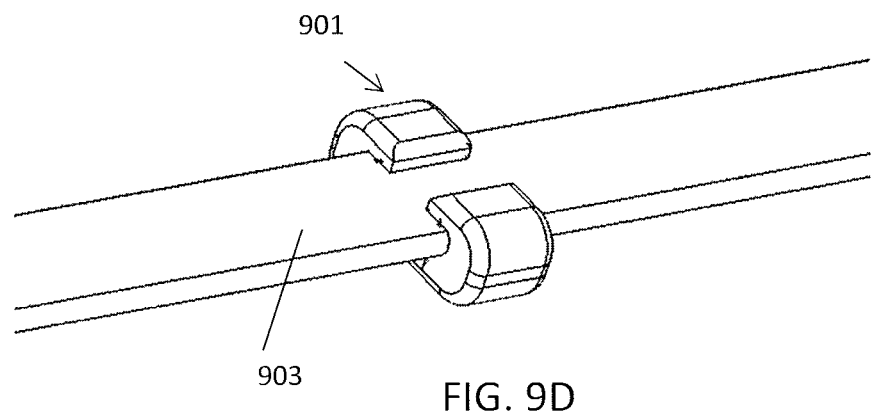
FIG. 9D

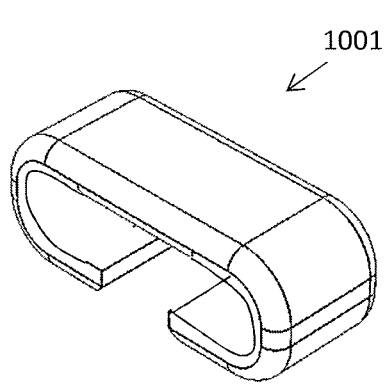
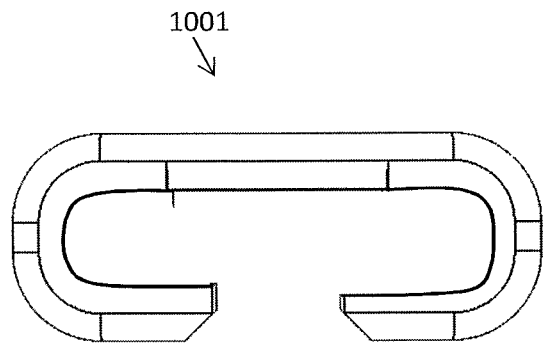
FIG. 10A
FIG. 10B
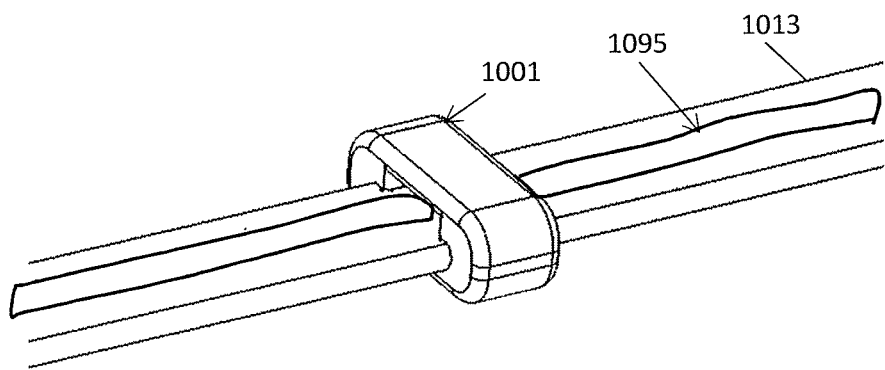
FIG. 10C
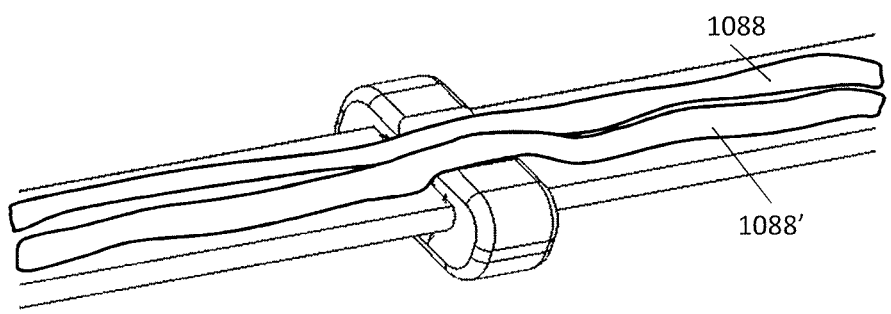
FIG. 10D

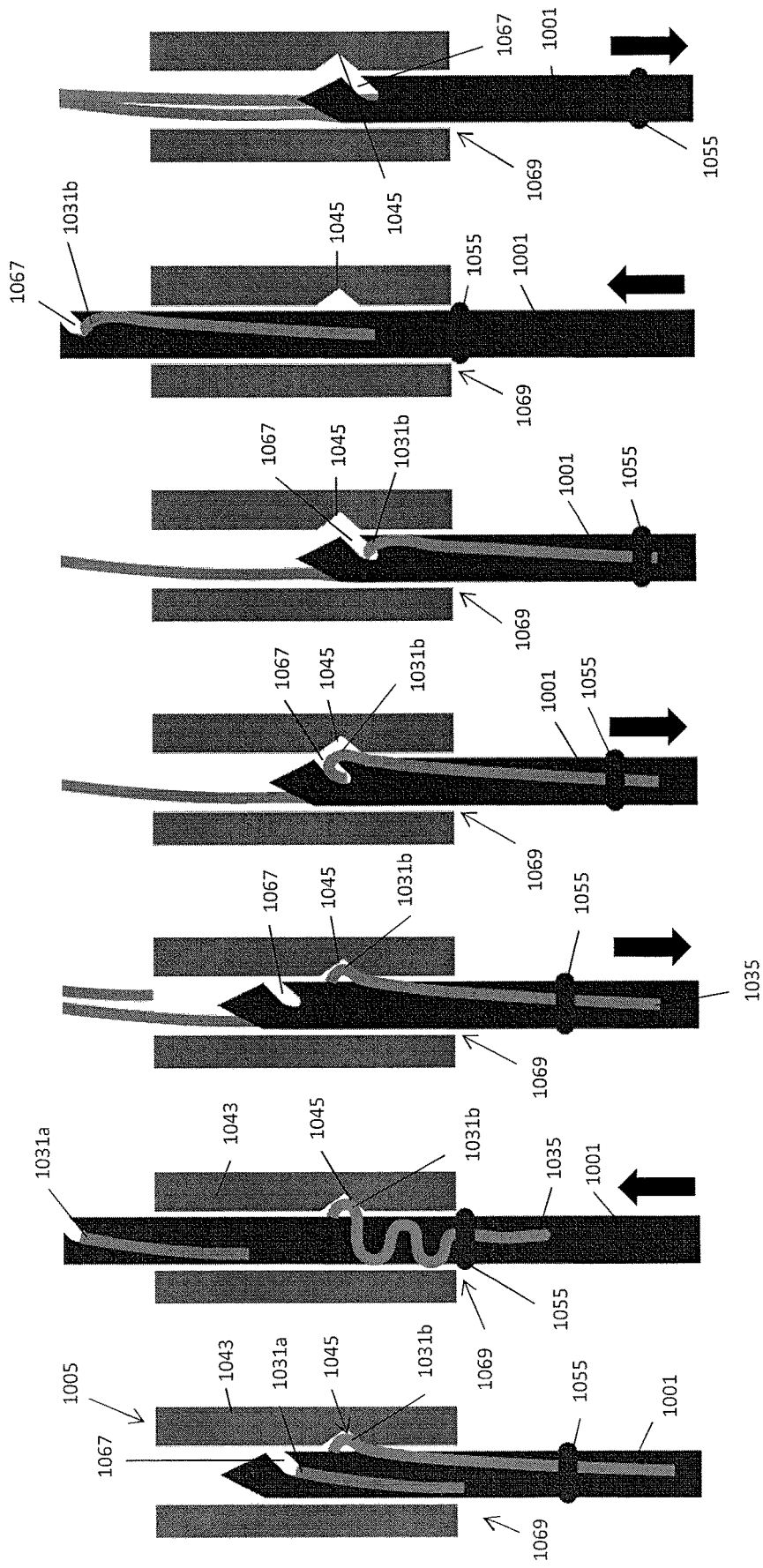

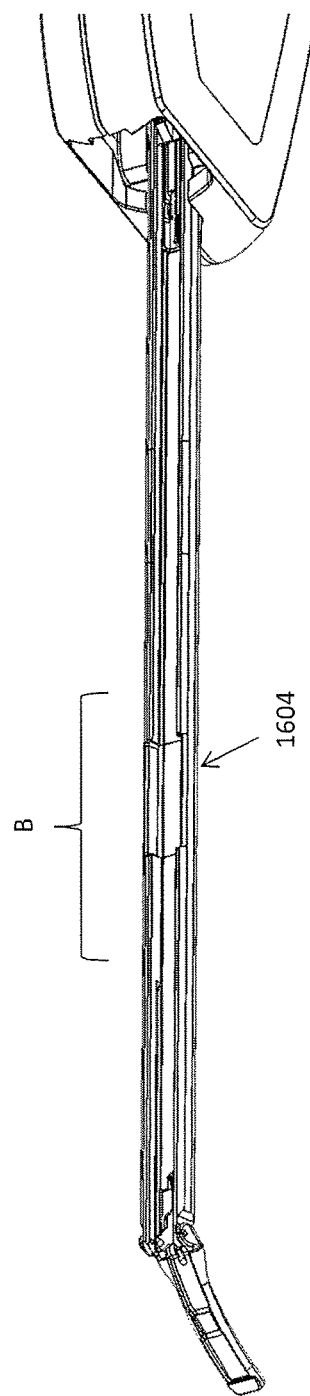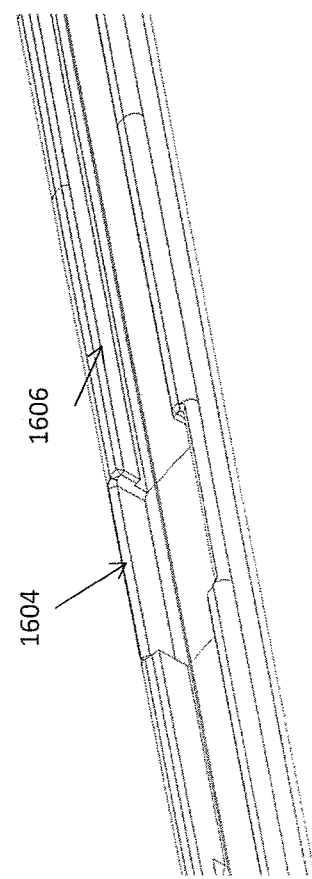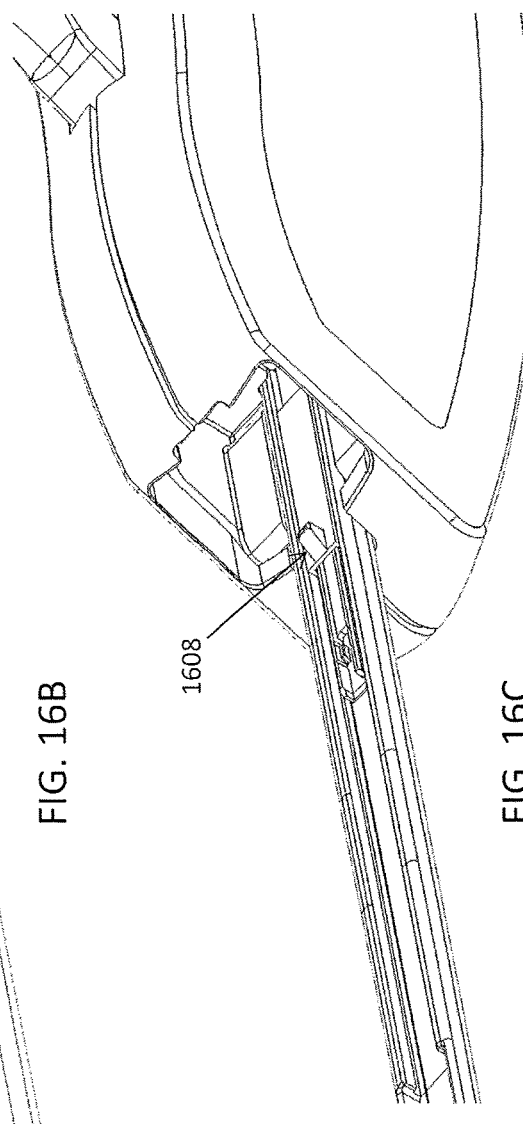

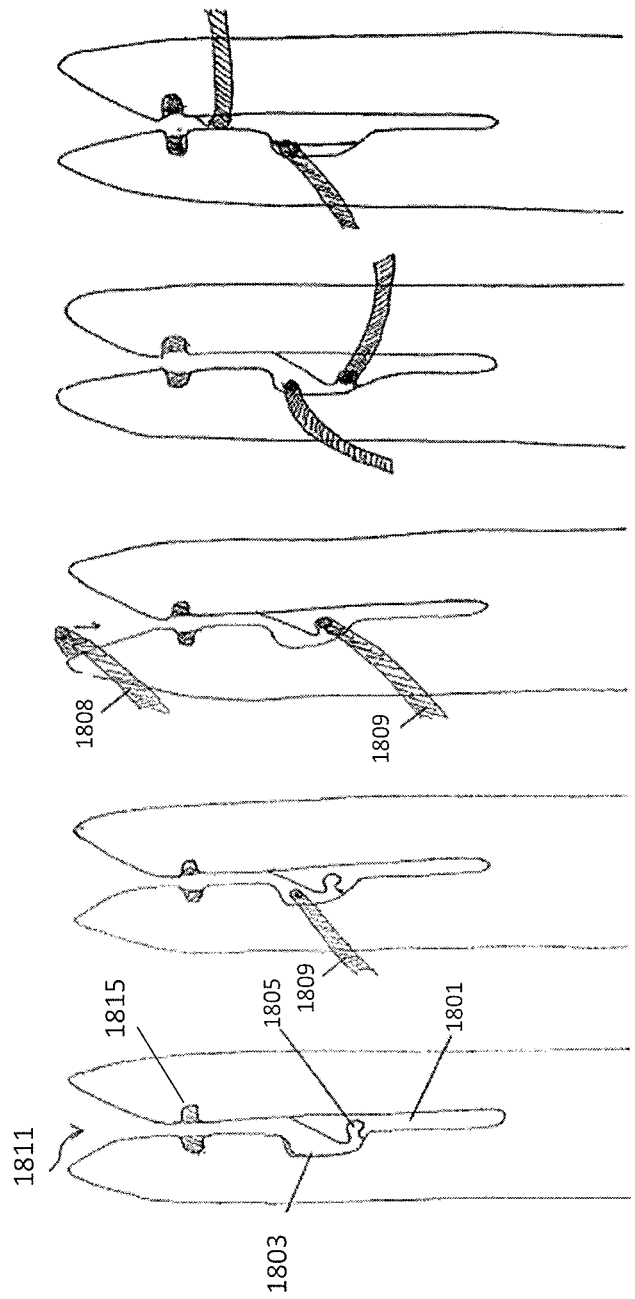

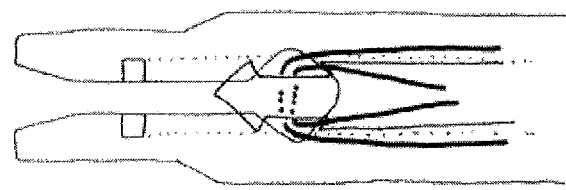
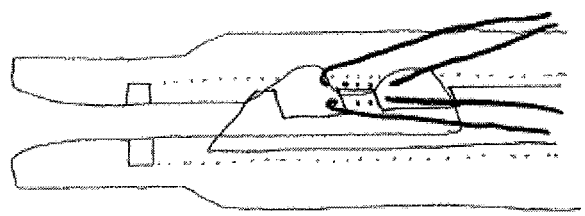
FIG. 19B
FIG. 19A

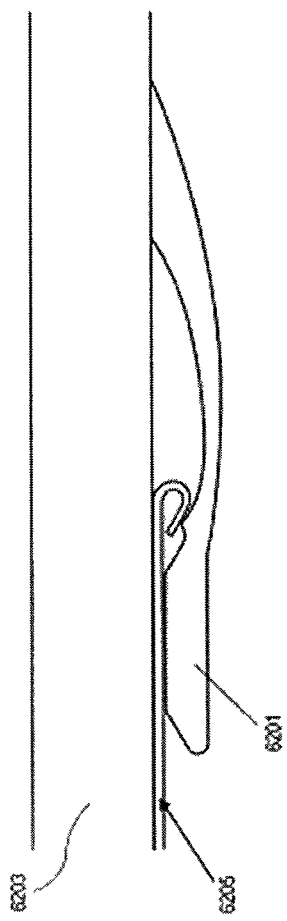

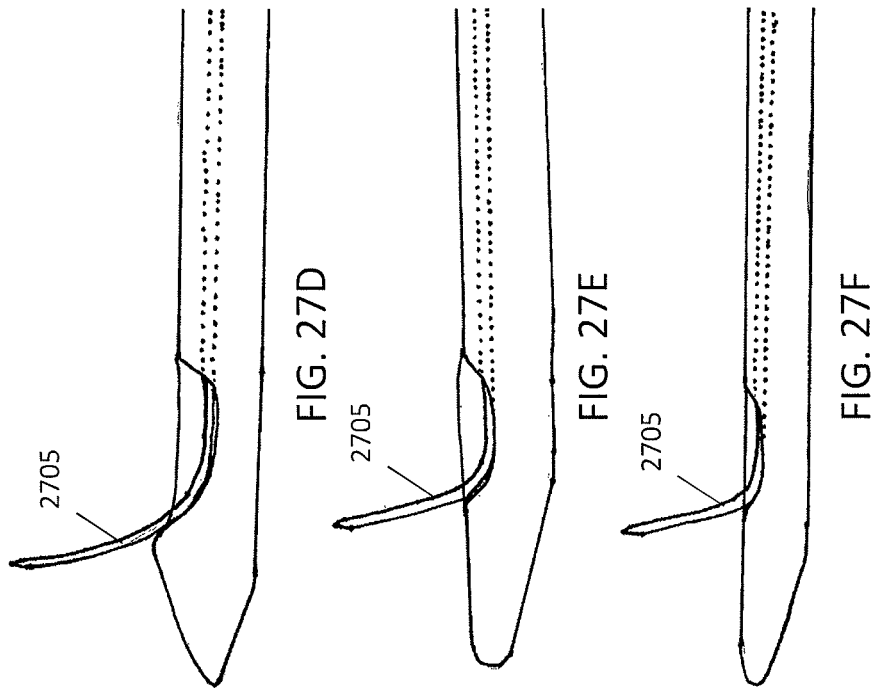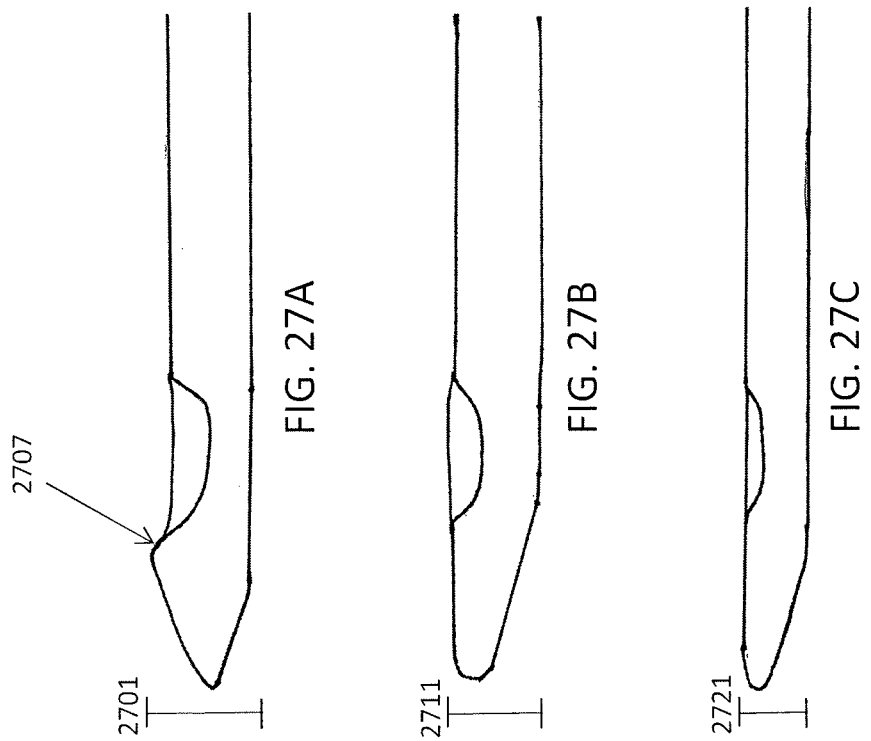

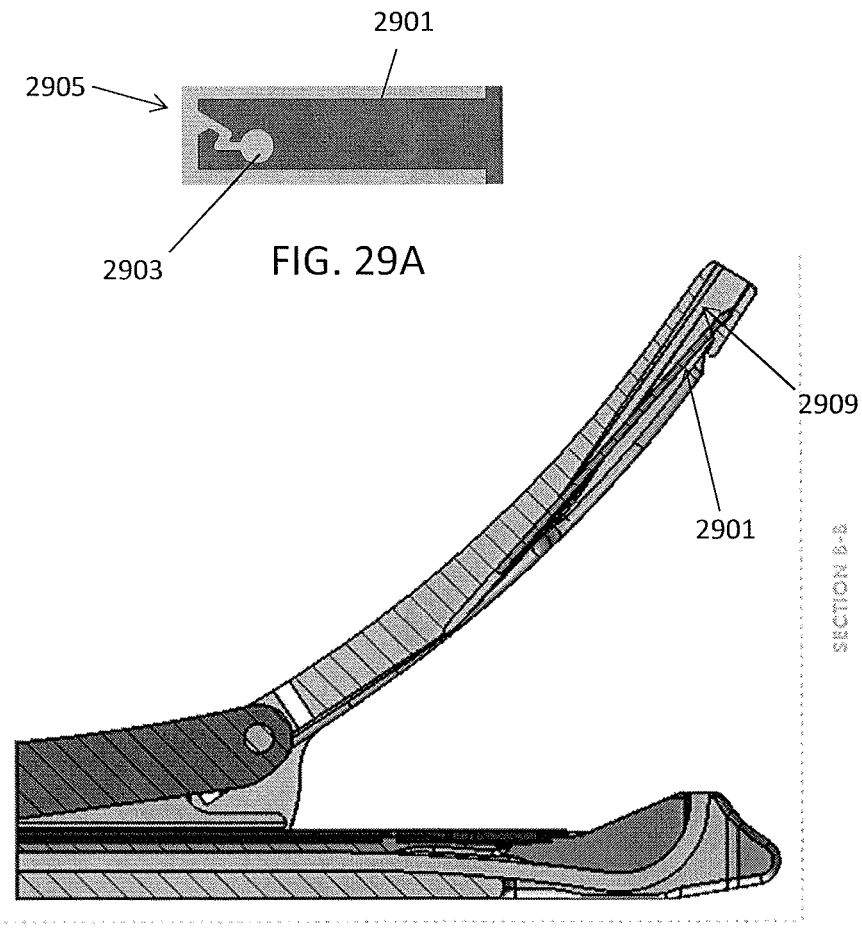
FIG. 29A
FIG. 29B
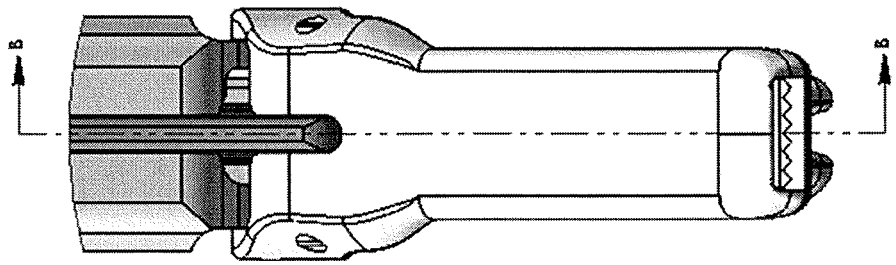
FIG. 29C

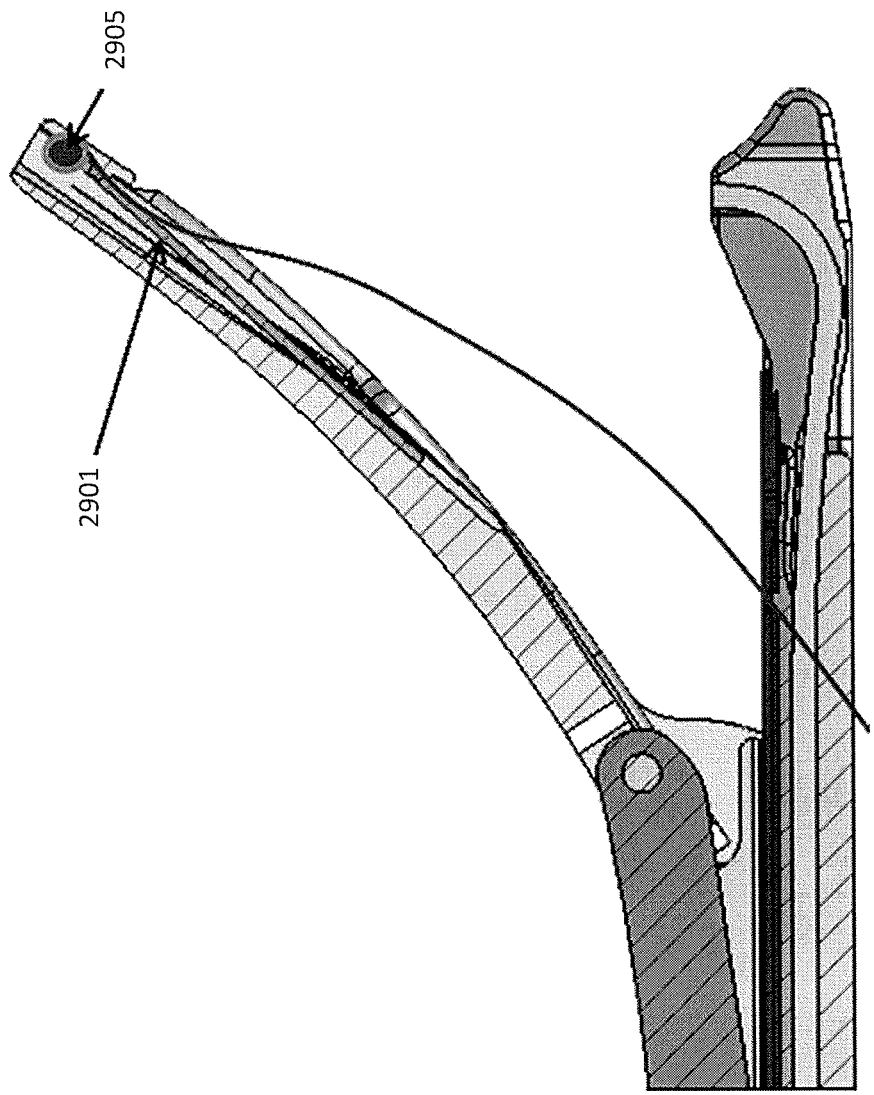

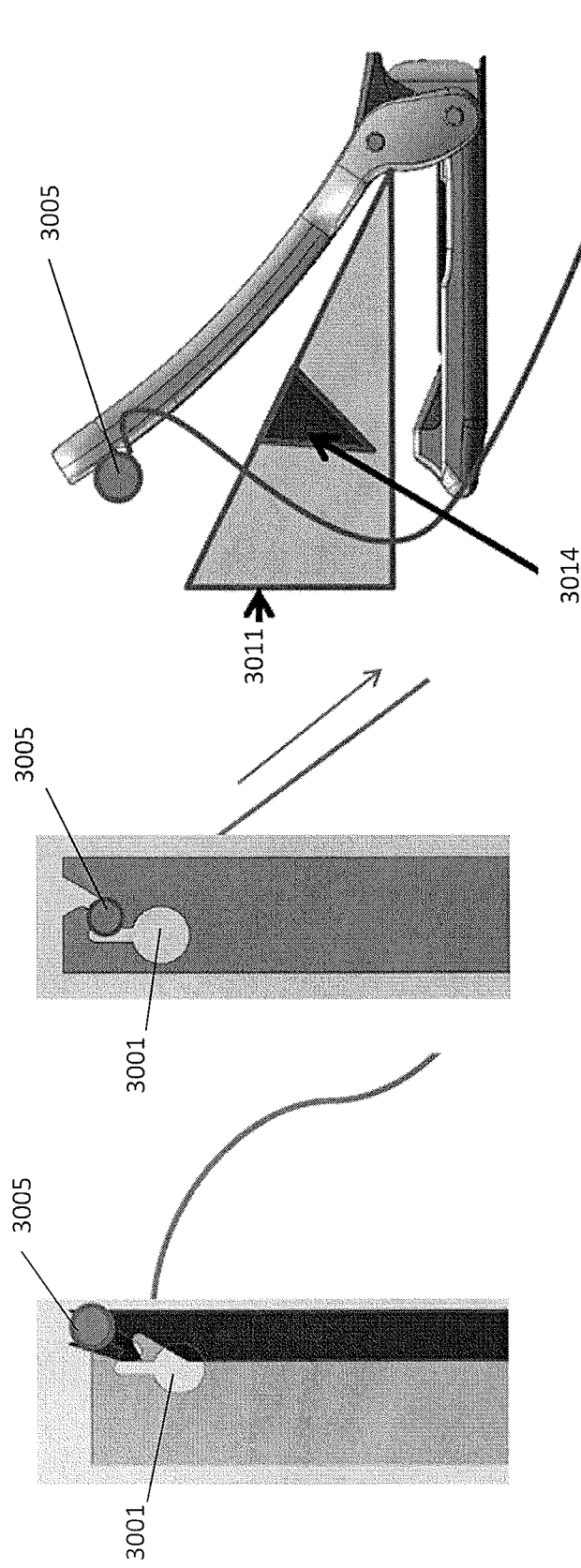

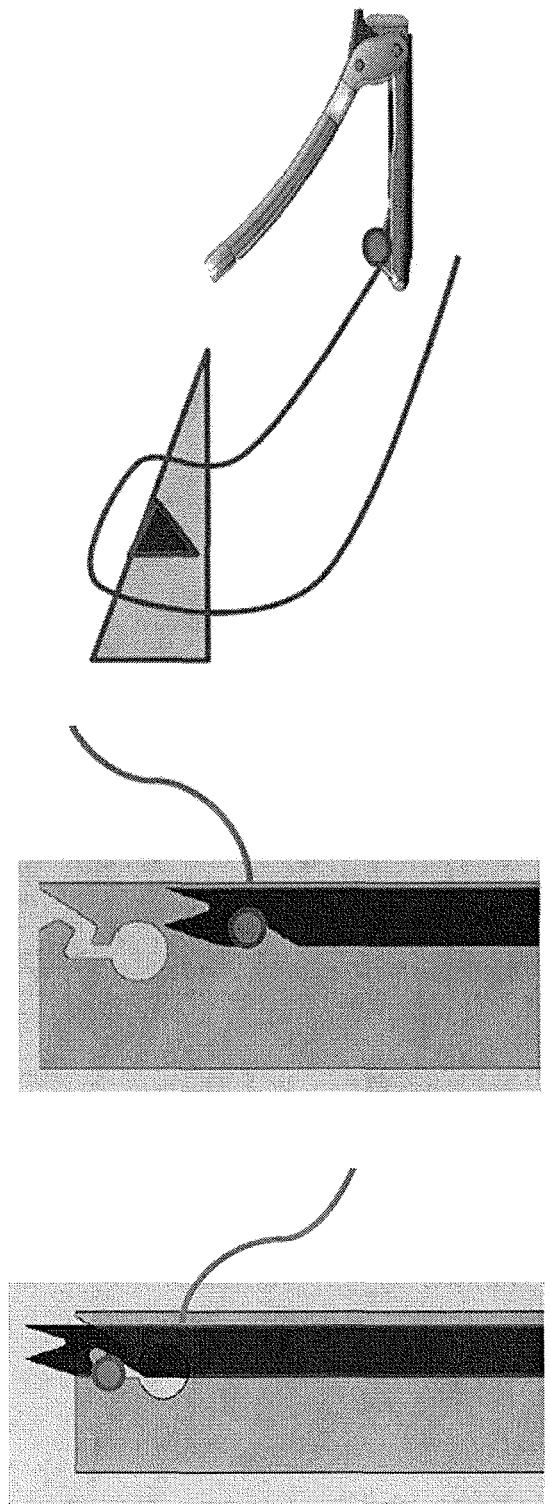

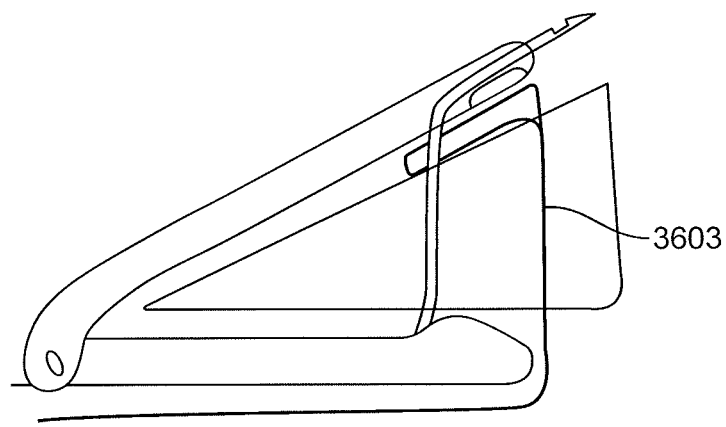
FIG. 36E
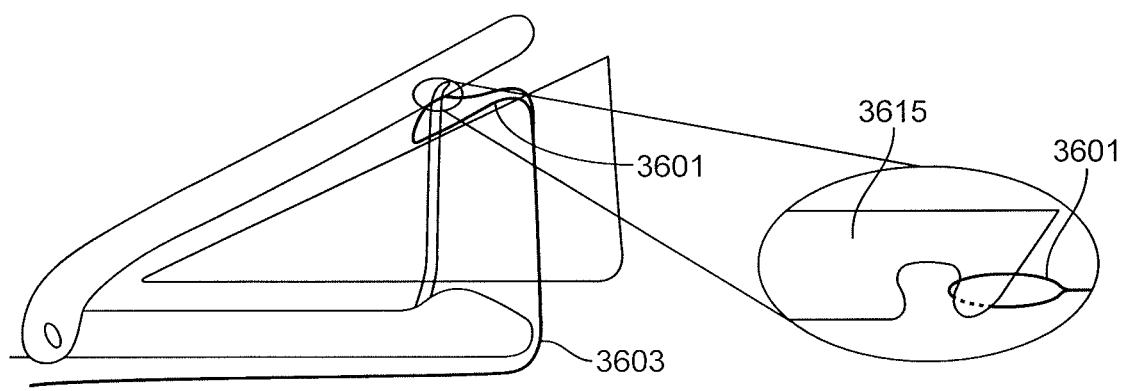
FIG. 36F
FIG. 36G

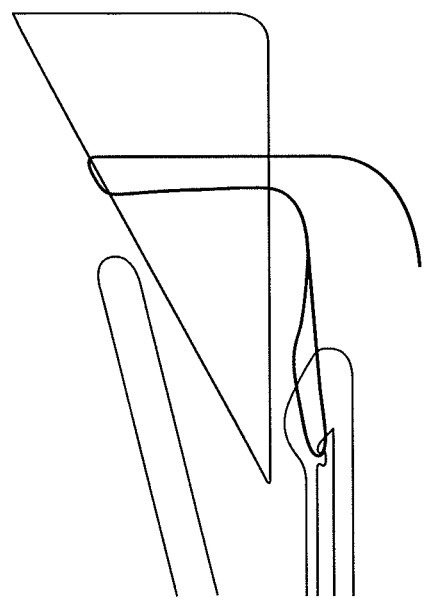
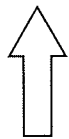
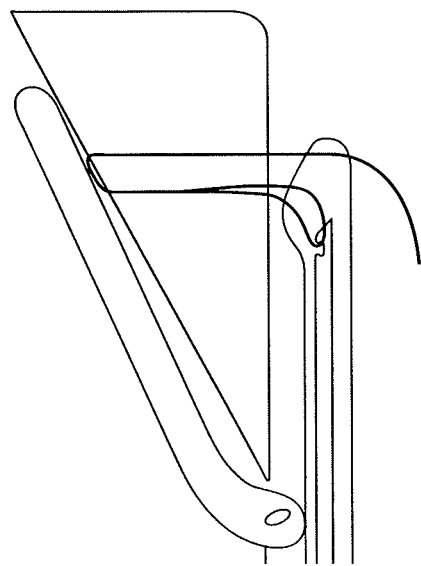
FIG. 36I
FIG. 36H

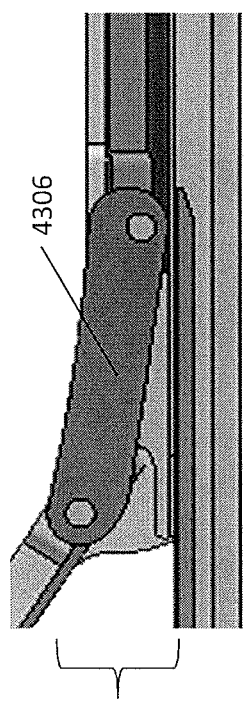
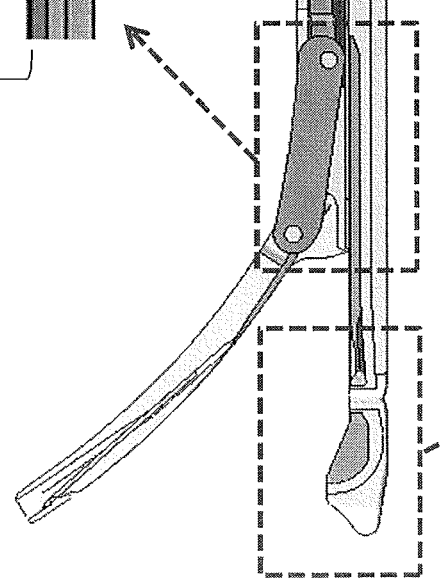
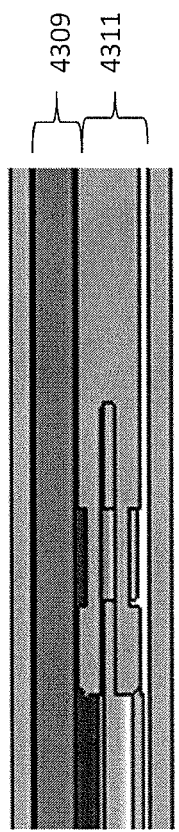
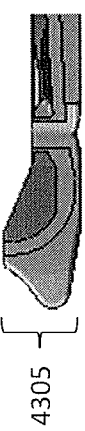
FIG. 43D
FIG. 43A
FIG. 43C
FIG. 43B

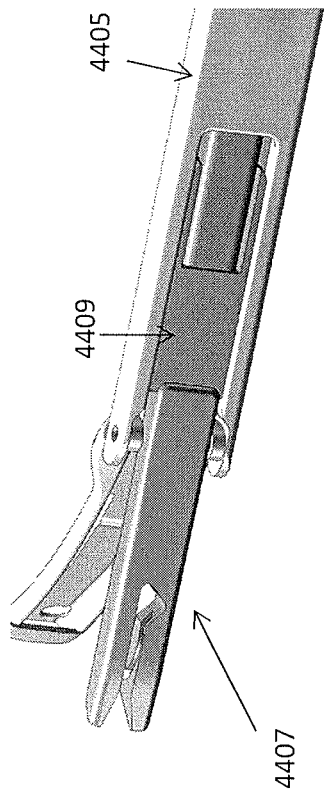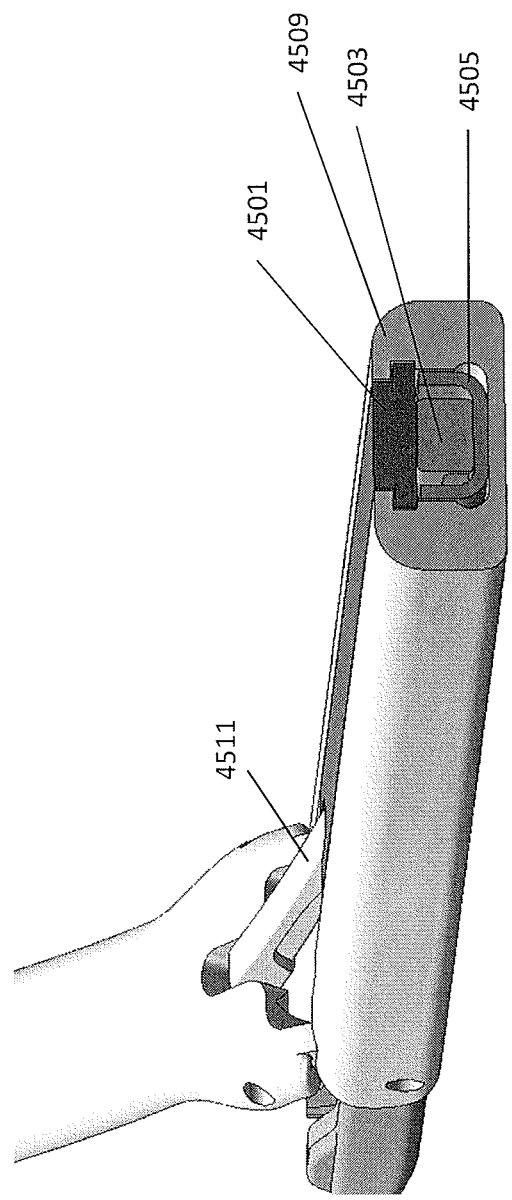
FIG. 44
FIG. 45A

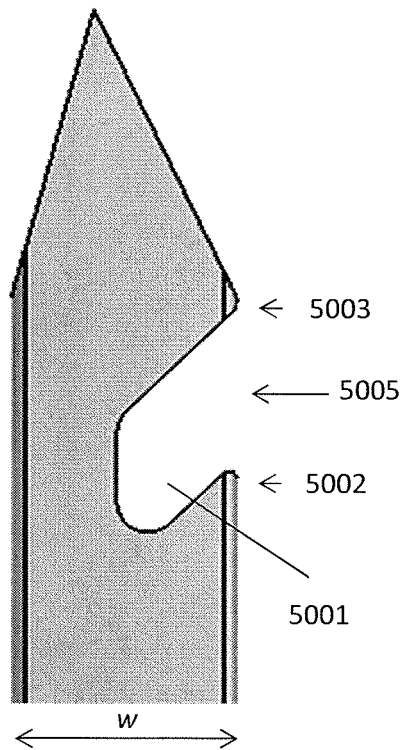
FIG. 50A
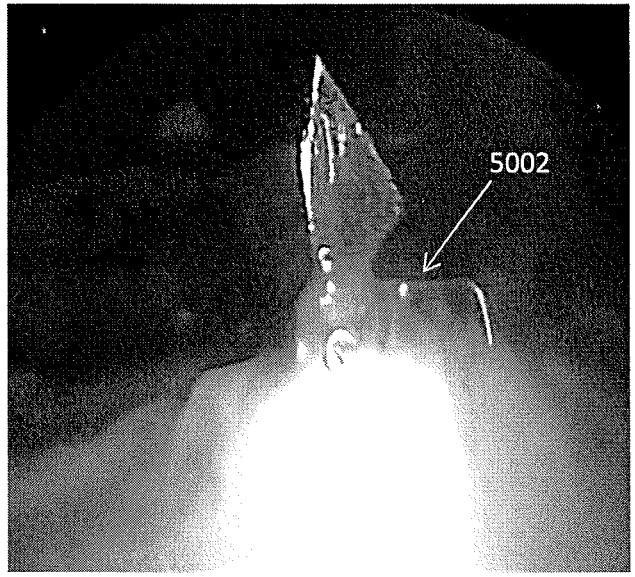
FIG. 50B
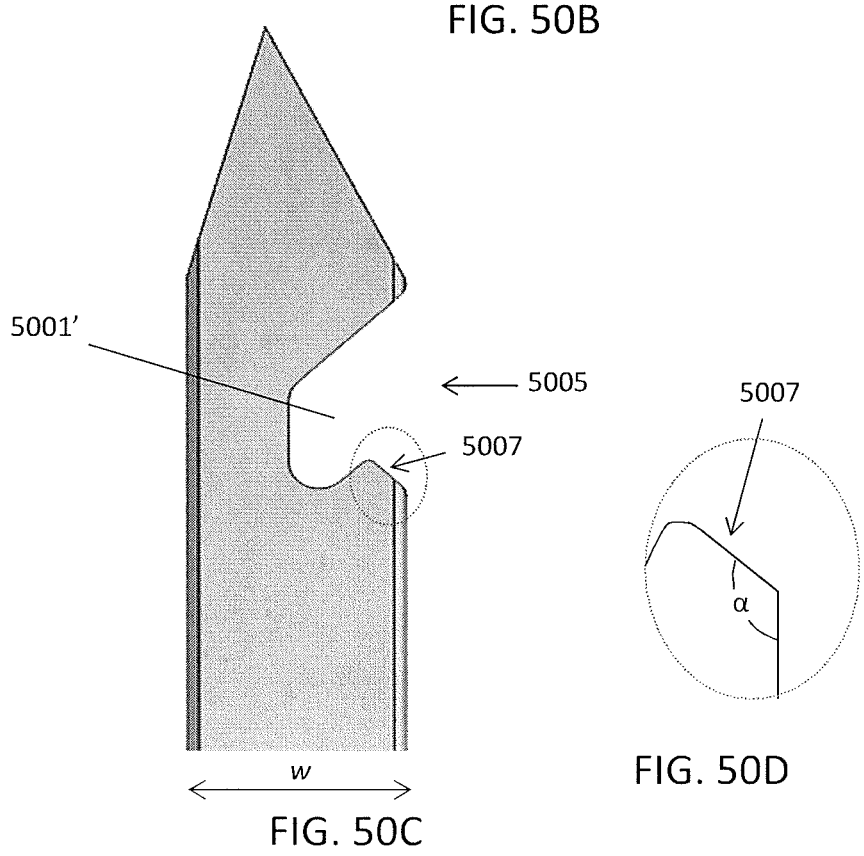
FIG. 50C
FIG. 50D

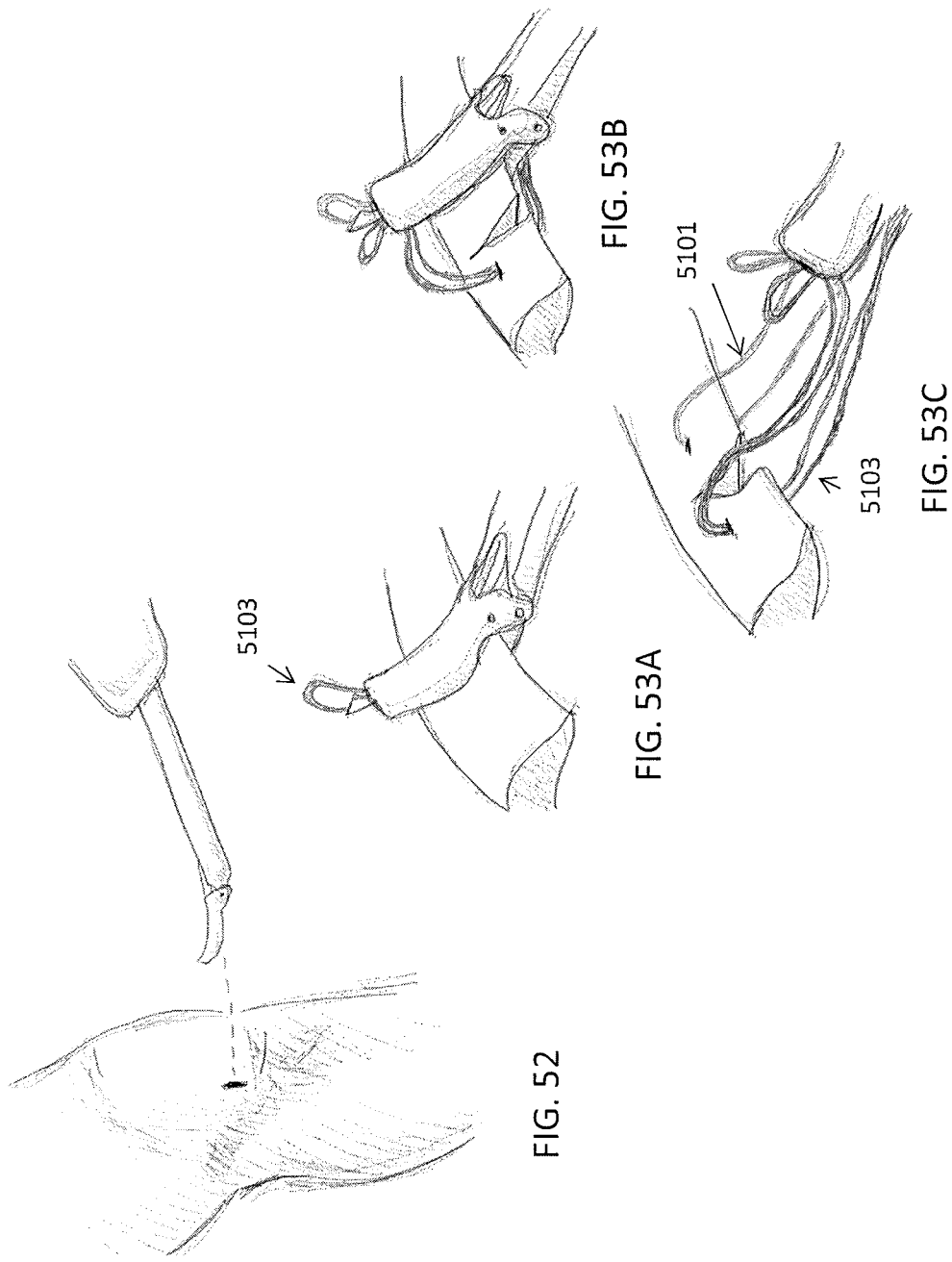

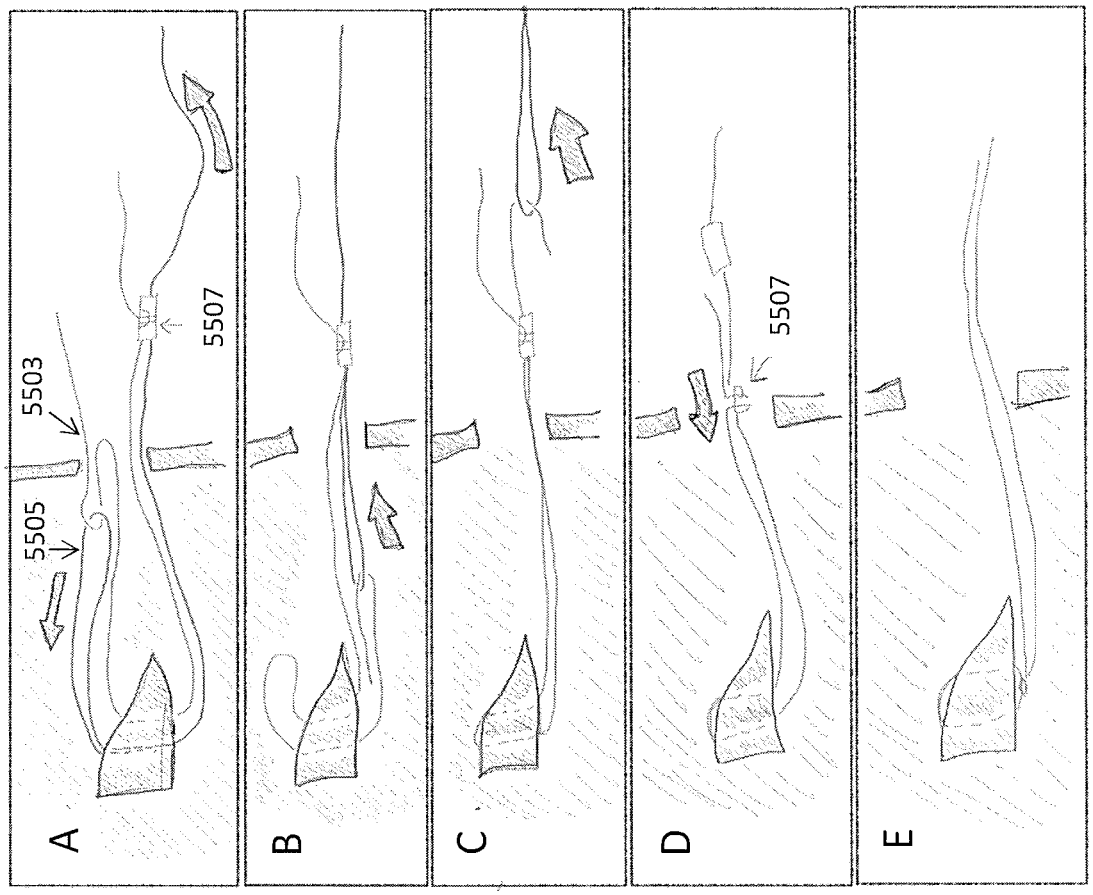
FIGS. 55A-E
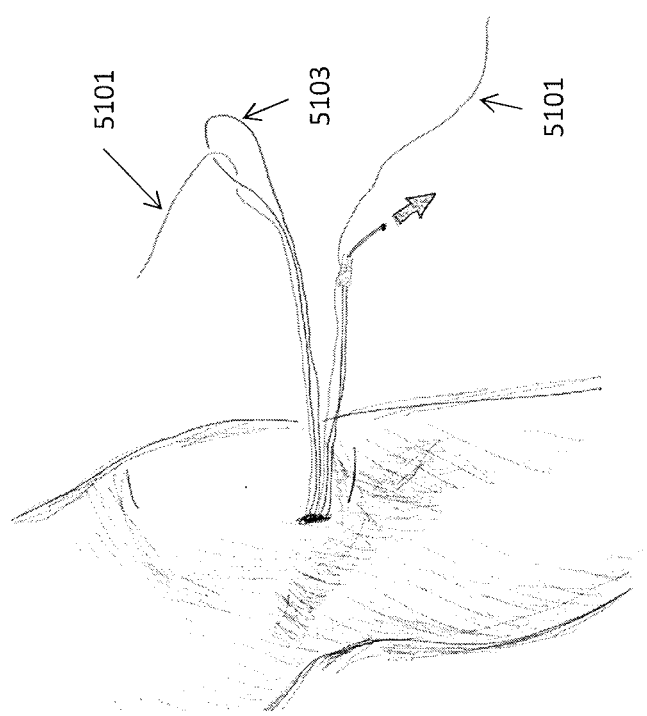
FIG. 54C

AUTOMATICALLY RELOADING SUTURE PASSER DEVICES AND METHODS

CROSS REFERENCE TO RELATED APPLICATIONS

This patent application is a divisional of U.S. patent application Ser. No. 14/572,485, filed Dec. 16, 2014, and titled "AUTOMATICALLY RELOADING SUTURE PASSER DEVICES AND METHODS" Publication No. US-2015-0196294-A1, which claims priority as a continuation-in-part to PCT/US2014/030137, filed Mar. 17, 2014 and titled "SUTURE PASSER DEVICES AND METHODS," Publication No. WO 2014/145381. Each of these applications is herein incorporated by reference in its entirety.

U.S. patent application Ser. No. 14/572,485 also claims priority to U.S. Provisional Patent Application No. 61/916,735, filed Dec. 16, 2013 and titled "AUTOMATICALLY RELOADING SUTURE PASSER DEVICES AND METHODS." Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses (e.g., devices and systems) described herein may be used to suture tissue, particularly in difficult to access regions. In particular, described herein are preloaded and automatically re-loading suture passers, suturing techniques, and methods of operating suture passers for surgical use including repairing tissue. For example, described herein are suture passers that may be used for performing arthroscopic (including minimally invasive, e.g., endoscopic) procedures.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, and difficulties loading the suture into the device, particularly for threading multiple suture loops.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

Some variations of suture passers, such as those described in U.S. Pat. No. 7,377,926 to Taylor, have opposing jaws that open and close over tissue. One, or in some variations, both, jaws open, scissor-like, so that tissue may be inserted between the open jaws. Unfortunately, such devices cannot be adequately positioned for use in hard to navigate body regions such as the joints of the body, including the knee (e.g., meniscus) and the shoulder because there is not room within the confines of the body (e.g., joint region) to open the scissoring jaws.

The knee joint is one example of a tissue region that is notoriously difficult to access. For example, the meniscus is a C-shaped piece of fibrocartilage which is located at the peripheral aspect of the joint (e.g., the knee) between the condyles of the femur and the tibia on the lateral and medial sides of the knee. The central two-thirds of the meniscus has a limited blood supply while the peripheral one third typically has an excellent blood supply. Acute traumatic events commonly cause meniscus tears in younger patients while degenerative tears are more common in older patients as the menisci become increasingly brittle with age. Typically, when the meniscus is damaged, a torn piece of meniscus may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult to perform because of the hard-to-reach nature of the region and the difficulty in placing sutures in a way that compresses and secures the torn surfaces.

Arthroscopy typically involves inserting a fiberoptic telescope that is about the size of a pencil into the joint through an incision that is approximately ⅛ inch long. Fluid may then be inserted into the joint to distend the joint and to allow for visualization of the structures within that joint. Then, using miniature instruments which may be as small as ¹⁄₁₀ of an inch, the structures are examined and the surgery is performed.

The meniscus of the knee is just one example of a tissue that is difficult to access so that appropriate suturing may be performed. FIG. 2 illustrate the anatomy of the meniscus in the context of a knee joint. As shown in FIG. 2 the capsule region (the outer edge region of the meniscus) is vascularized. Blood enters the meniscus from the menisculocapsular region 291 lateral to the meniscus. A typical meniscus has a flattened bottom 298 (inferior surface or side adjacent to the tibia) and a concave top 296 (superior surface or side, adjacent to the femur), and the outer cross-sectional shape may be somewhat triangular, with a meniscus tip region 294. The outer edge of the meniscus transitions into the capsule 291. The meniscus may include circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally or horizontally, depending on the type of repair being performed. Most prior art devices for suturing or repairing the meniscus are only capable of reliably repairing vertical/longitudinal tears. Such devices are not typically useful for repairing radial or horizontal tears. Furthermore, prior art device mechanisms have a high inherent risk for iatrogenic injury to surrounding neurovascular structures and chondral surfaces.

Thus, there is a need for methods and apparatuses (e.g., devices and systems) for suturing tissue, particularly tissue in difficult to access regions of the body including the joints (shoulder, knee, etc.). In particularly, it has proven useful to provide a device that may simply and reliably reach and pass sutures within otherwise inaccessible tissue regions. Such devices should be extremely low profile, and may be adapted or otherwise configured to fit in the tight spaces of the joints. Finally, would be useful to provide suturing apparatuses that allow selective and specific penetration of the tissue by both the tissue penetrator (needle element) and a jaw so that complex (including right-angled) suturing patterns may be achieved.

There is also a need for methods and apparatuses for suturing tissue. In particular, it has proven useful to provide a device that may simply and reliably reach and pass sutures within otherwise inaccessible tissue regions. Further, there is a need for suture passers that can be automatically loaded (or preloaded) pass multiple lengths (e.g., bights) of suture though the tissue without requiring that they be manually reloaded, either within the tissue or by withdrawing them from the tissue.

Although a suture passers that may be preloaded or reloadable with one or more sutures have been suggested, these devices typically require manual loading, activation and control of the suture in order to operate. See, e.g., U.S. Pat. No. 8,460,318 to Murray. Although such devices can be loaded with multiple sutures, they cannot be preloaded and/or automatically loaded or operated, and therefore cannot be incorporated as part of a cartridge for a suture passer. However, suture passers that could pass two (or more) lengths of suture, including two or more portions of the same suture, without requiring manual loading or reloading, would be highly advantageous, as they could increase the ease of suturing and reduce the time required for surgical procedures, as well as elimination or reducing a possible source of operational error.

The preloaded suture passers, preloaded cartridges for suture passers, and methods of operating such apparatuses to repair tissue described herein are capable of automatically passing a preloaded length of suture and automatically preloading with a second length of suture. These apparatuses (e.g., devices, including suture passers, and cartridges for suture passers, and systems of suture passers) and the methods of operating them described herein may be used to access difficult-to reach tissues.

The apparatuses and methods described herein may address the needs and potential benefits briefly discussed above.

SUMMARY OF THE DISCLOSURE

Described herein are preloaded cartridges for suture passers, preloaded suture passers, systems including preloaded suture passers and/or cartridges for suture passers, and methods of operating any of these to pass multiple lengths or suture and/or repair tissue. In particular, described herein are preloaded cartridges in which a first length of suture is preloaded into the tissue penetrator (e.g., needle) and, after passing the first length of suture, the cartridge automatically applies tension to load a second length of suture into the tissue penetrator. The cartridge is typically configured to be fully-enclosed, though with opening from which the loaded tissue penetrator may be extended and retracted. The cartridge may be configured as a jaw for use with a suture passer, or may include a jaw region. The cartridge may be coupled to a durable (e.g., reusable) suture passer; the cartridge may be disposable or recyclable. The cartridge may be coupleable to a suture passer, and may be slideable or adjustable once on the suture passer. The suture passer may engage with the cartridge to control the position of the jaw portion of the suture passer and/or the tissue penetrator.

In any of the apparatuses and methods described herein, the tissue penetrator is preloaded with a first bight of suture in a suture engagement portion of the tissue penetrator, and also includes a second bight of suture positioned to be loaded into the tissue engagement portion when the first bight has been passed by the suture passer. Importantly, the apparatus includes a releasable hold securing a portion (such as an end region) of the suture to the tissue penetrator so that this portion of the suture can move with the tissue penetrator; sliding the tissue penetrator may therefore tension (e.g., pull taught) a region of suture between the portion held by the releasable hold and a second bight of suture. If the suture engagement portion of the tissue penetrator (needle) is empty, the tension can pull the second bight of suture into the tissue engagement region for automatically reloading the second bight into onto the tissue penetrator. The second bight of suture is typically held in a suture holding region that remains fixed relative to the tissue penetrator.

For example, a replaceable jaw cartridge that is preloaded with suture, for use with a suture passer device, may include: a jaw housing configured to releasably engage the suture passer device; a tissue penetrator configured to slide distally and proximally within the jaw housing; a suture within the jaw housing, the suture comprising a first bight region loaded in a suture engagement region at a distal end region of the tissue penetrator, and a second bight region loaded in a suture holding region within the jaw housing; and a releasable hold on the tissue penetrator that releasably secures a first end region of the suture against the tissue penetrator; wherein the releasable hold is configured to hold the portion of the suture between the first end portion and the second bight region in tension when the tissue penetrator is withdrawn proximally so that the second bight region is loaded into the suture engagement region after the first bight region has been removed from the suture engagement region.

In some variations the cartridge (including the second jaw, suture and tissue penetrator) can clip onto and off of a compatible suture passer assembly (e.g., that includes a first jaw, body and handle at the proximal end of the body). The suture cartridge may be replaceable (swapped in/out) while the suture passer assembly is re-useable with different cartridges (e.g., durable). In some variations the cartridge portion is not swappable, and may not even be a distinct element, but may be integrated into the suture passer. Thus, in some variations a separate cartridge is not used, but instead the suture passer includes an integrated housing in or near the second jaw, in which the tissue penetrator, suture (e.g., first and second bights of suture), suture holding region and releasable hold are housed. These variations may be referred to as "integrated" preloaded and/or automatically reloading suture passers. In any of the apparatuses described herein, unless the context indicates otherwise, one or more aspects of a preloaded and/or automatically reloading cartridge may be incorporated in a suture passer that does not include a replaceable/removable cartridge, such as an integrated preloaded/automatically reloading suture passer.

Any of the apparatuses described herein (including preloaded cartridges, systems using preloaded cartridges, or integrated preloaded suture passers) may also include in the enclosure or housing holding the tissue penetrator and suture, one or more suture management elements such as guides, funnels, storage regions, spools, etc. to direct or hold the suture.

Any of the apparatuses described herein may include a deflection surface at or near an exit through the jaw housing, wherein the deflection surface is configured to deflect the tissue penetrator away from the jaw housing as the tissue penetrator slides distally out of the exit. The tissue penetrator may be generally configured to exit laterally from the side of the second jaw (e.g., the replaceable jaw cartridge). The tissue penetrator may be an elongate, thin, flat, or otherwise bendable structure. The tissue penetrator may be a metal (e.g., a shape memory alloy such as Nitinol) that is capable of being stored in a relatively straight configuration, and deflected one or more times when passing a length of suture, then restored to the relatively straight configuration when retracted back into the jaw housing.

A jaw housing may be configured to completely enclose the suture and tissue penetrator until the tissue penetrator is extended from the jaw housing. The jaw housing may be completely closed or it may include one or more openings. The jaw housing may include a region configured as a jaw. This jaw region may be configured to mate with another jaw region of a suture passer, such as an upper or pivoting jaw; the two jaws may form a distal-facing opening that can be opened and closed relative to each other to partially surround and/or grip target tissue to be sutured. Thus, the jaw housing may include a tissue-engaging surface that can be positioned opposite another jaw surface on the suture passer. The tissue-engaging surface may be smooth, or it may include a texture or geometry that aids in grasping and/or holding tissue.

In variations in which the cartridge is replaceably coupleable to a suture passer, the suture passer may not be competent to pass suture without a cartridge attached; for example durable portion of the suture passer may include a handle, controls, an elongate body and a fixed or rotatable upper jaw member, but may lack a lower jaw (e.g., a sliding lower jaw) and/or a tissue penetrator. Such suture passers may be referred to herein as durable (or re-usable) suture passers, because they can be re-sterilized and reused, or generally used with multiple replaceable jaw cartridges.

Thus, in some variations the cartridge includes elements that help connect the cartridge to the durable suture passer. For example, a jaw housing may include a keyed connector configured for coupling with an elongate member of the suture passer device.

In general, the apparatuses described herein include a holding region (suture holding region) for holding the second bight of suture that will be automatically re-loaded into the suture engagement region of the tissue penetrator. For example, any of these apparatuses may include a suture holding region that is configured as a notched region between the tissue penetrator and an inner surface of the jaw housing. The suture holding region may act in conjunction with the releasable hold on the tissue penetrator to hold the length of suture between the suture holding region and the reliable hold in tension. In some variations the suture holding region pinches or grasps the second bight region of the suture. In other variations the suture holding region does not apply any force to the second bight region; because the second bight region bends over/within the suture holding region (e.g., a notch forming the suture holding region) the second bight region may be held in the suture holding region.

In general, the suture holding region may be configured to be positioned opposite from the suture engagement region of the tissue penetrator when the tissue penetrator is withdrawn proximally within the jaw housing. Thus, tension on the second bight region (e.g. from the releasable hold) may allow it to slide from the suture holding region into the suture engagement region when the first bight is no longer in the suture holding region and when the tissue penetrator has been positioned within the housing to align the suture engagement region with the suture holding region.

Any appropriate suture may be used, including synthetic, natural or hybrid sutures. The suture may be monofilament or woven, and may be coated or uncoated. Although in some variations different suture may be used, in general the first and second bights of suture may be formed from different regions of the same suture. For example, the first bight region may be formed as a bend in the suture located near a distal end of the suture and the second bight region may be formed as a bend in the suture located near the proximal end of the suture.

In general, a releasable hold is attached to the tissue penetrator and moves with the tissue penetrator; the releasable hold typically holds an end region of a suture against the tissue penetrator as it moves and holds the end region relatively fixed to the tissue penetrator, providing tension to the pull the second bight suture to load it into the tissue penetrator. If the force (tension) on this length of suture exceeds a threshold (e.g., a release threshold), the releasable hold will release the suture; in some variations the suture is not completely released above the threshold, but the releasable hold continues to apply a holding force to the end region of the suture that is less than the release force. In some variations the releasable hold stops applying a holding force when the tension exceeds the release threshold. Any appropriate releasable hold may be used. In general, the releasable hold holds a portion of the suture against the tissue penetrator (needle). The releasable hold may push, press, clamp, pinch, bind, or otherwise temporarily secure the suture against the suture passer. For example, a releasable hold may comprise one or more of: an O-ring, a clip, a friction releasable hold, a band, a clamp, a frangible hold, a wax hold, and a releasable adhesive. The releasable hold may include multiple holding sites (e.g., two or more mechanical holding sites, a mechanical holding site and an adhesive holding site, etc.). In general, the releasable hold is positioned proximally on the tissue penetrator relative to the suture engagement region (which may be positioned near the distal tip of the tissue penetrator); the spacing from the distal tip/suture engagement region is typically greater than the distance traveled by the tip of the tissue penetrator so that the releasable hold remains within the housing during normal operation. Although the releasable hold is typically configured to attached to and move with the tissue penetrator, so as to hold an end portion of the suture fixed to the tissue penetrator, in some variations the releasable hold may slide or be moved on/along the tissue penetrator. In other variations the releasably hold may be fixedly attached to the tissue penetrator.

The needle may also be adapted to help releasable secure a portion of the suture with the suture engagement region. For example, the tissue penetrator may be bent or shaped to help pinch the suture against the releasable hold. In some variations the region of suture may also be configured to engage the releasable hold (e.g., including a knot, aglet, ferrule, etc.).

Any component that couples with (and slides with) the tissue penetrator may be configured as a releasable hold. For example a needle sled (sled) may be configured as a releasable hold. In general, the tissue penetrator within the apparatus may be a sled distally/proximally and extended from and retracted back into the jaw housing (e.g., lower jaw housing, cartridge housing, etc.). Thus, the jaw housing may also include/enclose a sled (e.g., needle sled) configured to couple with the tissue penetrator to facilitate sliding of the tissue penetrator within the jaw cartridge. In variations in which the jaw cartridge is replaceably coupled to a durable suture passer, either or both the tissue penetrator and/or the needle sled may couple with a shaft in the durable suture passer that is also connected to a control on a handle region to control the sliding (extension/retraction) of the suture passer. The needle engagement region may be a keyed region that allows pushing and/or pulling of the tissue penetrator within and out of/into the housing. The needle may be actuated independently of any sliding of the jaw housing relative to the durable suture passer, in variations in which the jaw housing (forming a second or lower jaw) may be slide/moved axially and distally relative to the other jaw member of the suture passer. In some variation the needle and the lower jaw may be moved in conjugate motion.

The sled may be configured as a releasable hold, so that the releasable is part of the sled. For example, the sled may from one or more narrow gap regions into which an end portion of suture may be pinched against the body of the tissue penetrator when the tissue penetrator is coupled with the sled and loaded with suture. In some variations the distal end portion of the sled comprise one or more such gap regions for holding an end portion of the suture. In some variations the sled is configured to couple with the tissue penetrator and releasable hold the end portion of the suture against the tissue penetrator. The tissue penetrator may be bent or curved (e.g., by the sled) to help hold the end region of the suture against the tissue penetrator.

In variations of the apparatus in which the tissue penetrator couples directly to an actuator to slide the tissue penetrator, the engagement between the tissue penetrator and the actuator (push/pull rod, shaft, etc.) may be configured as a releasable hold. Alternatively, a separate releasable hold may be coupled to the tissue penetrator.

The housing (e.g., jaw housing) may also include a storage region for storing the length within the housing. For example, the apparatus may include a suture capsule region configured to hold a portion of the suture. The storage capsule region may be at the proximal end of the apparatus. For example, in variations in which the first and second bight are formed of the proximal and distal end regions of a single suture, the region of suture between the first and second bight may extend proximally along the shaft of the jaw housing to a suture capsule at the proximal end that has an enlarged hollow allowing storage of this intermediate region of suture until it is drawn out of the distal end of the housing when passing the suture to the opposite jaw.

In variations in which the jaw housing is configured as part of a cartridge, the apparatus may include a connector configured to couple the jaw cartridge to the suture passer device and to uncouple the jaw cartridge from the suture passer device. For example, the jaw housing may include keyed regions, such as one or more projections (e.g., flanges, pins, bumps, etc.), to engage with a recess region in the durable suture passer device, or one or more receiving regions (e.g., channels, slots, etc.) to receive projecting portions of the suture passer device, or both.

In some variations, the jaw cartridge includes a suture guide within the jaw housing positioned intermediate of the distal end of the jaw housing and the releasable hold. For example, the housing may include or hold a funnel or channel in which the suture passes, which may help guide the suture so that the movement of the tissue penetrator within the housing does not undesirably engage (e.g., tangle) the suture.

As mentioned, the jaw housing and/or the entire jaw cartridge may slideably engage with a durable suture passer device so that jaw member portion of the jaw housing slides distally to proximally along the long axis of the suture passer, in contrast with and independently of an upper jaw on the durable suture passer, which in some variations pivots relative to the long (distal-to-proximal) axis. For example, the jaw housing may be configured to couple to and uncouple from a durable suture passer to form a sliding lower jaw member on the suture passer so that the tissue penetrator can extend from the jaw housing to an upper jaw member.

For example, a replaceable jaw cartridge that is preloaded with suture, for use with a suture passer device, may include: an elongate jaw housing from a distal end to a proximal end in a first axis; a keyed region of the jaw housing configured to releasably engage the suture passer device; a tissue penetrator configured to slide distally and proximally within the jaw housing; an exit through the jaw housing near the distal end; a deflection surface near the exit configured to deflect the tissue penetrator away from the first axis as it slides distally out of the exit; a suture within the jaw housing, the suture comprising a first bight region loaded in a suture engagement region at a distal end region of the tissue penetrator, and a second bight region loaded in a suture holding region within the jaw housing; and a releasable hold on the tissue penetrator that releasably secures a first end region of the suture against the tissue penetrator and is configured to slide with the tissue penetrator; wherein the releasable hold is configured to hold the portion of the suture between the first end portion and the second bight region in tension when the tissue penetrator is withdrawn proximally so that the second bight region is loaded into the suture engagement region after the first bight region has been removed from the suture engagement region. Any of the features described above may be incorporated into this variations. For example, the jaw housing may be configured to completely enclose the suture and tissue penetrator until the tissue penetrator is extended from the jaw housing. The keyed region may comprise a keyed connector configured for coupling within a track region of an elongate member of the suture passer device.

Also described herein are suture passer systems with a preloaded suture, the system comprising: an elongate body extending distally and proximally; a first jaw coupled to a distal end of the elongate body; and a second jaw, the second jaw housing: a tissue penetrator configured to slide distally and proximally within the second jaw, a suture within the second jaw, the suture comprising a first bight region loaded in a suture engagement region at a distal end region of the tissue penetrator, and a second bight region loaded in a suture holding region within the second jaw, and a releasable hold on the tissue penetrator configured to hold a first end portion of the suture in tension when the tissue penetrator is withdrawn proximally so that the second bight region is drawn into the suture engagement region after the first bight region has been removed. The first jaw may be configured to pivot relative to the elongate body. The second jaw may be configured to slide distally and proximally relative to the elongate body.

In some variations, the second jaw comprises a replaceable jaw cartridge configured to releaseably engage with the elongate body so that the jaw cartridge may slide distally and proximally relative to the elongate body. For example, the second jaw may include a replaceable jaw cartridge configured to releaseably engage with the elongate body so that the jaw cartridge may slide distally and proximally relative to the elongate body. The second jaw may be configured to completely enclose the suture and tissue penetrator until the tissue penetrator is extended from the second jaw. The second jaw may include a keyed connector configured for coupling the second jaw with the elongate body.

The system may also include a deflection surface near an exit through the second jaw, wherein the deflection surface is configured to deflect the tissue penetrator away from the second jaw and towards the first jaw as the tissue penetrator slides distally out of the exit.

As mentioned above, the suture holding region may comprise a notched region between the tissue penetrator and an inner surface of the jaw housing. The suture holding region may be configured to be positioned opposite from the suture engagement region of the tissue penetrator when the tissue penetrator is withdrawn proximally within the second jaw.

Also as described above, the first bight region may be located near a distal end of the suture and the second bight region is located near the proximal end of the suture. Any of the releasable holds discussed above may be used. For example, the releasable hold may comprise one or more of: a sled, an O-ring, a clip, a friction releasable hold, a band, a clamp, a frangible hold, a wax hold, and a releasable adhesive.

The system may also include a sled configured to couple with the tissue penetrator to facilitate sliding of the tissue penetrator within the second jaw. The sled may be configured as (or may include) a releasable hold. The sled may couple the tissue penetrator with a driver (rod, shaft, etc.) on the suture passer for actuating the tissue penetrator. The system may also include a suture capsule region configured to hold a portion of the suture. The system may also include a releasable connector configured to couple the second jaw to the suture passer and to uncouple the jaw cartridge from the suture passer. The system (or any of the apparatuses described herein) may include a suture guide within the second jaw positioned intermediate of the distal end of the jaw housing and the releasable hold. The second jaw may comprise a housing that is configured to couple to and to uncouple from a suture passer to form a sliding lower jaw on the suture passer.

Also described herein are systems for multiply suturing tissue with a replaceable, preloaded jaw cartridge, the system comprising: an elongate body extending distally and proximally; a first jaw coupled to a distal end of the elongate body and configured to pivot relative to the elongate body; and a replaceable jaw cartridge configured to releaseably engage with the elongate body so that the jaw cartridge may slide distally and proximally relative to the elongate body, the jaw cartridge housing: a tissue penetrator configured to slide distally and proximally within the jaw cartridge, a suture within the jaw cartridge, the suture comprising a first bight region loaded in a suture engagement region at a distal end region of the tissue penetrator, and a second bight region loaded in a suture holding region within the jaw cartridge, and a releasable hold on the tissue penetrator configured to hold a first end portion of the suture in tension when the tissue penetrator is withdrawn proximally so that the second bight region is drawn into the suture engagement region after the first bight region has been removed.

Also described herein are methods of operating any of the apparatuses described. For example, described herein are methods of operating a suture passer that is preloaded with a suture. A method of operating a suture passer may include: forming a distal-facing opening between a first jaw of the suture passer and a second jaw; extending a distal tip of a tissue penetrator across the distal-facing opening from within the second jaw, wherein the tissue penetrator comprises a suture engagement region that is preloaded with a first bight region of the suture; retracting the distal tip of the tissue penetrator into the second jaw; withdrawing the tissue penetrator distally within the second jaw to tension the suture between an end region of the suture that is held by a releasable hold on the tissue penetrator and a second bight region of the suture, so that the second bight region is drawn into the suture engagement region of the tissue penetrator; and extending the distal tip of the tissue penetrator from the second jaw and across the distal-facing opening, wherein the tissue penetrator is carrying the second bight region of the suture.

The method may also include coupling a replaceable second jaw, configured as a jaw cartridge, to an elongate body of the suture passer, wherein the suture passer includes a first jaw pivotally coupled to a distal end region of the elongate body.

The step of forming a distal-facing opening between the first jaw of and a second jaw may comprise sliding the second jaw distally relative to the elongate body to form the distal-facing opening between a distal end region of the second jaw and the first jaw.

The method may also include uncoupling the jaw cartridge from the suture passer.

In some of the methods of operating the apparatuses described herein, the method may also include pivoting the first jaw relative to the elongate body and sliding the second jaw distally to form the distal-facing opening, and/or passing the first bight region of the suture to the first jaw.

For example, described herein are methods of operating a suture passer that is preloaded with a suture, the method comprising: coupling a replaceable jaw cartridge to an elongate body of the suture passer, wherein the suture passer includes a first jaw pivotally coupled to a distal end region of the elongate body, further wherein the jaw cartridge comprises a second jaw; forming a distal-facing opening between the pivotally coupled first jaw of the suture passer and the second jaw by sliding the second jaw distally relative to the elongate body to form a distal-facing opening between a distal end region of the second jaw and the first jaw; extending a distal tip of a tissue penetrator from within the second jaw and across the distal-facing opening, wherein the tissue penetrator comprises a suture engagement region that is preloaded with a first bight region of the suture; retracting the distal tip of the tissue penetrator into the second jaw; withdrawing the tissue penetrator distally within the second jaw to tension the suture between an end region of the suture that is held by a releasable hold on the tissue penetrator and a second bight region of the suture, so that the second bight region is drawn into the suture engagement region of the tissue penetrator; and extending the distal tip of the tissue penetrator from the second jaw and across the distal-facing opening, wherein the tissue penetrator is carrying the second bight region of the suture.

Also described herein are methods of operating a surgical suturing apparatus, the method comprising: coupling a replaceable jaw cartridge to an elongate body of a suture passer, wherein the suture passer includes a first jaw pivotally coupled to a distal end region of the elongate body and wherein the jaw cartridge comprises a second jaw; pivoting the first jaw relative to the elongate body; sliding the second jaw distally relative to the elongate body to form a distal-facing opening between the distal end region of the second jaw and the first jaw; extending a distal tip of a tissue penetrator from within the second jaw and across the distal-facing opening, wherein the tissue penetrator comprises a suture engagement region that is preloaded with a first bight region of the suture; passing the first bight region of the suture to the first jaw; retract the distal tip of the tissue penetrator into the second jaw and withdrawing the tissue penetrator distally within the second jaw to tension the suture between an end region of the suture that is held by a releasable hold on the tissue penetrator and a second bight region of the suture, so that the second bight region is drawn into the suture engagement region of the tissue penetrator; extending the tissue penetrator from the second jaw and across the distal-facing opening, wherein the tissue penetrator is carrying the second bight region of the suture within the suture engagement region; and retracting the distal tip of the tissue penetrator into the second jaw; and removing the jaw cartridge from the elongate body.

As described, in general the apparatuses (device and/or systems) described herein may be configured so that they can pass more than one length of suture through the tissue sequentially. It may be beneficial to form a loop of suture around a tissue or tear in a tissue. Thus, the device may be configured to pass a first end of the suture and then (without removing the suture from the tissue) pass the second (opposite) end of the suture at a different location on the tissue, thereby forming a loop of suture which can be tied off by tying the ends of the suture (suture bights) to each other or to a device after they've been passed.

Thus, in general, described herein are suture passer devices having a bent or bendable first jaw extending from an elongate body, and a second jaw that is independently axially slideable relative to the elongate body (and/or first jaw) to form a distal-facing opening between the first and second jaws into which target tissue may be held and sutured by extending a tissue-penetrator (e.g., needle) between the first and second jaws. As discussed above, these devices may be configured to pass a suture multiple times through the tissue (e.g., passing both first and second ends of a suture) to create an entire loop of suture around a tissue such as a torn meniscus. Further, this device may be adapted for use with loops, snares, baskets and other suture passing aids.

The devices described herein may be adapted to include an indicator (e.g., optical indicator) showing where the tissue penetrator (e.g., needle) of the suture passer will pass through a tissue and/or will engage with the opposite (e.g., upper) jaw of the suture passer. In some variations, the suture passers describe herein are adapted so that the lower jaw moves axially both independently, e.g., to retract/extend for positioning around a target tissue, and in conjunction with closing of the jaws, e.g., upper jaw motion, around tissue so that the needle extending from the lower jaw contacts with the upper jaw in a predictable fashion.

Also described herein are suture passers that provide a tactile and/or audible feedback to the user when the tissue penetrator element is extended (e.g., fully extended).

Also described herein are suture passers that have extremely low profiles. In some variations the devices are adapted so that the lower jaw has a substantially lower profile by reducing the arc of the needle exit, by axially separating the lower jaw into a first (e.g., proximal) region controlling the axial translation (motion) of the lower jaw and a second (e.g., distal) region that contains all of the features of the tissue penetrator pathway; these different regions may have different heights, allowing nesting into the shaft particularly near the proximal end of the device.

Although this disclosure is divided up into parts, indication different features, any of these parts or individual features may be used alone or in combination with any other parts or features described herein or incorporated by reference.

In general, the first or second jaw may hold the tissue penetrator within an internal passage, and the tissue penetrator may be extended between the distal-facing opening to push and/or pull a suture between the first and second jaws. The tissue penetrator may be any appropriate material, but shape memory materials (e.g., shape memory alloys, plastics, etc.) are of particularly interest. The tissue penetrator may have a sharp (e.g., pointed, beveled, etc.) distal tip for penetrating tissue, which may be symmetric (e.g., having a central sharp point in the mid-line of the long axis) or asymmetric (having a sharp point that is not in the mid-line of the tissue penetrator). The tissue penetrator may be biased (e.g., pre-bent) in a curve or bend. In general the tissue penetrator (e.g., needle) may extend from a side region of the first or second jaw, extend across the distal-facing opening, and connect to an opening on the side region of the opposite (e.g., second or first) jaw from which it extends. This opening may include a suture capture region that holds the suture passed by the tissue penetrator. The suture capture region may be a suture retainer that holds the suture when passed by the tissue penetrator. For example, the suture retainer may be a deflecting or deflectable clamping region, a hook, or the like.

In general, the tissue penetrator may be configured to bend as it extends from the jaw and across the distal-facing opening. For example, the tissue penetrator may be pre-biased to assume a bent or curved configuration as it extends from within a jaw. Thus, the tissue penetrator may extend approximately perpendicular to the side of the jaw housing it. In some variations the jaw includes a tissue penetrator deflection (e.g., ramped) region that helps deflect the jaw. In some variations the jaw housing the tissue penetrator does not include a deflector.

For example, described herein are suture passers for forming a loop of suture around a target tissue, the suture passer comprising: an elongate body extending distally and proximally along a long axis; a first jaw extending from a distal end region of the elongate body wherein the first jaw is bent or bendable at an angle relative to the long axis; a second jaw configured to slide axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw; a tissue penetrator configured to extend across the distal-facing opening between the first jaw and the second jaw to pass a suture there between; and a plate having a keyhole capture region, wherein the keyhole capture region comprise a capture pathway including a channel extending through the plate and a release pathway, wherein the capture pathway is connected to the release pathway by at least one bend, further wherein the plate is coupled to the first jaw so that it may receive a suture from the tissue penetrator extending from the second jaw. The capture pathway may comprise an opening mouth at an edge of the plate that tapers to a narrower channel before the release pathway. In some variations, the release pathway comprises an enlarged opening having a larger diameter than the region of the capture pathway adjacent to the release pathway. The bend may be configured to retain the suture immediately after it is passed into the keyhole capture region by the tissue penetrator.

In some variations, the plate is configured as a suture stripper.

The device may also include a suture having an enlarged distal end region configured to be retained by the keyhole capture region, further wherein the diameter of the enlarged distal end region is greater than the diameter of the capture pathway but less than the diameter of a portion of the release pathway. The enlarged distal end region may comprise a knot.

Also described herein are methods of passing a loop of suture around a target tissue, the method comprising: placing a first jaw of a suture passer adjacent to a first side of a target tissue, wherein the first jaw extends from a distal end of an elongate body of the suture passer; extending a second jaw of a suture passer adjacent to a second side of the target tissue to form a distal-facing mouth with the first jaw, wherein the second jaw extends in a distal direction from the distal end of the elongate body of the suture passer; extending a tissue penetrator between the first and second jaws of the distal facing mouth while pushing a capture member connected to a suture with the tissue penetrator; retracting the tissue penetrator without the capture member or suture back between the first and second jaws of the distal facing mouth; repositioning the first and second jaws relative to the target tissue; extending the tissue penetrator between the first and second jaws of the distal facing mouth and capturing the capture member with the tissue penetrator; and retracing the tissue penetrator with the capture member back between the first and second jaws of the distal facing mouth.

The step of placing the first jaw may comprise placing the first jaw adjacent to the target tissue with the second jaw retracted proximally so that the distal end of the second jaw is adjacent or proximal to the distal end of the elongate body of the suture passer.

In some variations, the step of placing the first jaw comprises bending the first jaw relative to the elongate body.

Extending the tissue penetrator between the first and second jaws of the distal facing mouth while pushing a capture member may include extending the tissue penetrator from the second jaw to the first jaw. Extending a tissue penetrator between the first and second jaws of the distal facing mouth while pushing a capture member may comprise pushing a capture member comprising a flexible loop wherein the suture is connected to the flexible loop, or a plurality of flexible loops. Extending a tissue penetrator between the first and second jaws of the distal facing mouth while pushing a capture member connected to a suture with the tissue penetrator may comprise extending the capture member from a distal end of the first jaw member.

Also described herein are suture passer devices for passing a suture, the device comprising: an elongate body extending distally and proximally along a long axis; a first jaw extending from a distal end region of the elongate body wherein the first jaw is bendable at an angle relative to the long axis; a second jaw having a sharp, tissue penetrating distal tip, wherein the second jaw is configured to be manually slid axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw; a tissue penetrator configured to extend across the distal-facing opening between the first jaw and the second jaw to pass a suture there between; and a cam surface coupled to the second jaw and configured to move the second jaw axially in conjugate motion with bending of the first jaw member. The cam surface may be coupled with a trigger control configured to change the bend angle of the first jaw relative to the long axis. In some variations, the device further includes a control to engage or disengage the camp surface and engage or disengage the conjugate motion.

Also described herein are suture passer device for passing a suture and providing feedback to the user, the device comprising: an elongate body extending distally and proximally along a long axis; a first jaw extending from a distal end region of the elongate body wherein the first jaw is bent or bendable at an angle relative to the long axis; a second jaw having a sharp, tissue penetrating distal tip, wherein the second jaw is configured to slide axially along the long axis distally and proximally relative to the elongate body, further wherein the first jaw and the second jaw form a distal-facing opening when the second jaw is extended distally and wherein the second jaw is retractable proximally so that it does not form the distal-facing opening with the first jaw; a tissue penetrator configured to extend across the distal-facing opening between the first jaw and the second jaw to pass a suture there between; and an audible feedback actuator configured to provide an audible signal when the tissue penetrator is fully extended across the distal-facing opening.

Also described herein are apparatuses and method of operating them that include are devices having a jaw that is adapted to fit into a tight region of the body such as the knee joint, and particularly around the meniscus of the knee. The jaw member (e.g., upper jaw member) may be adapted to be bent (e.g., hinged) relative to a long axis of the (e.g., elongate body of the) apparatus, and may include a proximal region closest to the end of the jaw hinged to the elongate body of the apparatus that is curved on an upper distally-extending surface and is relatively flat on the lower distally-extending surface that contacts the tissue. The flat lower surface may prevent the tissue from being forced out from between the jaws as the upper jaw is closed towards a lower jaw; the curved upper surface may allow the upper jaw member to be positioned easily between the target tissue and a curved bone surface such as the femur (e.g., the head region of the femur).

Tissue penetrators (e.g., needles) may also or alternatively be adapted so that the distal tip region is sharp and tissue-penetrating, and is protected (e.g., shielded or covered) relative to a central loading region that extends longitudinally through the jaw member (e.g., lower jaw member) when the tissue penetrator is retracted into the device prior to being extended. Thus, the sharp distal tip of the needle may be located slightly displaced relative to the middle of the width of the tissue penetrator at the distal end of the tissue penetrator (e.g., offset by between about 1% and about 40% of the midline of the midline of the width of the tissue penetrator, e.g., between about 1%, 2%, 3%, 4%, 5%, 6%, 7%, 8%, 9%, 10%, 12%, 15%, 20%, or 24% and about 25%, 30%, 35%, 40% of the midline of the width of the tissue penetrator).

Any of the apparatuses described herein may include a tissue penetrator that include a distal sharp tissue penetrator region that includes a side opening into a suture retaining region that is located just proximal to the distal tip; the proximal portion of the side opening may be curved towards the proximal end of the tissue penetrator, so that the width of the side opening gradually increases to the overall width of the tissue penetrator as the outer edge of the side opening extends proximally. This configuration may prevent tissue from snagging or catching on this lower (proximal) edge region of the side opening when extending the tissue penetrator distally through the tissue.

As mentioned above, any of the apparatuses described herein may include some or all of the features described and illustrated.

BRIEF DESCRIPTION OF THE DRAWINGS

In FIG. 1C the cartridge is coupled to the suture passer assembly and the lower jaw is fully retracted (thus the cartridge is fully retracted). In FIG. 1D the same suture passer apparatus is shown with the lower jaw extended to form a distal-facing opening between the upper jaw and the lower jaw region of the cartridge.

FIG. 3A shows an example of a suture passer assembly (which may be configured as a reusable/durable suture passer assembly) such as the one shown in FIGS. 1C and 1D without a cartridge attached.

FIG. 3B shows a cartridge (including a lower jaw housing, tissue penetrator, and suture) that is configured to be preloaded and automatically reloading the suture.

FIG. 7A shows an enlarged view of the distal end region of a preloaded and automatically reloadable cartridge such as the one shown in FIGS. 5A-5C.

FIG. 7B shows an enlarged view of the cartridge housing for the preloaded and automatically reloadable cartridge of FIG. 7A.

FIGS. 9A and 9B show side perspective and front views, respectively, of one variation of a releasable hold that may be used with a preloaded and automatically reloadable cartridge; in this example, the releasable hold is configured as a c-shaped clamp that attaches to the tissue penetrator in a predetermined (notched) position, as illustrated in FIGS. 9C and 9D, showing top and bottom perspective views, respectively, or this variation of a releasable hold attached onto a tissue penetrator.

FIGS. 10A and 10B show side perspective and front views, respectively, of one variation of a releasable hold that may be used with a preloaded and automatically reloadable cartridge; in this example, the releasable hold is a c-shaped clamp that may be attached anywhere along the length of the tissue penetrator.

FIGS. 10C and 10D show top and bottom perspective views (respectively) of a tissue penetrator and suture to which this releasable hold has been attached to hold the suture against the tissue penetrator as shown in FIG. 10C.

FIGS. 13A-13G illustrate the operation of a preloaded and automatically reloadable apparatus, passing a first bight of suture, then automatically reloading the tissue penetrator for passing a second bight of suture by automatically applying tension between a second bight that is not on the tissue penetrator and an adjacent end region of the suture that is releasably held by the tissue penetrator.

FIG. 16A shows a bottom perspective view of the underside of a suture passer assembly to which a reloaded and automatically reloadable cartridge may be coupled.

FIG. 16B shows an enlarged view of a keyed coupling region of the suture passer assembly shown in FIG. 16A.

FIG. 16C shows an enlarged view of another region of the underside of a suture passer assembly to which a reloaded and automatically reloadable cartridge may be coupled including a retainer element for retaining and releasing the cartridge.

FIGS. 18A-18E illustrate a method of loading a suture passer with two loops of suture that may be sequentially passed by the suture passer, indicating a pre-loaded (though not necessary automatically reloading) suture passer.

FIGS. 19A and 19B schematically illustrate two variations of suture passers in which both legs of a loop of suture are held on the same side of the jaw of the suture passer.

FIGS. 25A and 25B illustrate another variation of a suture cleat.

In FIGS. 26A-26L, the tissue being repaired corresponds to knee meniscus tissue.

FIGS. 27A-27C show variations of jaws (e.g., second jaws) of a suture passer. The variation shown in FIG. 27A includes a deflection region for deflecting a tissue penetrator at the widest point of the jaw profile.

FIG. 27D shows the variation of FIG. 27A with the tissue penetrator extended. FIG. 27E shows the variation of FIG. 27B with the tissue penetrator extended. FIG. 27F shows the variation of FIG. 27C with the tissue penetrator extended.

FIGS. 29A-29D illustrate one variation of a suture passer as described herein, adapted to pass a suture through the tissue twice without having to re-load.

FIGS. 30A-30I illustrate a variation of a suture passer describe herein, adapted to pass a suture through the tissue twice without having to re-load.

FIGS. 36A-36I show operation and aspects of a suture passer using an expandable capture element.

FIG. 43A shows a section through a "thin" variation of a suture passer.

FIGS. 43B-43D illustrate enlarged views of various region of the suture passer of FIG. 43A.

FIG. 44 shows the distal end region of the suture passer of FIG. 43A.

FIGS. 45A and 45B show portions of the suture passer of FIG. 43A adapted to reduce the height of the device.

FIG. 50A is a schematic view of the distal end or a tissue penetrator having side-opening suture retainer region.

FIG. 50B is a picture of a tissue penetrator such as the one shown in FIG. 50A with the proximal portion of the side-opening into the suture retainer region caught on tissue as the tissue penetrator extends out of the tissue.

FIG. 50C shows a tissue penetrator having a modified proximal portion of the side opening configured to prevent snagging of the side-opening on the tissue.

FIG. 50D shows an enlarged view of the ramp region of the tissue penetrator shown in FIG. 50C.

FIG. 52 illustrates insertion of a suture passer including a pre-loaded cartridge that has a suture with a pre-tied knot pre-loaded into the cartridge into a subject's knee (e.g., for meniscus repair).

FIGS. 53A-53C illustrate one method of operating a suture passer including a pre-loaded and automatically re-loading cartridge holding a pre-tied knot to pass suture through a tissue (e.g., a torn meniscus).

FIGS. 54A-54C illustrate removal of the suture passer shown in FIGS. 53A-53C and tightening of the pre-tied knot to secure the suture tissue.

FIGS. 55A-55E show internal views of the tissue being sutured, using a method similar to that shown in FIGS. 53A-54C.

DETAILED DESCRIPTION

Figure 1A:
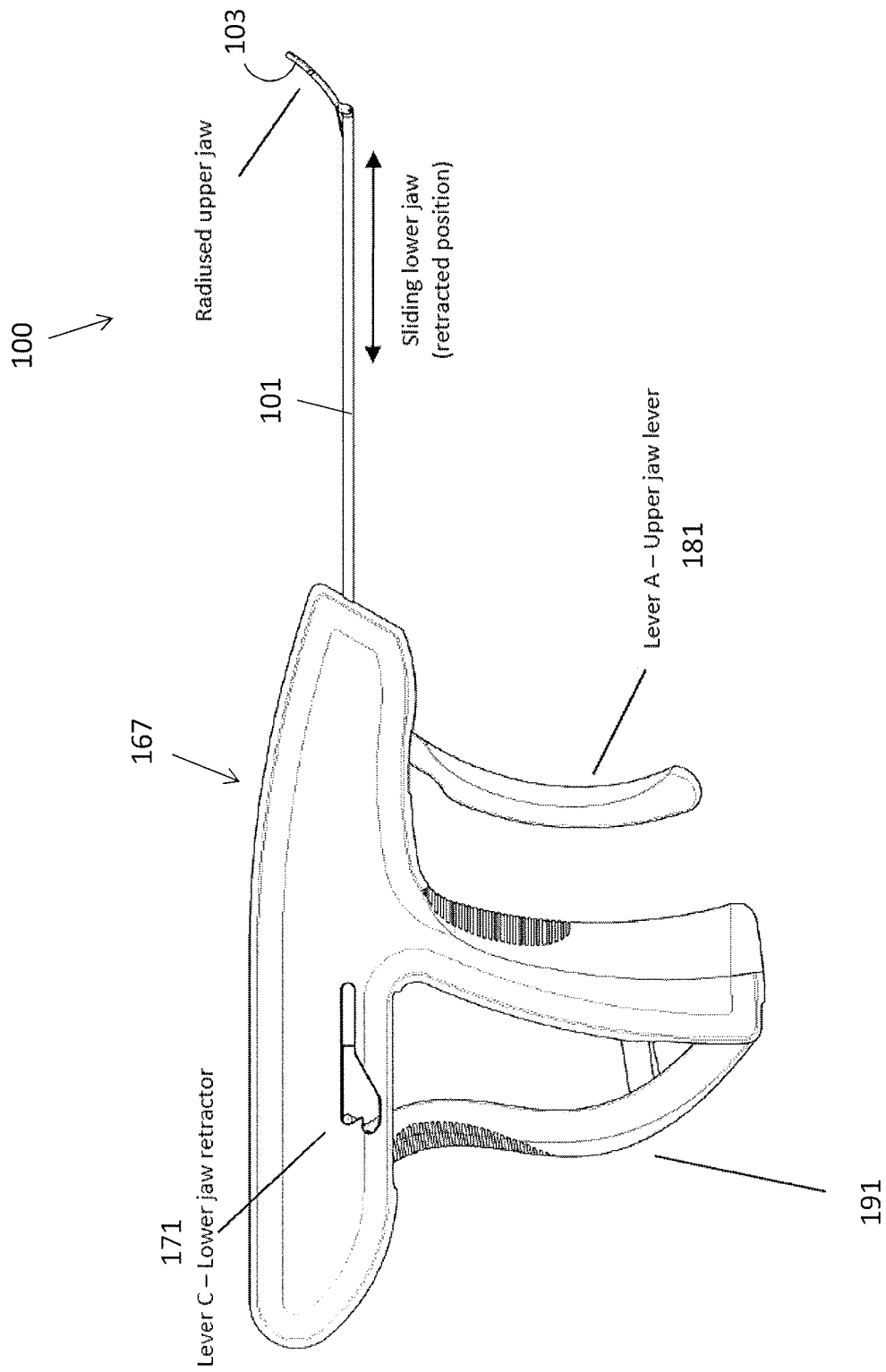
FIG. 1A shows one variation of a suture passer having a bent/bendable upper jaw and a lower jaw that slides axially (distal-to-proximal) in the long axis, with the lower jaw retracted.

In general, described herein are sutures passers, methods of operating them, and methods of repairing tissue using them. These suture passers may be used arthroscopically, and may be used to pass one or more length of suture. These suture passers may include an elongate body and a first jaw member (e.g., first jaw) extending from the distal end of the elongate body, wherein the first jaw is bent or bendable relative to the distal to proximal axis of the elongate body. In some variations the first jaw is hinged near the distal end region of the elongate body. Some variations of the suture passers described herein include a second jaw member (e.g., second jaw) that is configured to slide axially (proximally and distally) relative to the elongate body and/or first jaw. The second jaw may be configured to slide axially sufficiently far proximally so that the distal tip of the second jaw is proximal to the distal end of the shaft (e.g., completely retracted). The first and second jaws may be configured to form a distal-facing opening into which tissue may be held. The suture passers described herein may also include a flexible, bendable, or pre-bent tissue penetrator for passing a suture through the tissue. The suture passer may also include a handle at the proximal end with one or more controls for actuating the first and/or second jaws and the tissue penetrator.

The suture passer described herein may have very narrow (thin) jaws. The tissue penetrator may exit the second jaw from the side of the second jaw and extend across a distal-facing opening to engage an opening in the opposite jaw (e.g., the first jaw), where a suture may be secured and/or released. For example, the suture passers described herein may have a second jaw having a maximum diameter (e.g., maximum height) along the length of the second jaw of less than about 0.11 inches, 0.10 inches, 0.09 inches, 0.08 inches, 0.07 inches, 0.06 inches, 0.05 inches, 0.04 inches, 0.03 inches, 0.2 inches, 0.01 inches, etc. The second jaw may be any appropriate width. For example, the width may be approximately 0.15 inches.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Pre-loaded Suture Passers

Described herein are suture passers and cartridges for suture passers that are preloaded with one, or more preferably, more than one, length of suture that can be passed through tissue by the suture passer without requiring manual loading. In particular, the preloaded suture passers and cartridges for suture passers include a suture holding/tensioning mechanism, which may be referred to as a releasable hold that is connected to, and may ride on, the tissue penetrator ("needle"); the releasable hold releasably secures an end of the suture and provides sufficient tension to load the suture onto the tissue penetrator during operation. A tissue penetrator may also and alternatively be referred to as a needle. A tissue penetrator/needle is generally configured to pierce tissue and pass (push and/or pull) suture. A tissue penetrator may be flat, cylindrical, etc. and may have a square, oval, circular, or other shaped cross-section. The tissue penetrator is generally elongated and may include a notch, eye, hook, or the like for engaging a suture near or at its distal end.

In general, a suture passer device as described herein may be referred to as suture passer and/or a suturing device. Any of the features described herein may be included as part of a low-profile suture passer that includes a pair of jaws (e.g., distal-facing jaws) between which the needle may extend to pass suture. The low-profile suture passers may be configured to allow axial (sliding) movement of a jaw of the suture passer relative to the elongate body of the suture passer; the suture passer may also be configured so that the opposite jaw of the suture passer pivots or rotates relative to the elongate body of the suture passer, so that tissue can be clamped between the jaws before and/or during suturing. Low-profile suture passers having both sliding and rotating jaws may be referred to as dual deployment suture passers, and/or clamping/sliding suture passers.

Figure 1B:
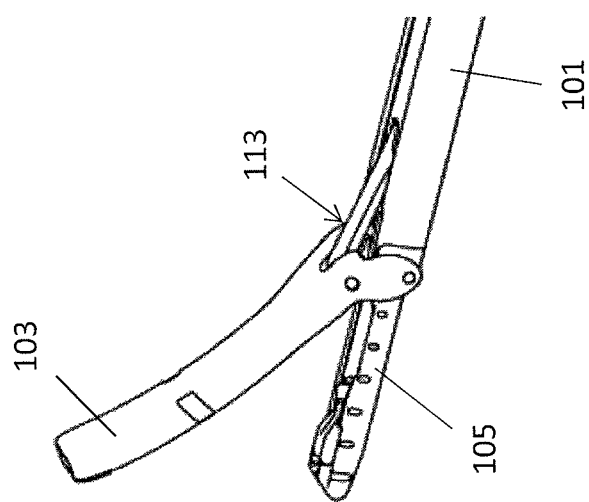
FIG. 1B shows a close-up of the distal end FIG. 1A with the lower jaw extended. The suture passer in FIGS. 1A and 1B may include an integrated preloaded and automatically reloading suture.

For example, a suture passer may generally include a first jaw member and second jaw member that both extend from the end of an elongate body region to form a distal-facing mouth into which tissue to be sutured fits. One or both jaws forming the mouth may be independently moved. FIGS. 1A and 1B illustrate one variation of a dual deployment suture passer 100. In this example, the device has a first (upper) jaw member 103 extending distally from the distal end of a more proximal elongate member 101. A second jaw member 105 (in FIG. 1B) extends distally beneath the first jaw member 103. This second jaw member may slide distally and proximally to retract and extend. A handle 107 is located at the proximal end of the device and includes multiple controls for independently controlling the movements of the first jaw 103, second jaw 105, and tissue penetrator (not shown in FIGS. 1A and 1B, though it may be housed with the tip retracted within either the first or second jaws.

One example of a suture passer that may be configured as a preloaded suture passer is shown in FIGS. 1A and 1B. In FIG. 1A, a first jaw member 103 is held at an angle relative to a long axis of the proximal elongate member 101. The first jaw 103 in this example is curved ("radiused") slightly and connected to the elongate body by a hinge region 113 about which the first jaw 103 may be angled relative to the elongate member 101. In some variations, this hinge region is a pinned hinge; non-pinned (e.g., living hinges) regions may be used. Any appropriate articulating region that allows the first jaw member to move at an angle relative to the proximal portion of the device (e.g., the elongate member) may be used. In some variations, this first jaw member 103 is referred to as an upper jaw member, but alternative variations (in which the first jaw member is a lower jaw member) are also possible.

A jaw lever 181 can be used to move (bend) or hold the first jaw member 103 angle. The first jaw member 103 may be actuated by any appropriate mechanism, including a tendon member (e.g., push rod, pull rod, or the like), and may be held (locked) at any angle (e.g., between 0° and 180° relative to a line extending from the distal end of the elongate body, between about 0° and 90°, between about 0° and 60°, etc.). In some variations the device has a neutral position during which no force is applied to the controller to move the first jaw member, so that the first jaw member is angled "open" (e.g., at 30°, 45°, 50°, 90° or at any angle between about 15° and about 90°) relative to the elongate body; actuating (e.g., pressing) the control on the handle results in the first jaw member moving towards the "closed" position (e.g., reducing the angle with respect to a line extending from the distal end of the elongate body). In some variations the jaw member is in the neutral position when angled with 0°/180° relative to the elongate body.

The first jaw member 103 shown in FIGS. 1A and 1B also includes a suture retainer region near the distal end. A suture retainer can hold a suture that has been passed into the suture retainer from the tissue penetrator. This suture retainer region may include a grasper, a pair of graspers, a deflectable member into which the suture may be pushed and held (e.g., handed off from the tissue penetrator), or the like. For example, the retainer may be a leaf spring element that is displaced by the tissue penetrator as it enters the jaw member in variation in which the tissue penetrator is housed in/behind the lower (sliding) jaw.

The second jaw 105 is shown in FIG. 1B as a lower jaw member. In this variation, the lower jaw 105 is configured to slide proximally towards and into the proximal elongate body 101 of the device (as shown in FIG. 1A). The second jaw 105 typically moves axially, in the direction of the proximal-distal axis of the suture passer. The second jaw member 105 may move axially completely past the distal end of the elongate body; alternatively, the second jaw member 105 may slide axially in the proximal direction only partially (e.g. to align with the hinge region of the first jaw member). The suture passer may be configured so that the second jaw 105 can retract completely into, and extend out of, the lower portion of the elongate body 101. A control (e.g., retractor lever) 171 on the handle 107 can be used to trigger retraction of the second jaw member 105 while another control (e.g., lower jaw/needle lever) 191 can be used to extend the second jaw 105. In FIGS. 1A and 1B, the lower jaw/needle lever is configured to both extend the lower jaw when squeezed once, and to extend and retract the tissue penetrator (needle) when squeezing the lever a second time; squeezing the second time extends the needle and releasing the lever retracts the needle.

A tissue penetrator (not visible in FIGS. 1A and 1B) may be housed within or behind the second jaw 105. Alternatively, the suture passer may be configured so that the tissue penetrator is housed within or behind the upper jaw and the suture retainer region is on the opposite (e.g., lower) jaw. The tissue penetrator may be configured as a needle, wire, knife, blade, or other element that is configured to extend from within either the first or second jaw members and across the opening between the jaw members to engage a suture and push the suture through the tissue from a first jaw (e.g., the lower jaw) where it can be held by the suture retainer region on the opposite jaw (e.g., the upper jaw). In general, the tissue penetrator may be configured to completely retract into the housing of the second jaw member 105. It may be extended across the opening between the jaws by actuating a member in the handle to push or otherwise drive (slide) it out of the jaw and deflect it across the opening, and though any tissue held between the jaws. In FIG. 1A and 1B, the second jaw member 105 completely houses the tissue penetrator and includes a deflection region that drives the tissue penetrator up and out of the second jaw member by deflecting it across the opening between the two. The jaw/needle lever 191 can be used to extend the tissue penetrator (for example, a first squeeze can advance the second jaw member 105 and once the lower jaw is extended, an additional squeeze or squeezes can extend the needle.

A suture passer, such as the suture passer described in FIGS. 1A and 1B, can be configured to be preloaded with suture for multiple passes. This can be performed either with a replaceable cartridge or by configuring the lower jaw of the suture passer to include a suture having a first bight (e.g., bend, loop, etc.) region, a second bight region, a tissue penetrator holding the first length (bight) of suture, a suture holding region holding the second bight, and a releasable hold on the suture passer that drives the second bight region from the holding region to re-load the tissue penetrator after the first bight has been passed.

For example, a suture passer apparatus as described herein may be configured to operate with cartridge (e.g., a preloaded cartridge). In general, the preloaded cartridge may be part of a replaceable assembly that is preloaded with suture; the preloaded cartridge engages with a durable assembly including components of the suture passer that can be re-used, while the cartridge includes "disposable" components (e.g., suture, tissue penetrator) that are consumable, and/or limited-use.

In general, a cartridge may include one of the jaw members of a suture passer, such as the lower jaw, the suture, and the tissue penetrator, as well as a releasable hold that re-loads the suture into the tissue penetrator after it has been passed. A cartridge may also include a housing that completely or partially covers the suture and tissue penetrator. The housing may also include a storage region (e.g., capsule) for holding the length(s) of suture, and any additional suture management components (e.g., funnels, channels, spools, etc.) for guiding the suture. As mentioned above, in some variations a removable, replaceable and/or releasable cartridge is not used, but the entire suture passer may be preloaded with suture and disposable after use.

In some variations of the cartridge described herein the cartridge is preloaded with suture and a tissue penetrator and engages with a durable suture passer body. The reusable or durable suture passer body may be referred to as a durable portion or durable assembly of a suture passer apparatus. In general, the durable portion may include an elongate body, a first jaw member (e.g., pivoting, bent, bendable, or fixed), and a handle including controls for controlling movement of the jaw(s) and tissue penetrator. The replaceable cartridge portion may be referred to as a cartridge assembly, and typically includes a housing attached to or forming all or part of a (e.g., second) jaw, a tissue penetrator (e.g., needle) and a suture. The suture is typically both preloaded into the tissue penetrator and may also be "primed" for loading a second length into the tissue penetrator after the first length has been passed from the tissue penetrator.

For example, the second jaw member 105 can be part of a suture cartridge that is configured to hold at least two preloaded loops of suture to be passed. Further, as described in more detail below, the suture cartridge can be configured to attach to and detach from the rest of the apparatus (e.g., to the durable assembly portion of the suture passer).

Figure 1C:
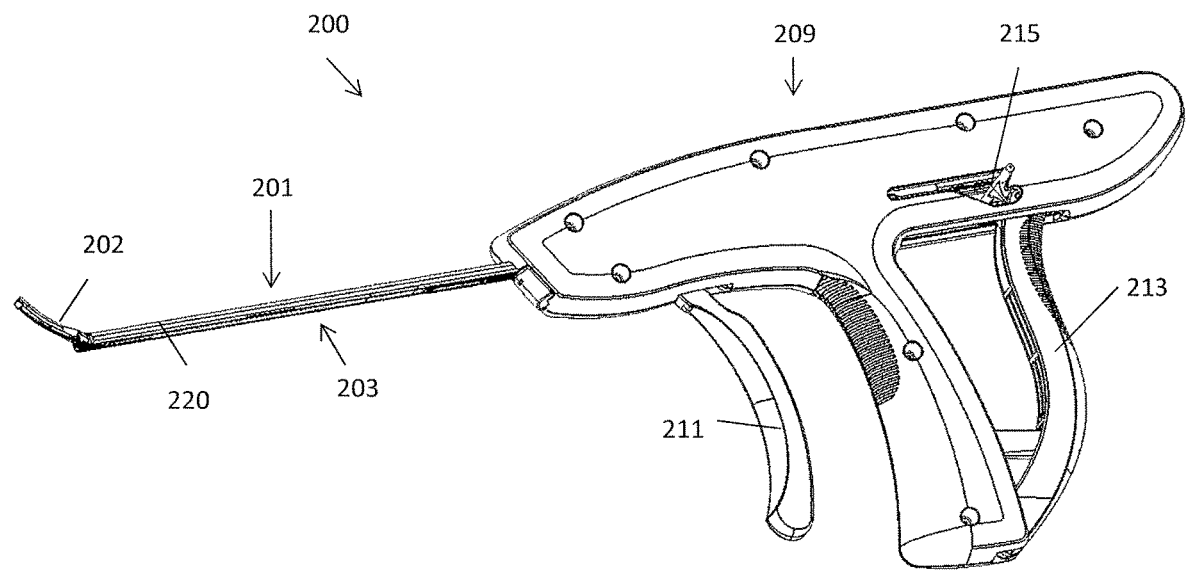
FIGS. 1C and 1D show side perspective views of an example of a suture passer apparatus formed of a reusable/durable suture passer assembly including the upper (pivoting) jaw, elongate body and handle with controls, to which a preloaded and automatically reloading cartridge forming the lower jaw assembly has been attached.
Figure 1D:
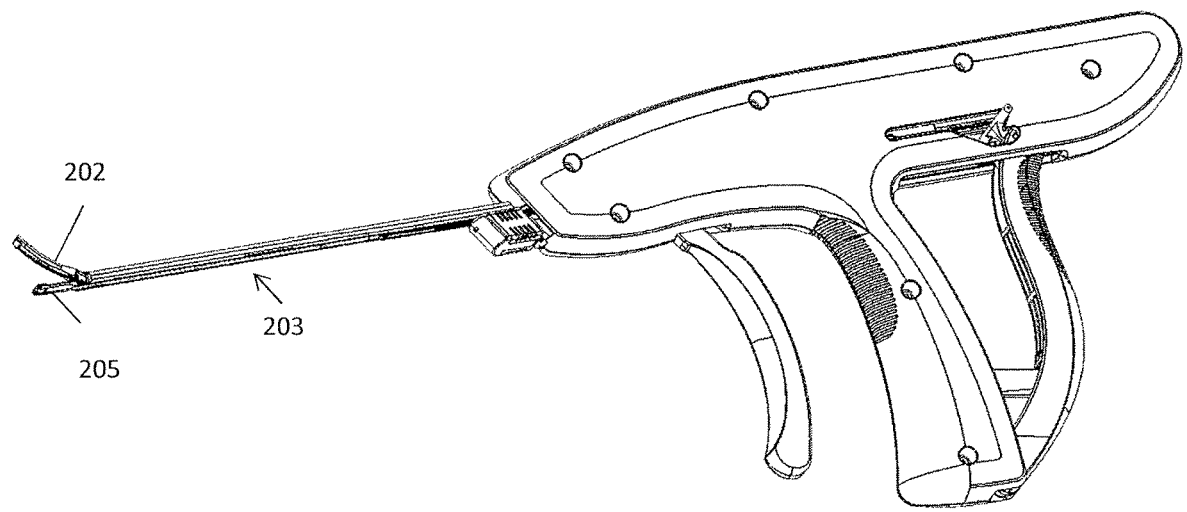
Figure 2:
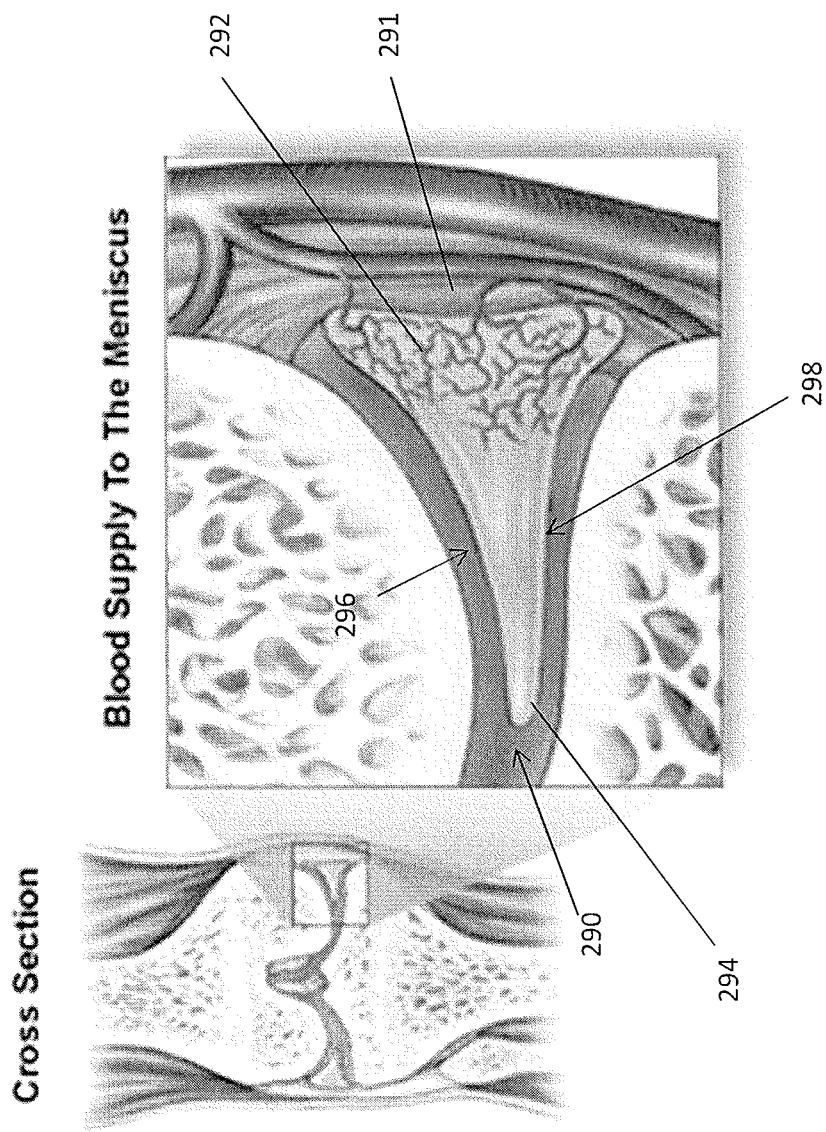
FIG. 2 illustrates the anatomy of the meniscus, including the capsule and associated vascular tissue.

FIGS. 1C and 1D illustrate a suture passer 200 that is configured as a clamping/sliding suture passer, having both a sliding lower jaw 205 and bending/pivoting upper jaw 207, where the lower jaw is formed as part of a preloaded cartridge 203. In FIG. 1C the durable assembly 201 and the replaceable cartridge assembly 203 are combined to form the suture passer 200. When combined, the operation of the device may be controlled as described above. The handle 209 includes a first control (upper jaw or bending jaw control) 211 for controlling the angle of the upper jaw 202, a second control (e.g., jaw extending/needle extending control) 213 for controlling extension of the lower jaw and extension/retraction of the tissue penetrator, and a lower jaw release 215 control that retracts the lower jaw after it has been extended. In FIGS. 1C and 1D, the lower jaw is part of the cartridge assembly and in FIG. 1C is shown retracted proximally relative to the elongate shaft 220 of the apparatus. In FIG. 1D, the lower jaw 205 is shown extended distally relative to the long axis (e.g., the distal-to-proximal axis of the elongate body 220); this may be achieved by actuating (e.g., squeezing) the second control to extend the entire cartridge 203 and therefore the lower jaw region 205 distally. When extended distally the upper 202 and lower 205 jaws form a distal-facing opening across which a tissue penetrator (not shown) may be extended from the cartridge to pass the preloaded suture.

FIG. 3A illustrates one embodiment of a durable assembly 300 of a suture passer, without the attached cartridge shown in FIG. 3B. In FIG. 3A, the durable assembly includes the upper jaw 302, an elongate body 320, and a handle 330 with controls. The durable assembly is adapted for releasably coupling with a preloaded cartridge, such as the one shown in FIG. 3B. For example the durable assembly may include one or more keyed regions to which a cartridge may be coupled. The cartridge may therefore include complementary regions for engaging the durable assembly. An example of how a cartridge may be engaged with a durable assembly to form the suture passer is described in greater detail below.

Figure 3C:
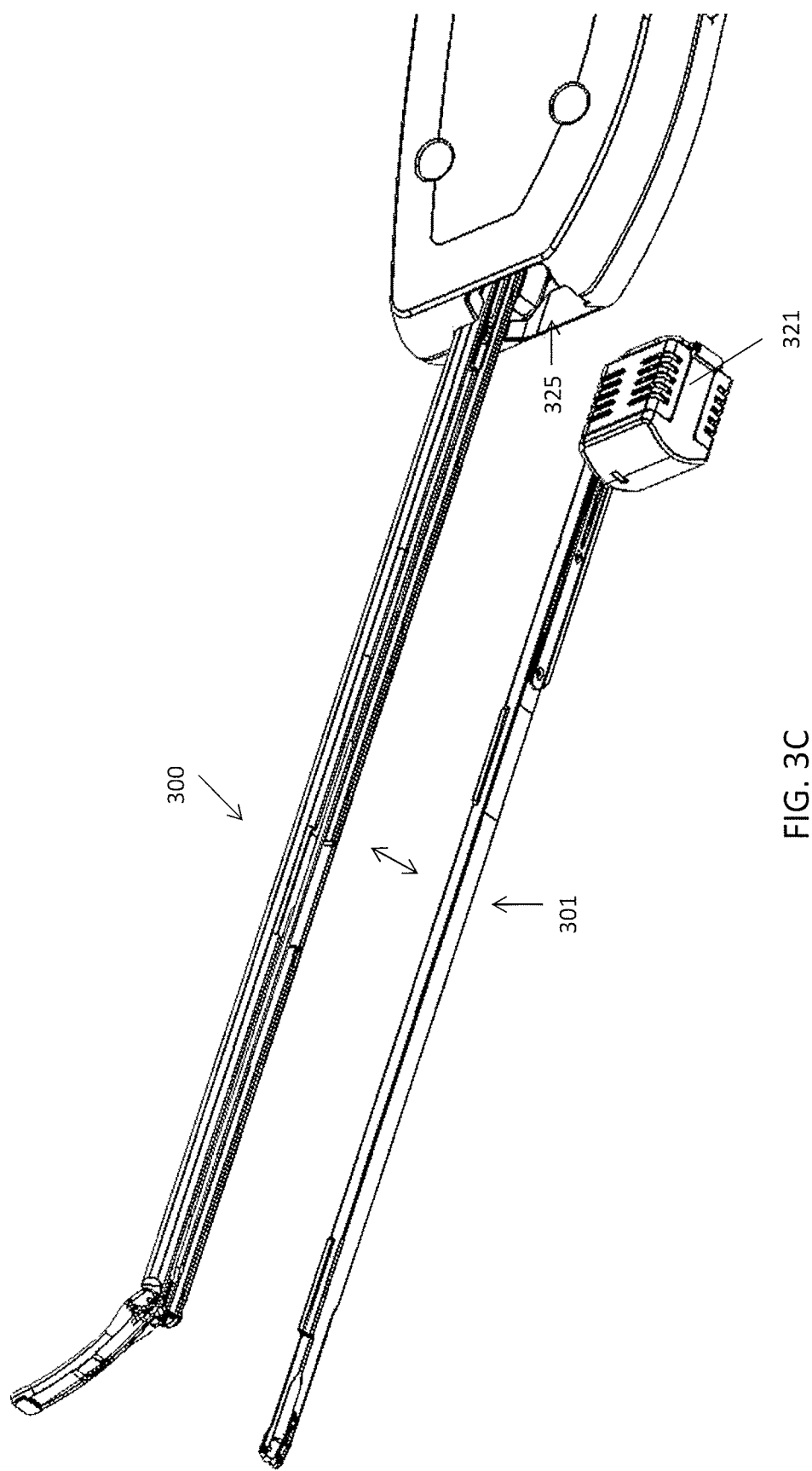
FIG. 3C shows the suture passer assembly of FIG. 3A being coupled to the cartridge of FIG. 3B.

FIGS. 3B and 3C show perspective views of a cartridge 301 that includes a jaw (lower jaw) region 305 and a housing 309 that at least partially encloses a suture, tissue penetrator, suture holding region and releasable hold on the tissue penetrator. In this example, the housing includes a lower jaw region 305, an elongate region 319, and a suture capsule 321. The suture capsule stores at least a portion of the suture to be passed. In some variations a single long (e.g., 2 inches, 3 inches, 4 inches, 5 inches, 6 inches, 7 inches, 8 inches, 9 inches, 10 inches, 12 inches, 13 inches, 14 inches, etc.) length of suture may be used to form both a first bight region and a second bight region that are separately passed by the device and loaded automatically and/or preloaded into the tissue penetrator by the cartridge. The first bight may be at one end region and the second bight may be at the other end region. As indicated in FIG. 3C, the cartridge 301 may be connected and disconnected from the durable assembly 300. Thus, in operation a new preloaded cartridge 301 may be connected to a durable assembly 300, the device may be used (e.g., to pass two lengths/bights of suture) and the assembly may be removed and a fresh (preloaded) cartridge attached. The used cartridge may be refurbished (e.g., by replacing the suture and/or the tissue penetrator), reloaded, recycled, or otherwise disposed of. A portion of the cartridge may be inserted into the durable assembly. For example, in FIG. 3C, the suture capsule region 321 may be retracted into a portion 325 of the handle when the lower jaw is retracted proximally.

The elongate body 101 shown in FIGS. 1A-3C is illustrated as a relatively straight, flattened and cylindrical structure, though other shapes may be used. For example, the elongate body may be curved, bent, or angled. In some variations the elongate body is configured to be bent, curved or angled dynamically (e.g. by changing the bend or curve).

The elongate body of the suture passer (which may include both the elongate body region of the durable component and/or the elongate body portion of the cartridge that can mate with the durable component) may be any appropriate length. For example, the elongate body may be between about 6 and about 24 inches long, e.g., 6 inches long, 8 inches long, 10 inches long, 12 inches long, etc. The suture passers described herein may be used for arthroscopic surgeries and therefore may be dimensioned for use as such. Thus the diameter of the device may be configured to be small enough for insertion into a cannula, tube or the like for insertion into the body.

Figure 4A:
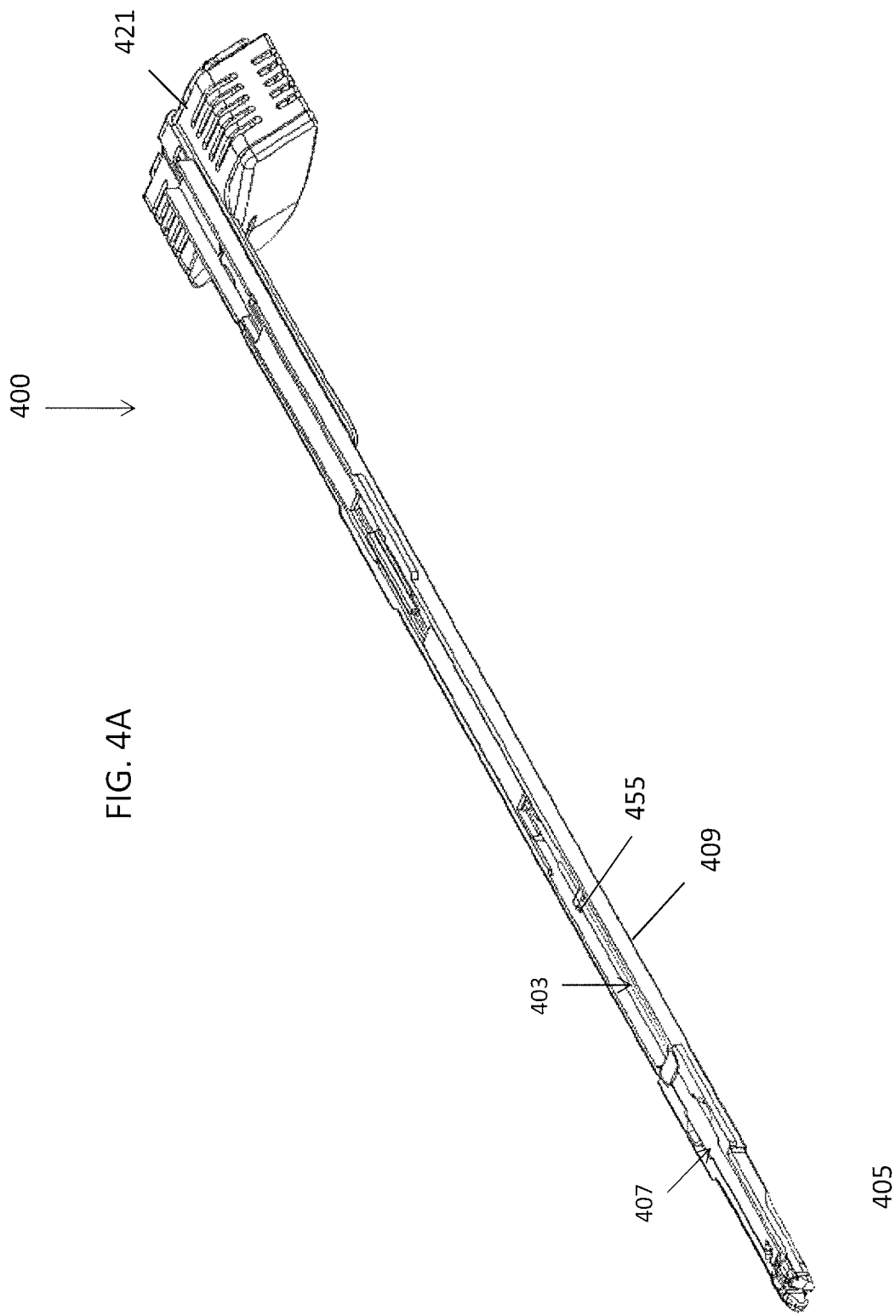
FIG. 4A shows an enlarged isometric view of one example of a pre-loaded and automatically reloading cartridge.

In general, a suture can be preloaded in a suture cartridge 1000 for use in automatically and sequentially passing two or more lengths of suture with a suture passer, such as the suture passers of FIGS. 1A-1B or 1C-1D. FIG. 4A illustrate a variation of a suture cartridge 400 configured to be used as part of a suture passer that can hold and pass two lengths of suture. As mentioned, the suture cartridge 400 can be configured to attach and detach from a durable assembly of a suture passer. The suture cartridge 400 in this example includes a lower jaw 405 (i.e. similar to the lower jaw 105 of FIGS. 1A and 1B) as well as a suture storage capsule 421.

The lower jaw 405 can include a housing 409 that encloses a tissue penetrator 403 and first and second bights. A track can run within the housing 409 of the cartridge along which the tissue penetrator 403 can slide when moving within and/or extending in and out of the cartridge. The track can be sized such that the tissue penetrator 403 fits within the track but prevents the suture from engaging in the track. A suture holding region (not visible in FIG. 4A) may be formed between the housing (e.g., the track) and the tissue penetrator, for holding the second bight region of suture. A top cover 407 can be placed over a distal portion of the housing which may help retain the ends of the suture(s), including the bight regions, in a correct position within the cartridge.

Figure 4B:
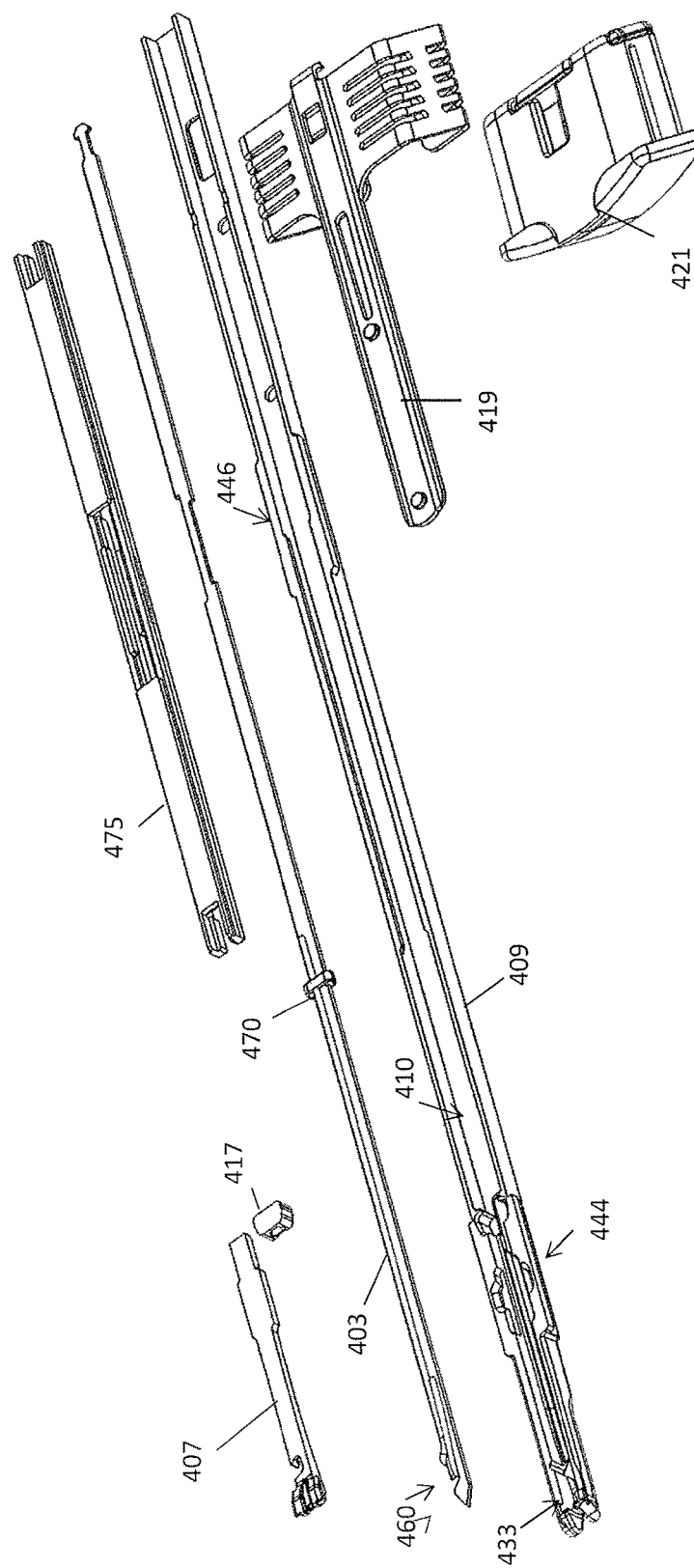
FIG. 4B shows an exploded view of the cartridge of FIG. 4A.

FIG. 4B shows an exploded view of the cartridge shown in FIG. 4A. The cartridge may be assembled to include the housing 409, which may be referred to as a jaw housing or lower jaw housing. A suture holding region (suture capsule 421) may be integral with the jaw housing or separate from it, but is attached so that the suture can continue from the jaw housing to the suture holding region. If the holding region 421 is separate from the jaw housing 409, a connection tab 419 may be attached over the housing at the proximal end of the cartridge and may secure the holding region to the rest of the housing. The inner region 410 of the housing may be configured to hold the suture and tissue penetrator, and also to allow the tissue penetrator to slide within and out of the housing. For example, the inner region 410 of the housing may include a distal deflector (ramp) region 433. The housing 409 may also include the engagement regions such as extending structures (posts, flanges, etc.) that may be keyed to complementary engagement regions on a durable assembly to secure the durable assembly and the cartridge together. In FIG. 4B, two sets of flanges or keyed regions 444, 446 are shown.

A suture 460 and tissue penetrator 403 may also fit within the cartridges lower jaw housing. In FIG. 4B, the suture is shown coupled to the tissue penetrator so that a first bight is preloaded into a notch region forming a suture engagement region of the tissue penetrator. A second bight at the second end of the same suture is held to the side of the tissue penetrator and the end region of the suture distal from the second bight region is coupled to the tissue penetrator by a releasable hold 470 configured as a clasp in this example. The tissue penetrator may be coupled to a sled (e.g., needle sled) 475 that is also held within the jaw housing. As described in detail below in some variations a separate releasable hold is not required; for example the sled may be configured to include the releasable hold (see, e.g., FIG. 11A). A needle sled may act to couple the tissue penetrator to a push/pull rod in the durable component for actuating the needle. The lower jaw housing may also include a cover (e.g., top cover) 407 over all or a portion of the jaw housing, such as the distal end region. Additional suture management regions may also be included, such as a funnel 417 that can be used to guide the suture within the housing, and help prevent it from tangling within the housing or getting pinched between a wall of the housing and the needle.

Figure 5A:
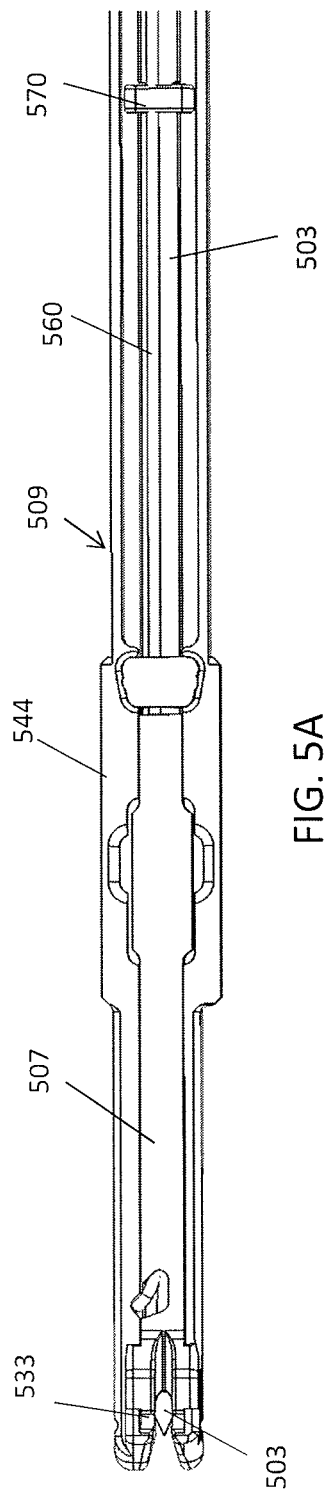
FIGS. 5A-5C show top, side perspective and side views, respectively, of the distal end of a preloaded and automatically reloadable cartridge such as the one shown in FIG. 4A.
Figure 5B:
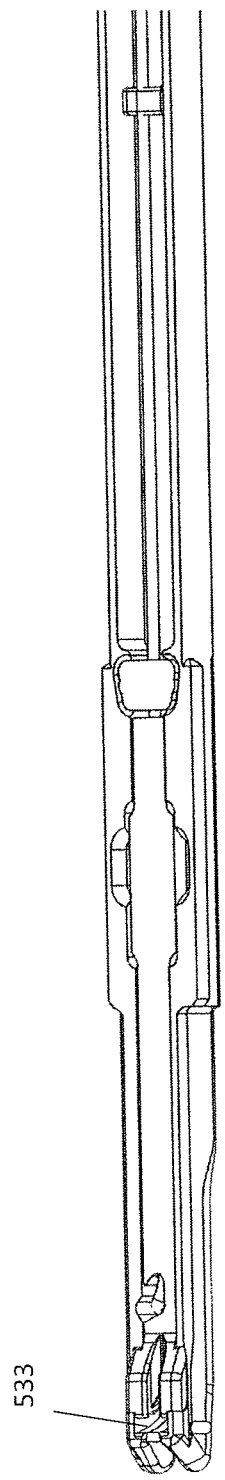
Figure 5C:
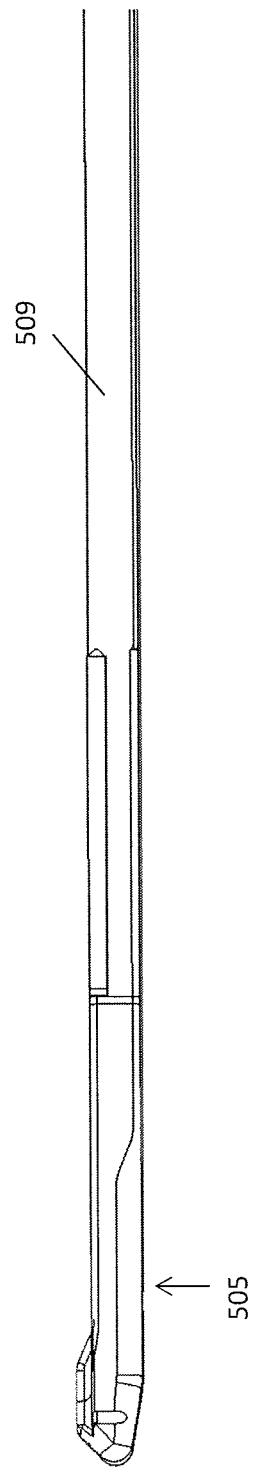

FIGS. 5A-5C show additional detail of a variation of an assembled cartridge such as the one shown in FIG. 4A. In FIG. 5A, a top view of the distal end region of the assembly shows a housing 509, top cover 507, and tissue penetrator 503. A releasable hold 570 is coupled to the tissue penetrator, holding a distal end region of a suture 560. The housing includes a flanged region 544 to engage with a durable assembly of a suture passer, and a ramped deflection region 533 to direct the tissue penetrator laterally from the cartridge.

Figure 6:
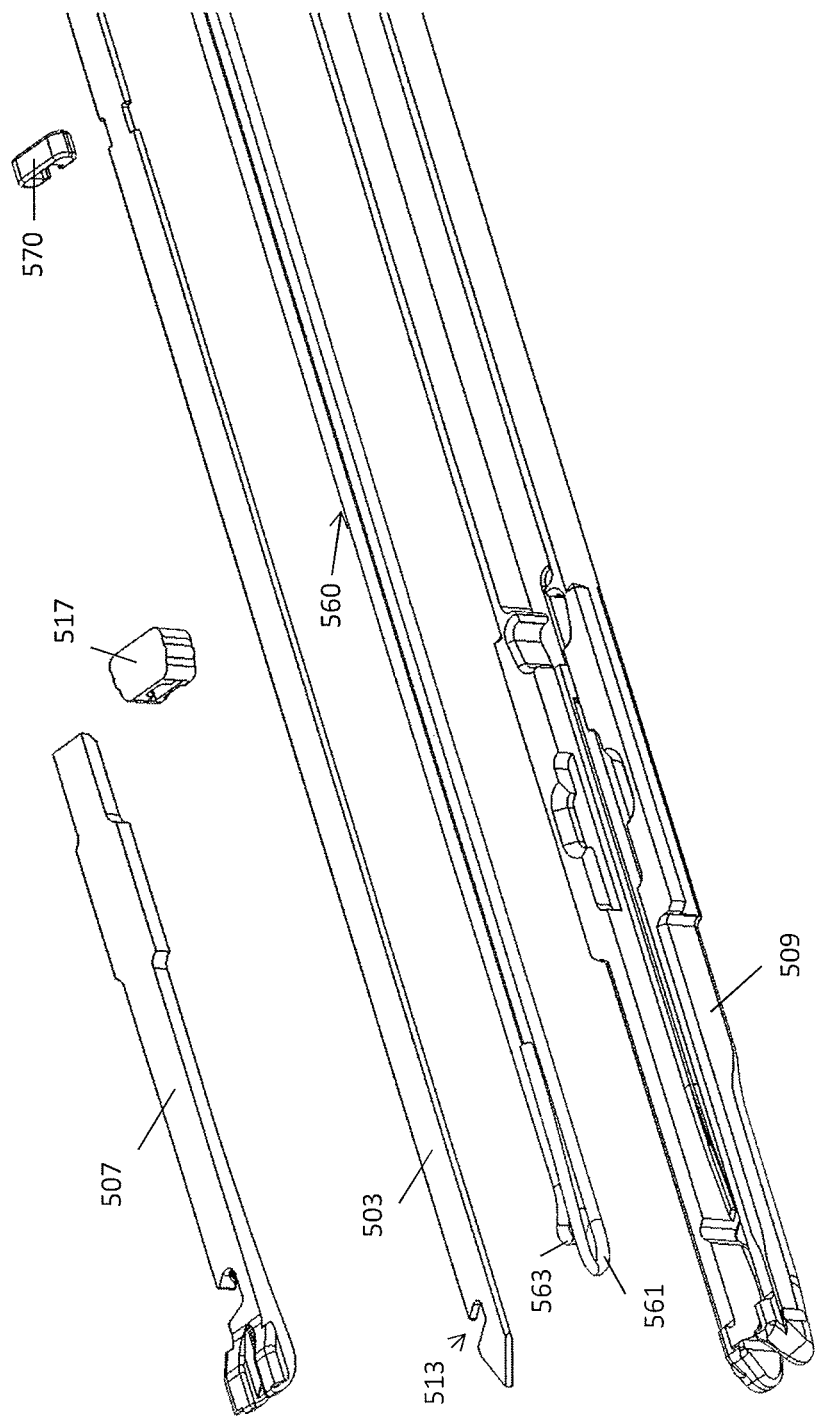
FIG. 6 is an exploded view of a distal end region of one variation of a preloaded and automatically reloadable cartridge.

FIG. 5B shows a side perspective view and FIG. 5C shows a side view. As can be seen in FIG. 5B, the cartridge, and particularly the lower jaw region 505 is thin and relatively flat. FIG. 6 is an enlarged and exploded view of the distal end of the cartridge, showing the housing 509, a suture 560 (including a first bight region 561 and second bight region 563), tissue penetrator 503 (including suture engagement region 513), a releasable hold (clasp 570), top cover 507, and suture management element (funnel 517).

Similarly, FIGS. 7A and 7B show a top view of the distal end region of a cartridge. In FIG. 7A a top cover has been made removed to show how the bights and end regions of the suture engage with the tissue penetrator within the cartridge. As shown in FIG. 7A, the first bight 761 of suture is held in the suture engagement region 713 of the tissue penetrator. A tissue penetrator generally retains a suture so that the suture can be pushed (or, in some variations pulled, or pushed and pulled) through the tissue by the tissue penetrator until it is held by a suture retainer on the opposite jaw. For example, in FIG. 7A, the tissue penetrator includes a notched region forming the suture engagement region 713; the notch is oriented at an angle relative to the length of the tissue penetrator, directed proximally, so that the suture is retained within the tissue penetrator as it is advanced distally. Other suture engagement regions may be used, including distal-facing suture engagement regions, or the like.

In FIG. 7A, a single suture forms the first and second bight regions; the portion of the suture between the first bight 761 and the second bight 763 runs behind the tissue penetrator (not visible in FIG. 7A), between the tissue penetrator and the jaw housing 709. The second bight region 763 on the opposite end of the suture is held in a suture holding region 722 that is off of the tissue penetrator, while the distal end region of the suture just distal to the second bight region 763 is secured to the tissue penetrator by the releasable hold (not visible in FIG. 7A, but see, e.g., FIG. 5A). The suture holding region 722 in FIGS. 7A and 7B is a notched region formed within the jaw housing laterally positioned relative to the tissue penetrator, and on the same side of the tissue penetrator as the opening into the suture engagement region 713 of the tissue penetrator 703. In operation, the suture holding region holds the second bight until the suture engagement region of the tissue penetrator is empty (e.g., of a bight of suture).

As used herein, a bight or bight region of suture refers to a length of suture. The length of suture forming the bight may be bent or looped; for example, the bight region may be bent so that the suture bends 180 degrees, as illustrate din FIG. 7A and FIG. 7C, discussed below. In some variations the bend forming the bight may prevent the suture from sliding or pulling distally or proximally.

Returning now to FIG. 8, a tissue penetrator may include any needle. In FIGS. 5A-7A and FIG. 8, the needle is a flat, elongated length of shape memory alloy (e.g. Nitinol) that is superelastic; however, other materials and shapes may be used. For example, a needle may be cylindrical, have a round or oval cross-section, etc. Although it may be beneficial to use a superelastic material such as a shape memory alloy, because the cartridge may be configured to deflect the needle a small number of times, the needle may be formed of other plastics and/or metals capable of passing through the tissue (e.g., having sufficient column strength to be pushed through the tissue).

Figure 8:
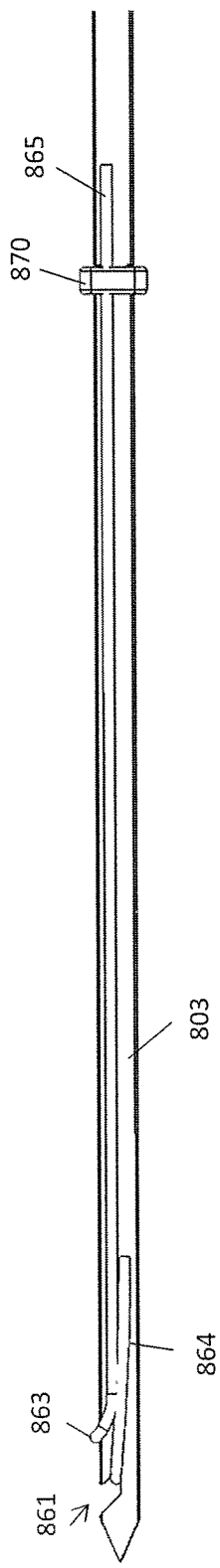
FIG. 8 shows a tip view of one example of a tissue penetrator holding a first bight of suture in a suture engagement region, where the suture also include a second bight region that can be held in a suture holding region so that it doesn't move with the tissue penetrator, although the distal end region of the suture near the second bight is held on the tissue penetrator by a releasable hold so that this end of the suture moves with the tissue penetrator.

In FIG. 8, the suture is shown on the tissue penetrator 803, so the end of the suture 864 near the first bight 861 extends on the same side of the tissue penetrator 803 as the distal end region 865 of the second bight 862. The distal end region 865 of the suture closest to the second bight region 863 is held against the tissue penetrator (fixed to the tissue penetrator) by the releasable hold 870, which is positioned proximally down the length of the tissue penetrator from the suture engagement region and the first and second bights.

As will be described in greater detail below, the releasable hold acts to secure an end region of the suture to the tissue penetrator in a predetermined position. The releasable hold is releasable because it is configured to release the end region of the suture from the tissue penetrator when a pull force on the suture is greater than a threshold release force. When the pull force on the suture exceeds the release force, the suture may be drawn out of the releasable hold; until that point, the releasable hold prevents the suture end region from being released.

Any appropriate releasable hold may be used. The release hold may be a mechanical hold (e.g., clamp, an O-ring, a clip, a clasp, a friction releasable hold, a band, a crimp, etc.), a frangible hold (e.g., a wax hold, releasable adhesive, etc.), or the like. For example, FIGS. 9A-9D illustrate one variation of a releasable hold configured as a clasp that is secured to a predetermined portion of the tissue penetrator. FIG. 9A shows a side perspective view of the releasable hold. The hold includes a channel that fits over a cut-out region of the tissue penetrator 903, as shown in FIGS. 9C and 9D in top and bottom perspective views, respectively. An example of the cut-out region 910 into which a releasable hold such as the one shown in FIG. 9A-9D may fit is shown in FIG. 6. The cut-out region may prevent the releasable hold from sliding or migrating on the tissue penetrator during operation. In some variations the releasable hold may be affixed (e.g., glued, welded, etc.) to the tissue penetrator.

In some variations, such as the releasable hold shown in FIGS. 10A-10D, the releasable hold does not engage a cut-out region, but may secure to a tissue penetrator even where a notched or cut-out region is not included. For example the releasable hold may be allowed to slide if forces acting on the releasable hold exceed a threshold level (releasable hold sliding threshold). In FIG. 10A, the releasable hold is configured as a clamp 1001 that may secured over the tissue penetrator 1013 and lock down onto the tissue penetrator.

FIGS. 10C and 10D also illustrate the releasable hold engaging and securing a distal end region of a suture 1005. On the opposite side of the tissue penetrator, the elongate portion of the suture between the first and second bights 1088, 1088' extends under the tissue penetrator and past the releasable hold without being retained by the releasable hold.

In some variations the releasable hold is formed as part of another portion of the apparatus that is attached and moves with the tissue penetrator, such as a coupler coupling the tissue penetrator to an actuator. Thus a separate releasable hold is not necessary. In some variations the releasable hold comprises a sled (needle sled) that is adapted to releasable hold an end region of suture to the tissue penetrator. For example, FIGS. 11A-11D illustrate a variation in which the releasable hold is configured as a sled that also couples the tissue penetrator to an actuator, for example, when the cartridge is coupled with a durable suture passer.

Figure 11A:
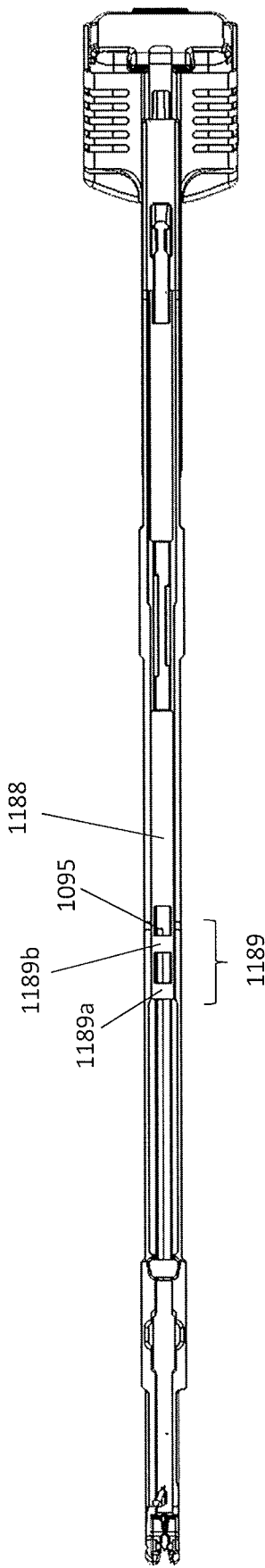
FIG. 11A is another variation of a preloaded and automatically reloadable cartridge from a top view. The reloadable cartridge includes a sled (needle sled) configured as the releasable hold.

FIG. 11A shows a top view of a cartridge (or lower jaw assembly) in which the releasable hold is formed by the sled 1188. In FIG. 11A, the releasable hold comprises a region 1189 at the distal end of the sled having two clasp portions that form a narrow gap through which the end region of the suture 1195 passes. The suture end 1195 is pinches between the tissue penetrator 1199 and a first releasable hold region 1189a and a second releasable hold region 1189b. Thus, a separate releasable hold element is not needed.

Figure 11B:
FIG. 11B is a top perspective view of the releasable sled from the variation shown in FIG. 11A.
Figure 11C:
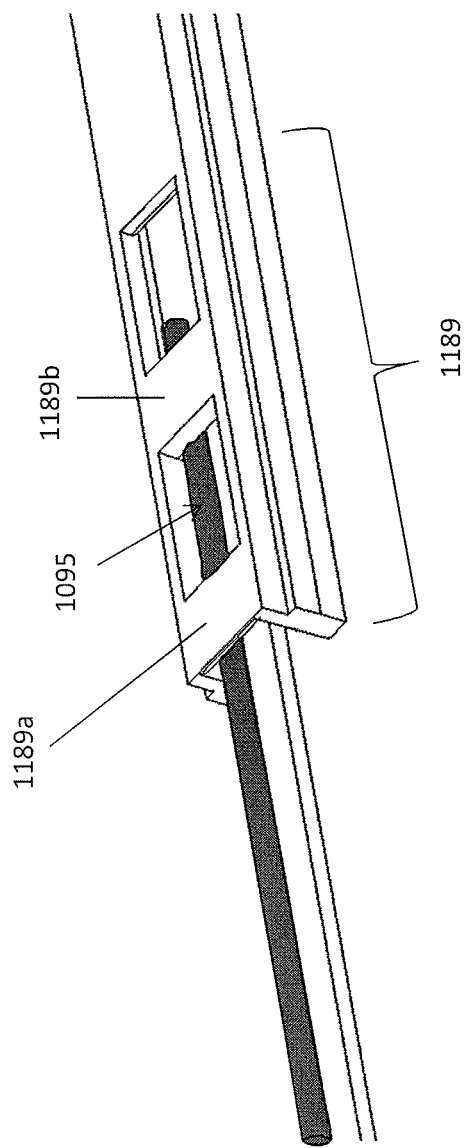
FIG. 11C shows the releasable hold region of the sled, where the sled is connected to a tissue penetrator and is holding an end region of a suture against the tissue penetrator.
Figure 11D:
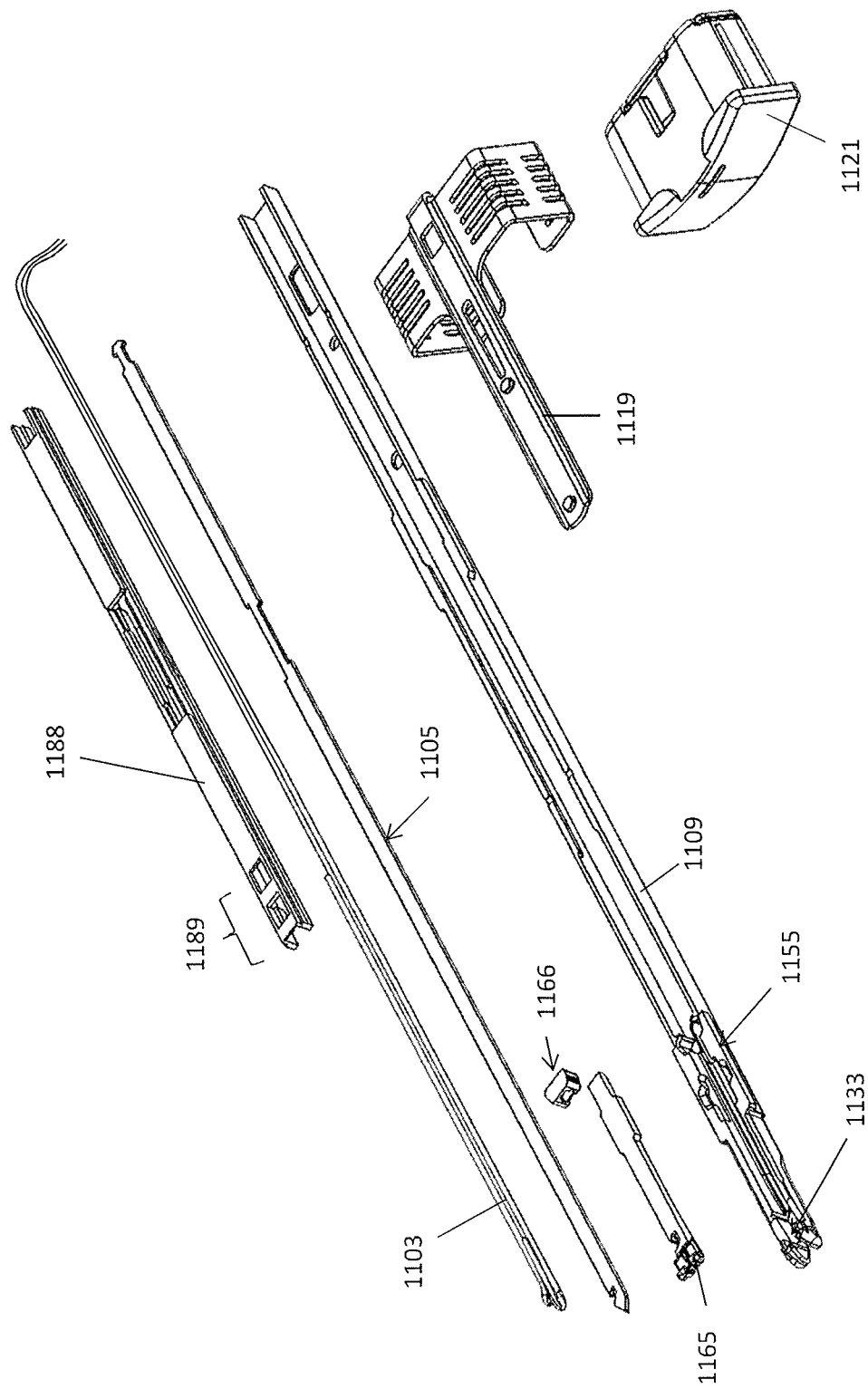
FIG. 11D is an exploded view of another variation of a preloaded and automatically reloadable cartridge including a sled integrated with a releasable hold for securing an end of a suture to the tissue penetrator so that the tissue penetrator may be automatically reloaded with a second bight of suture after passing a first bight of suture.

FIG. 11B the sled 1188 is shown removed from the lower jaw assembly. The sled includes an internal track region into which the tissue penetrator may be inserted. The distal end of the sled, as shown in greater detail in FIG. 11C, is adapted to form a releasable hold. The releasable hold compresses the end region of the suture 1095 between a first surface on the sled and the upper surface of a tissue penetrator held within the sled. In some variations the tissue penetrator is deflected slightly by the sled so that it curves/bends upwards slightly at this releasable hold region to hold the suture within releasable hold. In FIGS. 11A-11C the releasable hold region of the sled forms two retaining surfaces 1189a and 1189b in the sled so that there are two contact points retaining the suture, pinching the suture end between the tissue penetrator (which is coupled to the sled) and the distal end of the sled. In some variations the sled includes a single contact region forming the releasable hold. FIG. 11D shows an alternative exploded view of a cartridge in which the releasable hold is configured as a distal portion of the needle sled. The cartridge includes a housing 1109, which may be referred to as a jaw housing or lower jaw housing. A suture holding region (suture capsule 1121) may be integral with the jaw housing or separate from it, but is attached so that the suture can continue from the jaw housing to the suture holding region. If the capsule 1121 is separate from the jaw housing 1109, a connection tab 1119 may be attached over the housing at the proximal end of the cartridge and may secure the holding region to the rest of the housing. The inner region of the housing 1109 may be configured to hold the suture 1103 and tissue penetrator 1105, and also to allow the tissue penetrator to slide within and out of the housing. The inner region of the housing may include a distal deflector (ramp) region 1133. The housing 1109 may also include the engagement regions such as extending structures (posts, flanges 1155, etc.) that may be keyed to complementary engagement regions on a durable suture passer assembly to secure the durable suture passer assembly and the cartridge together. A top cover 1165 and funnel (suture guide) 1166 may also be included. In FIG. 11D, the sled 1188 includes the releasable hold (region 1189), as discussed above.

Figure 7C:
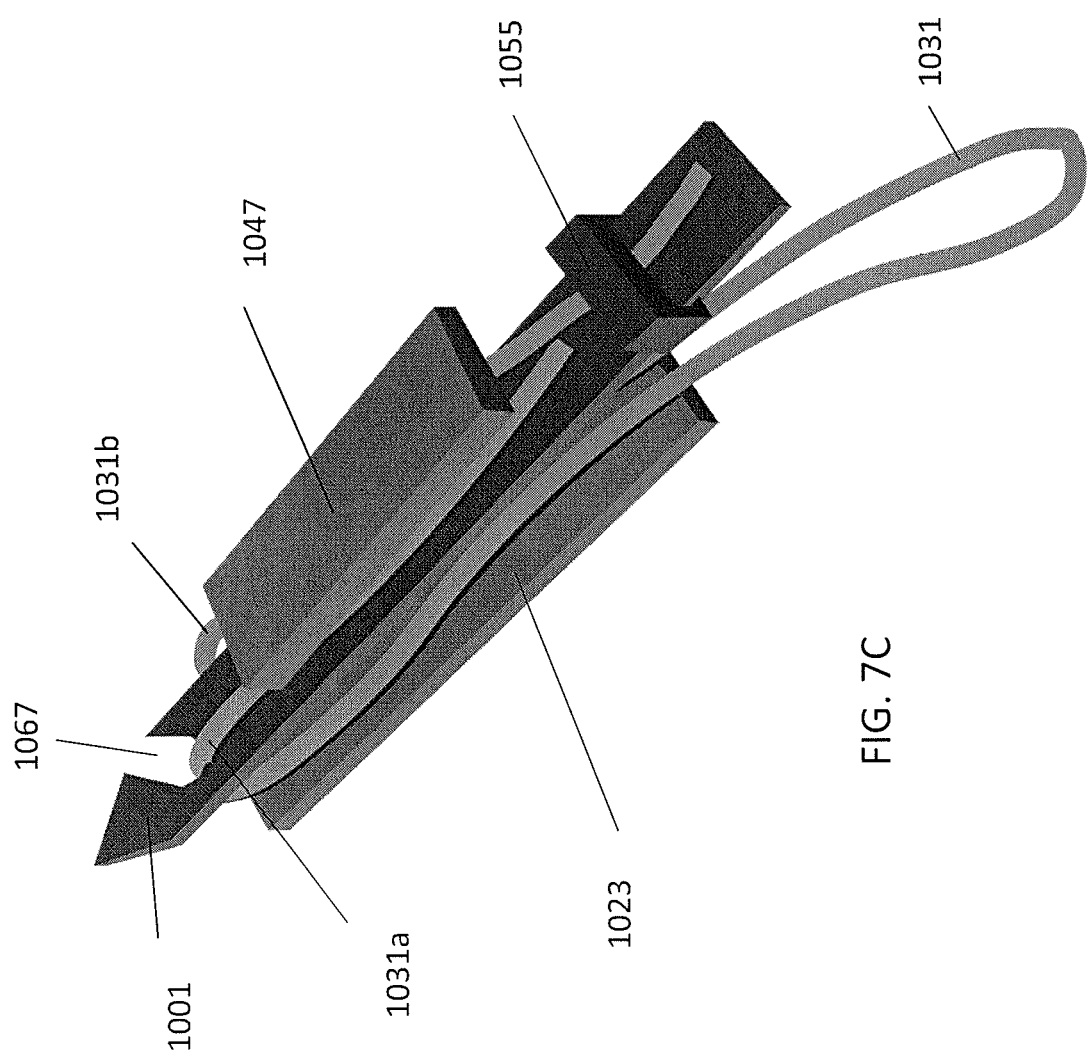
FIG. 7C is a partial perspective view, with some of the components removed or made partially transparent, showing the relationship between the tissue penetrator, suture and releasable hold, lower jaw housing, and top of one variation of a preloaded and automatically reloadable cartridge such as the one shown in FIGS. 7A and 7B.
Figure 12A:
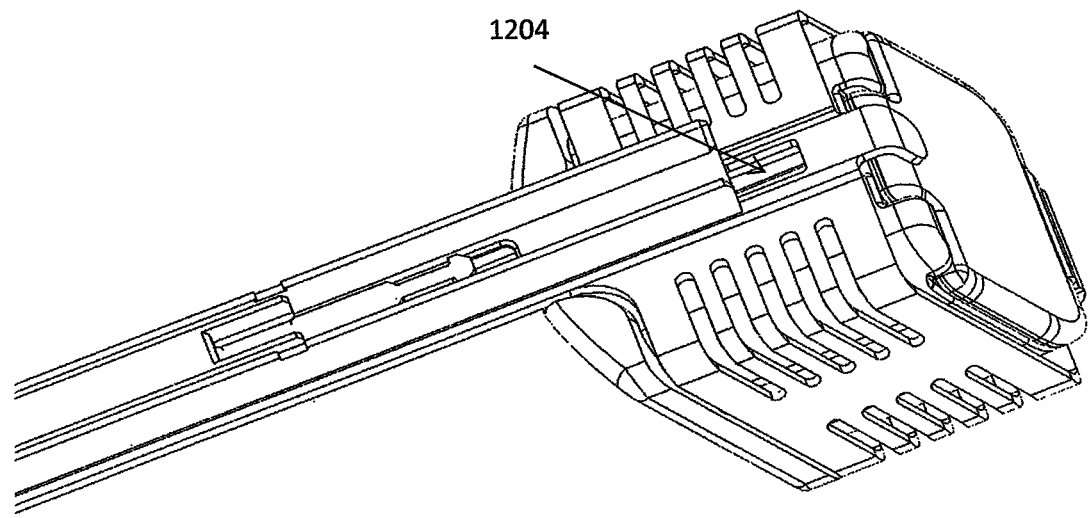
FIGS. 12A-12C illustrate side perspective, top and side views, respectively of a proximal end of a preloaded and automatically reloadable cartridge including a suture holding region (capsule).
Figure 12B:
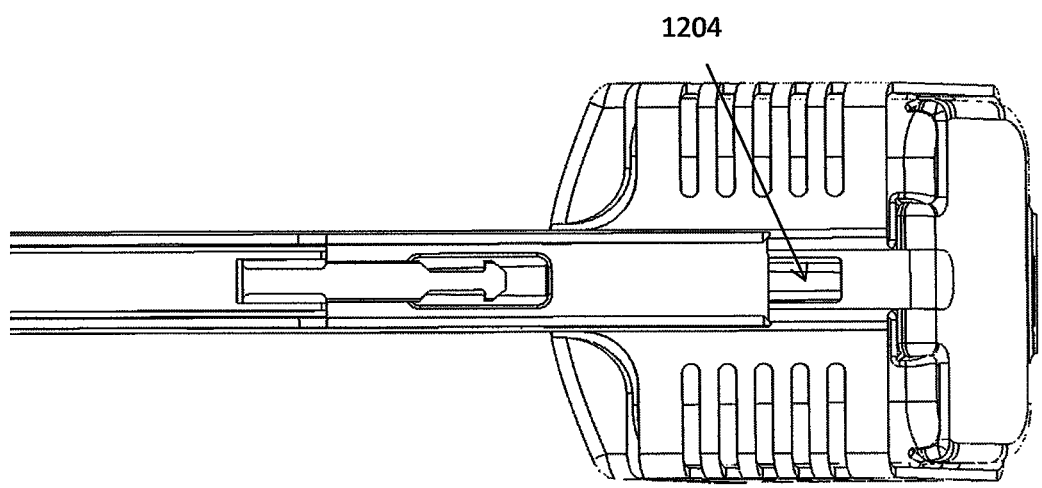
Figure 12C:
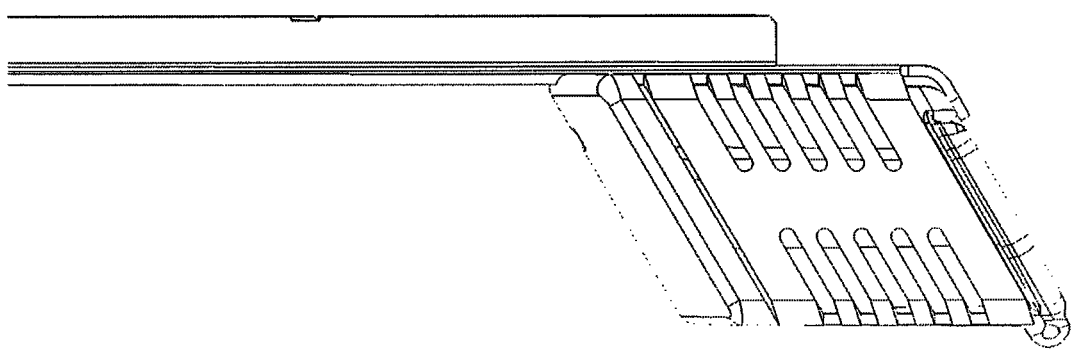

Returning now to FIG. 7C, FIG. 7C illustrates the relationship between the distal end of a tissue penetrator 1001 and a suture. In this example, as discussed above, the first and second bight regions 1031a, 1031b are be opposite ends of a single long suture strand 1031. As mentioned, in some variations more than one suture may be used (e.g., a first suture forming the first bight, a second suture forming the second bight, etc.). In FIG. 7C, the first bight region 1031a (i.e. the loop that will be passed first during use) extends through, and is held in place by, the notch 1067 forming the suture engagement region in the tissue penetrator 1001. The second bight region 1031b (i.e., the loop that will be passed second during use) is held in a suture holding region (not visible in FIG. 7C). The end of the suture closest to the second bight is secured to the tissue penetrator 1001 by a releasable hold 1055 (show configured as a clasp). The first bight region 1031a of the suture 1031, when preloaded, can thus wind such that the end of the suture nearest the first bight is located between the top cover 1047 and the tissue penetrator 1001. The body of the loop (bight 1031a) extends through the notch 1067 to the bottom of the housing 1023, runs between the tissue penetrator 1001 and the bottom of the jaw housing 1023, and the intermediate portion of the suture between the first bight 1031a and the second bight 1301b extends along the length of the jaw member and into a suture storage region of the housing (e.g., suture capsule not visible in FIG. 7C). In FIG. 7C, this intermediate portion is not shown to scale, it may be longer than indicated. For example, the intermediate portion may be 2 inches, 3 inches, 4 inches, 5 inches, 6 inches, 7 inches, 8 inches, 9 inches, 10 inches, 12 inches, 13 inches, 14 inches, etc. The intermediate portion of suture may be loosely held, so that it may be withdrawn out of the housing relatively easily after passing the first and/or second bight. FIGS. 12A-12C illustrate perspective, top and side views, respectively, of a suture storage region (suture capsule) that may be located at the proximal end of a cartridge, which may hold some of this intermediate portion of the suture(s). The body of the suture 1031 can then be wound or otherwise stored. The second bight region 1031b extends from the suture storage region, runs between the tissue penetrator 1001 and the bottom of the housing 1023, and extend into a suture holding region (e.g., notch) formed in the housing between the housing 1023 and the tissue penetrator 1001. The end of the suture distal to the second bight then extends between the top cover 1047 and the tissue penetrator 1001 and is held tight by the releasable hold (clasp 1055). For convenience, the suture may be considered to run from proximal (near the first bight) to distal (near the second bight).

As mentioned above, the releasable hold can attach to the tissue penetrator 1001 and apply tension to the second bight 1031b. For example, the releasable hold may be a suture clasp 1055 that pins the suture to the tissue penetrator. The releasable hold 1055 is typically configured to travel with the tissue penetrator 1001 as the penetrator 1001 moves axially. As the tissue penetrator slides distally and proximally, the second bight region of the suture remains in approximately the same location (relative to the jaw housing of the cartridge), while the end of the suture connected to the second bight and pinned to the tissue penetrator by the releasable hold moves distally and proximally with the tissue penetrator. When the second bight region is held in the suture holding region in the jaw housing, as the tissue penetrator extends distally (as when passing a bight region of suture between the jaws), the tension on the end of the suture between the second bight region and the releasable hold is decreased (producing a "slack" region); when the tissue penetrator is extended proximally (as when retracting the tissue penetrator into the jaw housing), the tension on the second bight region and the region of suture between the second bight region and the releasable hold is increased. This increased tension on the second bight tends to draw the second bight proximally; if the tissue penetrator is withdrawn proximally to a position where the suture engagement region of the tissue penetrator is aligned with the suture holding region, and the suture engagement region is empty, the suture will be drawn into the suture engagement region. If the suture engagement region is occupied (e.g., by another suture bight), the second suture bight will remain in the suture holding region.

The automatic reloading of the second bight of suture onto the tissue penetrator using the releasable hold (and suture holding region) is illustrated in FIGS. 13A-13G, showing a suture cartridge sequentially passing both a first bight region of suture 1031a, and a second bight region of suture 1031b automatically (i.e., without having to reload the needle). For example, referring to FIG. 13A, the suture 1031 can be preloaded into a cartridge or suture passer so that the first bight region 1031a extends through the suture engagement region 1067 of the tissue penetrator 1001, and the second suture bight region 1031b extends around the tissue penetrator 1001 at the notch 1045 in the jaw housing 1043 adjacent to the tissue penetrator, and an end region of the suture (the end region closest to the second bight region) is secured to the tissue penetrator 1001 with the releasable hold (clasp 1055).

In FIG. 13B, the tissue penetrator 1001 preloaded with the first suture bight 1031a is moved (e.g., slid) axially forward/distally as shown by the arrow. As the tissue penetrator 1001 drives forward to deliver the first loop (bight 1031a) between the jaws to the opposite jaw where it will be held by a suture retainer, the second bight region 1031b stays in place relative to the tissue penetrator 1001 in the suture holder region (notch 1045) while the end of the suture 1035 moves with the tissue penetrator due to the clasp 1055. The second bight 1031b stays in the notch 1045 while the adjacent end region of the suture bunches within the cartridge.

In FIG. 13C, the tissue penetrator 1001 is retracted proximally back into the cartridge after delivering the first bight 1031a of suture. The friction second bight in the suture holder region (notch 1067) holds the second loop region 1031b relatively fixed while the end region 1035 moves proximally away with the tissue penetrator. The suture bight 1031b is thus placed under tension as the region of suture between the second bight and the end of the suture held by the releasable hold is tensioned. As shown in FIG. 13D, as the tissue penetrator 1001 is pulled proximally far enough so that the suture holding region (notch 1045) in the jaw housing and the suture engagement region 1067 in the tissue penetrator align, the second bight region is drawn into the suture engagement region of the tissue penetrator. Because the second bight 1031b is under tension, aligning the notches 1045, 1067 cause the second bight 1031b to slip proximally into the tissue engagement region (notch 1067) in the tissue penetrator, as shown in FIG. 13E.

In FIG. 13E, the second bight 1031b has slipped fully into the suture engagement region 1067 of the tissue penetrator 1001. In FIG. 13F, the tissue penetrator 1001 can again be extended distally to pass suture; before this step, the suture passer may be repositioned on (including retracting the jaw/cartridge, etc.). Extending the tissue penetrator 1001 distally pushes the second bight region between the jaw until it also engages a (or the same) suture retainer region on the opposite jaw. The tissue penetrator may again be retracted, leaving the second bight region in the opposite jaw. In some variation the end 1035 of the suture is pulled out of the releasable hold 1055 when extending the tissue penetrator distally; alternately, the end of 1035 of the suture may be pulled out of the releasable hold 1055 when the lower jaw is retracted. The force required to pull the end region of the suture 1035 out of the releasable hold may be much lower than the force retracting the lower jaw. In general, when the releasable hold is maintained in a fixed position relative to the tissue penetrator, the end region of the suture is withdrawn by withdrawing the needle and/or the jaw housing (and jaw) proximally. Once the end region of the suture 1035 is released, the suture body (in variations in which both bights regions of suture are formed in a single suture) may be pulled distally and out of the cartridge, as shown in FIG. 13G. The entire suture passer may be withdrawn.

As mentioned, the cartridge can be disposable. That is, the cartridge can be designed such that the entire jaw housing (including the tissue penetrator) can be removed from the durable portion of the suture passer and discarded after it is used to automatically pass two loops of suture. Additional cartridges can be used with the suture passer for each additional use. Advantageously, by using disposable cartridges, problems with tissue penetrator wear and/or fatigue can be reduced or eliminated.

Figure 14A:
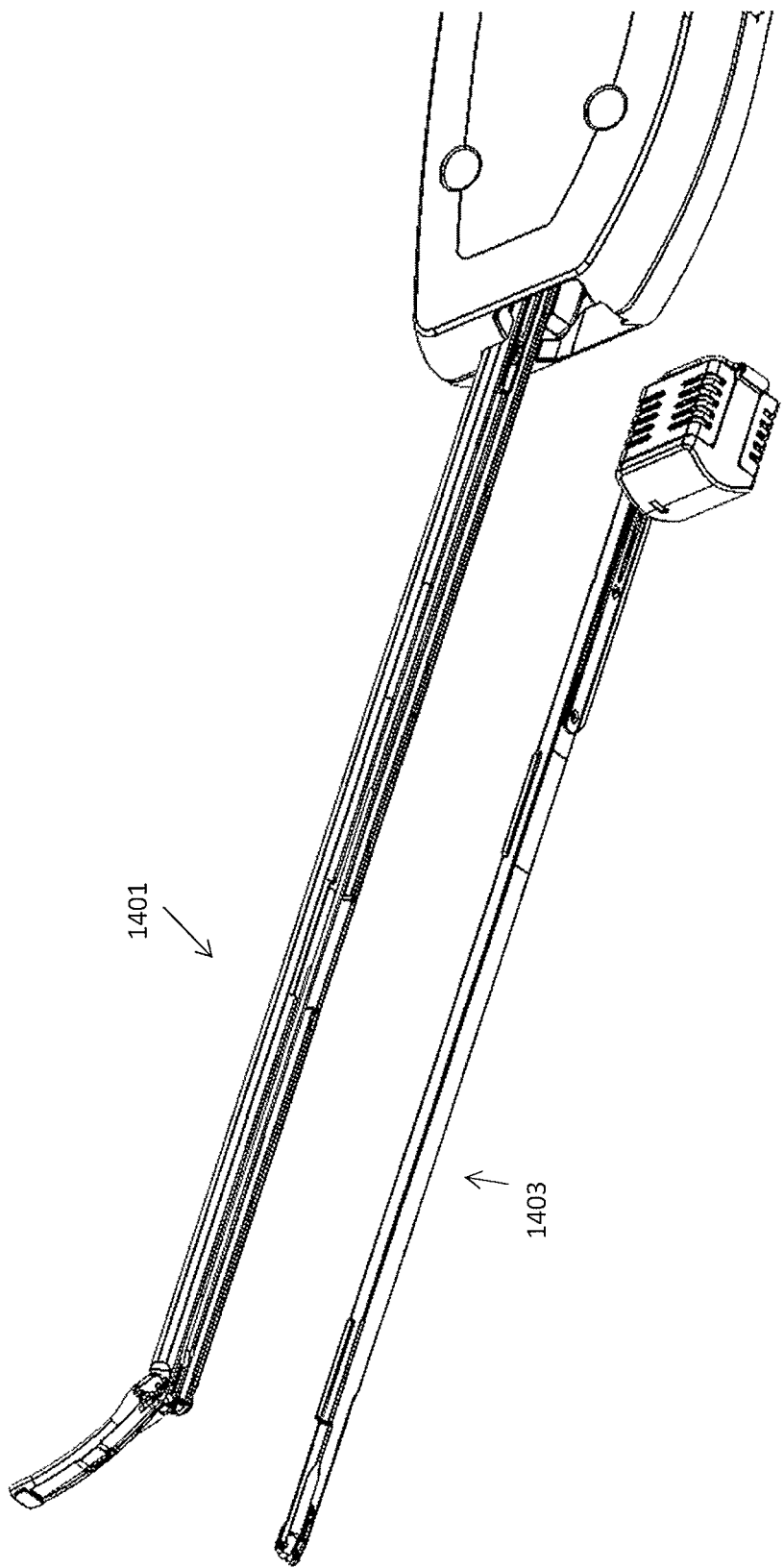
FIGS. 14A and 14B illustrate connecting a preloaded and automatically reloadable cartridge with a suture passer assembly.
Figure 14B:
Figure 15A:
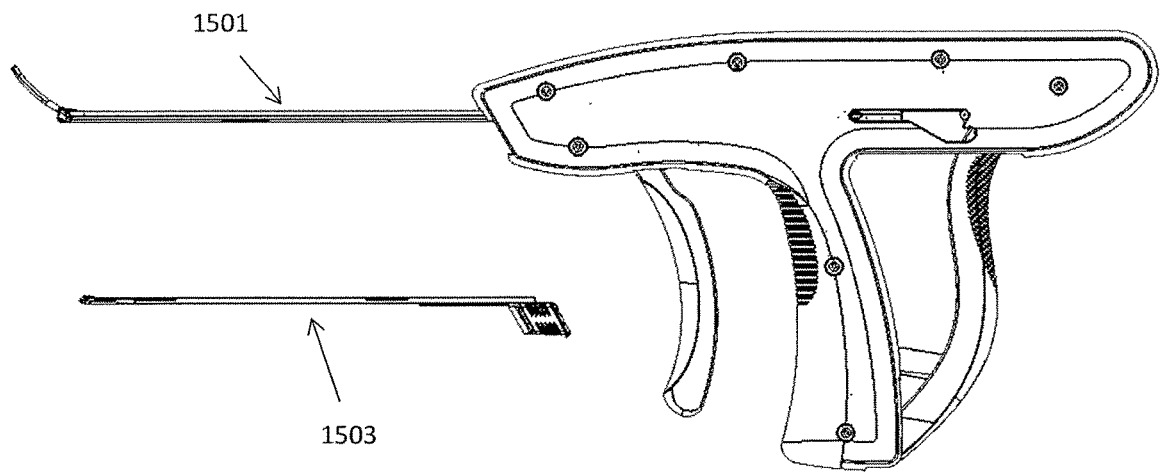
FIGS. 15A-15E show another example of a method of connecting a reloaded and automatically reloadable cartridge to a suture passer assembly.
Figure 15B:
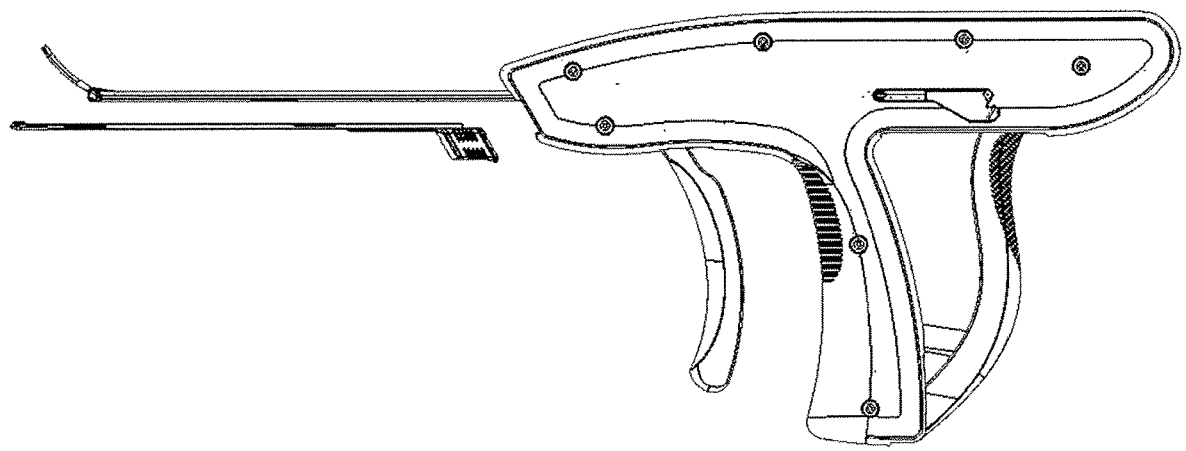
Figure 15C:
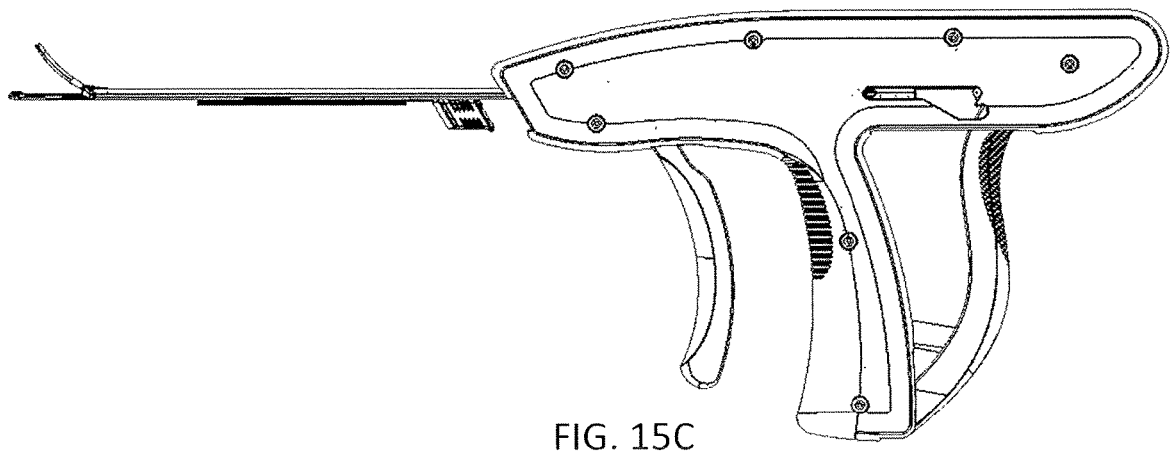
Figure 15D:
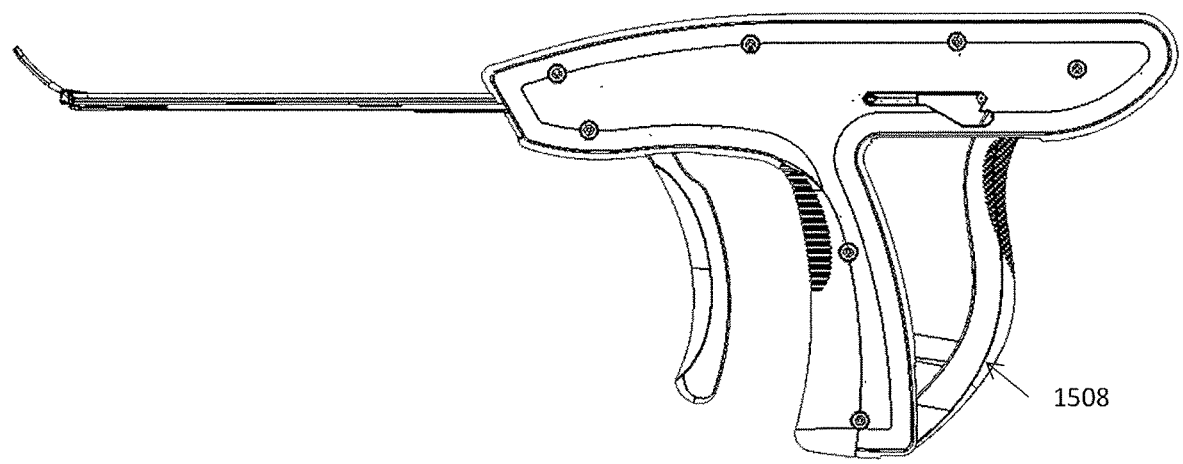

FIGS. 14A and 14B illustrate loading of a preloaded cartridge onto a suture passer (a durable assembly of a suture passer) to form a loaded suture passer that can pass two bights of suture. In FIG. 14A the cartridge 1403 is placed adjacent to the underside of the durable assembly 1401 of a suture passer, and the two are aligned so that a keyed region on either (or both) the cartridge and durable assembly. Once the keyed regions are joined, the cartridge may be slid proximally relative to the durable assembly to engage the two; a connector may be engaged to lock the cartridge to the durable assembly, forming a loaded suture passer, as shown in FIG. 14B. FIGS. 15A-15E illustrate engagement of a preloaded cartridge 1503 to a durable assembly 1501 of a suture passer to form the loaded suture passer. In FIG. 15A, the cartridge 1503 is brought near the underside of the durable assembly 1501, the engagement region (keyed regions) on the cartridge and the durable assembly 1501 are alighted (FIG. 15B), and the engagement regions are coupled together to connect the cartridge to the durable assembly, as shown in FIG. 15C. In FIG. 15D, the cartridge is slid proximally until one or more couplers on the cartridge are engaged with counterparts on the durable assembly. For example, the jaw housing (e.g., the suture storage region of the jaw housing) may be coupled to a rod, shaft, or other axially movable structure on the durable assembly that is connected to a control (e.g., the lower jaw/needle extending controller 1508). In addition, the tissue penetrator (not shown) may be coupled (e.g., via a needle sled) to a similar rod/shaft/axial needle actuator that is also connected to a lower jaw/needle extending control 1508, or other control.

Figure 15E:
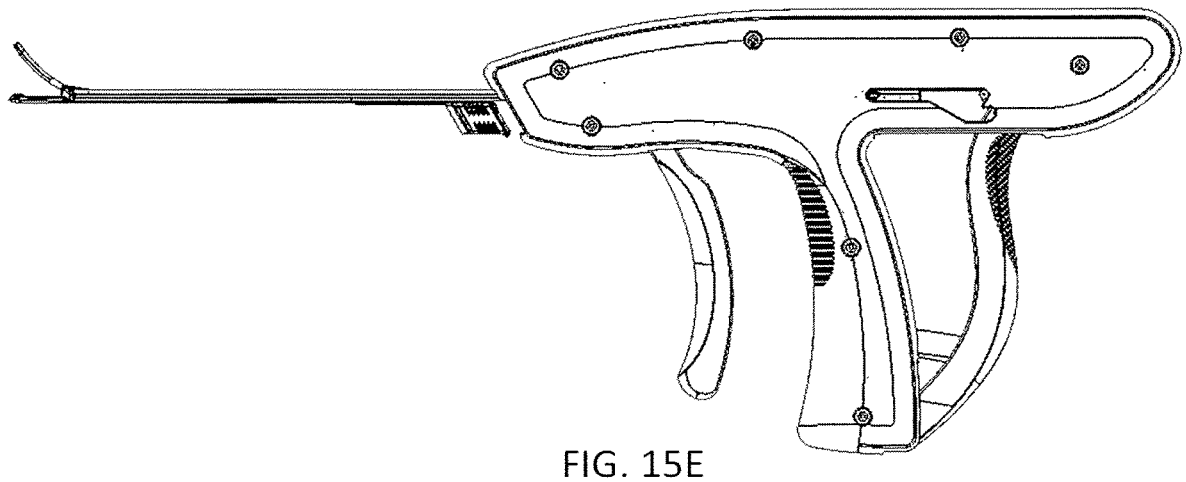

Finally, in FIG. 15E the completed suture passer assembly may be used to pass at least two bight regions of suture; the lower jaw (formed from the cartridge) may be extended and retracted, and the needle (tissue penetrator) may similarly be extended and retracted.

FIGS. 16A-16C illustrate various examples of coupling mechanisms that may be used. For example, in FIG. 16A, the underside of the durable assembly of a suture passer is shown, showing a keyed region 1604 for receiving a complementarily keyed region on a cartridge. For example, in FIG. 16A (and shown in greater detail in FIG. 16B) the durable assembly may include an opening into which flanged wings on the jaw housing of a cartridge may fit. Once inside the opening, the cartridge flanges may fit into a track or channel 1606 that helps keep the cartridge aligned on the durable assembly. FIG. 16C also illustrates a coupler 1608 that projects from the underside of the durable assembly and can engage with a receiver on the cartridge (see, e.g., FIGS. 12A and 12B, receiver region 1204). In this example, after engaging the keyed regions, the cartridge is slid distally until it engages with a retainer (coupler 1608) that releasably locks the two together. In FIG. 16C, the coupler is a projecting, curved surface that slightly deflects the proximal end of the cartridge until it pops into the receiver region (opening 1204) in the cartridge housing (e.g., suture holding region). Thereafter, the cartridge forming the lower jaw assembly may be retracted so that the distal end of the lower jaw formed by the cartridge is withdrawn proximally, or it may be extended distally (to extend the lower jaw distally). The cartridge may be removed by pulling the proximal end of the cartridge (e.g., the suture holding region) off of the coupler and sliding the cartridge forward to again align the keyed regions and separate the cartridge from the durable assembly.

Figure 17A:
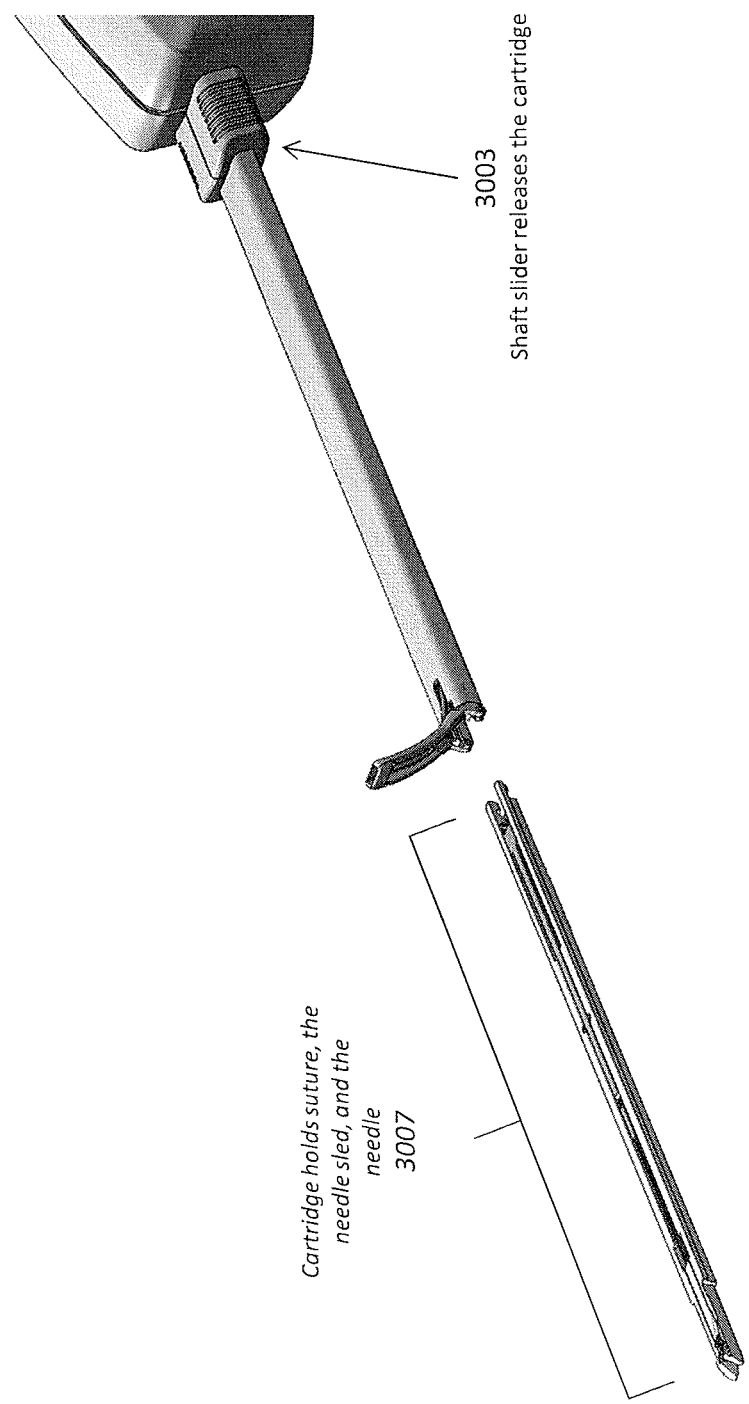
FIG. 17A illustrates another variation of coupling a reloaded and automatically reloadable cartridge to a suture passer assembly.

FIG. 17A illustrates another variation of a preloaded cartridge that may be coupled with a durable assembly of a suture passer. In some variations the cartridge is configured as a per stitch cartridge. The cartridge may contain a segment of preloaded suture which may or may not include a pre-tied knot and some portion of the distal end of the device. FIG. 17A shows an embodiment where the distal cartridge 3007 is comprised of the lower jaw component that contains the needle pathway, the needle, a needle sled (a connector that attaches the needle to a translatable element in the handle 3003), and a suture (not visible). The same features that allow separation of the lower jaw into a distal (needle path) and proximal (acutation control) proitons that may connect/snap together may allow substnatial reductions in the device height (e.g., the shaft height).

Figure 17B:
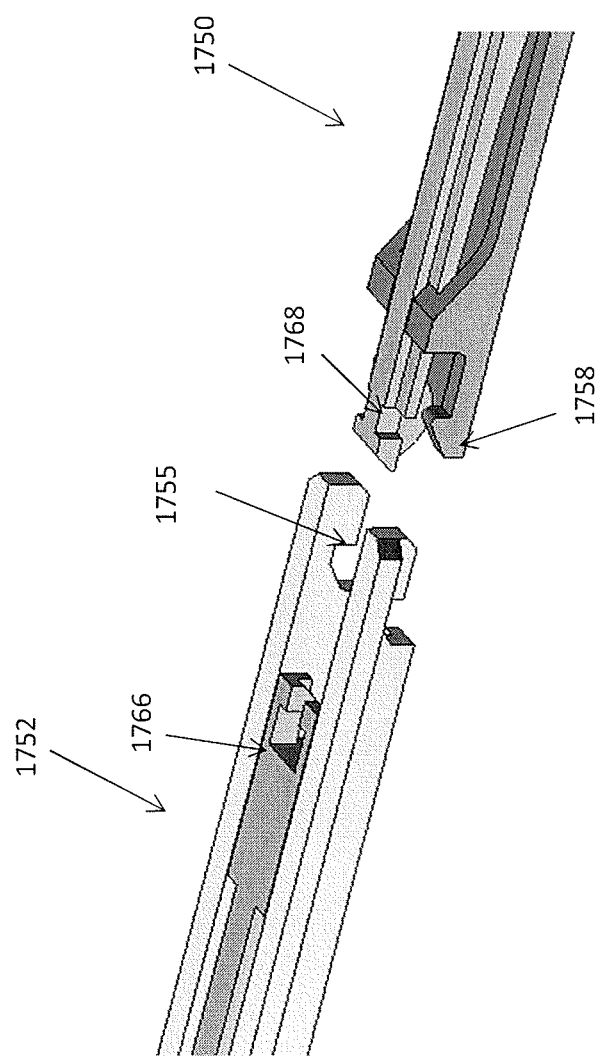
FIG. 17B is an enlarged view of coupling region between the reloaded and automatically reloadable cartridge and the durable/reusable suture passer assembly.

The proximal end of the cartridge may contain features that allow each of the members requiring actuation, the needle and the lower jaw, to click or snap into a corresponding actuator in the handle (See FIG. 17B). An actuator on the handle can be activated by the user to disengage the connection features, facilitating removal of a used cartridge and readying the handle for loading a new cartridge. The advantages of a per stitch cartridge include preloading the suture into the cartridge so the surgeon or the scrub nurse do not have to deal with as much suture management in the sterile field, as well as keeping the suture housed within the lower jaw so that it cannot get pinched between the inferior surface of the device and the anterior horn of the meniscus or the tibia. Third, with both ends of the suture preloaded into the cartridge, the above architecture allows the surgeon to place both legs of the suture without removing the device from the joint. This eliminates the possibility of tissue bridging. Lastly, the durable assembly (including the handle) is reusable throughout the case.

In FIG. 17B, the engagement region includes a housing engagement region 1755 at the distal end of the cartridge for engagement between the cartridge housing (forming the lower jaw) and the durable portion of the tissue penetrator (housing engagement region 1758), as well as a needle (tissue penetrator) engagement region 1766 at the distal end of the device that couples the tissue penetrator with a needle actuator (e.g., slider/pusher) 1768 in the durable portion of the tissue penetrator 1750. Thus, the cartridge may be adapted to engage two portions of a suture passer: a housing/jaw engagement region 1758 that holds the preloaded/disposable lower jaw 1752 to the durable portion of the tissue penetrator 1750 and a needle engagement region 1766 that couples with a needle actuator 1768 in the durable tissue penetrator.

Although the variations described above include tissue penetrators (needles) that engage multiple lengths of suture with a jaw housing, in some variations the tissue penetrators and jaw may be differently configured. For example, FIG. 18A-18E illustrate one variation of a lower jaw and tissue penetrator that are configured to be used as part of a suture passer that can hold and pass two lengths of suture. In FIG. 18A, a jaw member (e.g., lower jaw member) that has a suture loading region 1803 adapted to hold a second length of suture while the first length of suture is held in a suture retainer region 1805 in the tissue penetrator 1801. The jaw member shown in FIG. 18A is not yet loaded with a suture, and includes a central channel 1811 into which the suture may be fed to load the device. The tissue penetrator 1801 is held within the jaw, and is configured to slide axially distally/proximally and can exit the jaw member though a deflecting exit 1815 that directs the tissue penetrator across an opening formed between the jaw members.

FIGS. 18B-18E illustrate loading of a pair of suture loops into the tissue penetrator and suture loading region 1803. For example, in FIG. 18B, the first suture loop 1801 has been passed into the central channel 1811 of the jaw member. This first loop of suture 1801 passes though the suture loading region 1803 of the jaw member and into the suture retainer or holder region 1805 in the tissue penetrator, as shown in FIG. 18C. This may be achieved by positioning the tissue penetrator at a particular region within the jaw member so that the suture retainer region 1805 is continuous with the edge (which may be curved) of the suture loading region 1803 so that the suture passes into the suture retainer region of the tissue penetrator. A second loop of suture 1808 may then be loaded by again passing the loop over a portion of the jaw member and into the central channel 1811. The tissue penetrator may be moved distally or proximally to make room for the second suture loop within the suture loading region 1803 without interfering with the suture already in the tissue penetrator, as shown in FIG. 18D. Once loaded, the tissue penetrator may be advanced slightly distally to secure the two suture loops within the lower jaw, as shown in FIG. 18E. After the first length of suture has been passed to the opposite jaw and held there, the tissue penetrator may then be extended back into jaw member and loaded with the second loop of suture, similar to FIG. 18C.

In some variations, the devices described herein may include one or more suture management features such as suture tensioners, suture cleats, suture clamps, suture channels, and/or other structures that guide, hold, apply tension, and release the suture. These suture management features may be generically referred to herein as suture cleats.

A suture management feature such as a cleat and/or tensioner may be used to hold one or more lengths of suture, and may generally aid in preventing the suture from dropping off of the device and/or becoming tangled. A suture management feature may also help in automatically loading a length of suture in a tissue penetrator, as described above in reference to FIGS. 18A-18E. A suture management feature may maintain and/or control the tension on the suture as the device is operated. For example, a suture cleat may be biased (e.g., spring loaded) to maintain a relatively constant tension on the suture during operation, or may be used with a tensioning member (such as a tension arm or pin). As mentioned, a suture management feature such as a cleat may include a projection, pin, clamp, tensioner or other structure that holds the suture (or multiple lengths of suture). Further, in some variations a suture management feature such as a cleat may be releasable, either manually or automatically, so that when a suture or multiple lengths of suture are secured by the cleat the suture(s) may be released from the cleat by triggering a cleat release.

As used herein, a suture cleat may include an opening into which the suture may be held. For example, a suture cleat may include a projection to which a length of suture may be secured. The cleat may hold the length of suture by clamping the suture or by providing a typically wedge-shaped opening into which the length of suture may be captured. In some, but not all, variations the suture may be wrapped around the cleat. In some variation, the cleat may actively, e.g., by spring or biasing member, pinch the suture(s) between one or more surfaces to secure the suture(s). A suture may be removed from the cleat manually (e.g., by manually pulling the suture out of the cleat) or automatically. For example, a cleat may include a pushing member that pushes the suture out of the cleat. In some variations a projecting portion of the cleat may be configured to retract, e.g., into the jaw member, releasing any suture held therein. In some variations, a clamping portion of the cleat may be configured to release or relax any clamping force holding the cleat. Release of a length of suture from the cleat may be triggered by an actuation mechanism including a mechanical mechanism (e.g., lever, toggle, cam, etc.) or electrical/magnetic mechanism (e.g., solenoid, motor, magnetic catch, etc.). In some variations the cleat may be triggered to release a length of suture during a particular step in the operation of the suture passer. For example, the suture may be released from the cleat when the tissue penetrator is retracted for reloading with a second bight of suture; the suture cleat may release the suture so that a bight of suture can be transferred from a suture loading region in a jaw into a tissue penetrator.

Figures 22A, 22B:
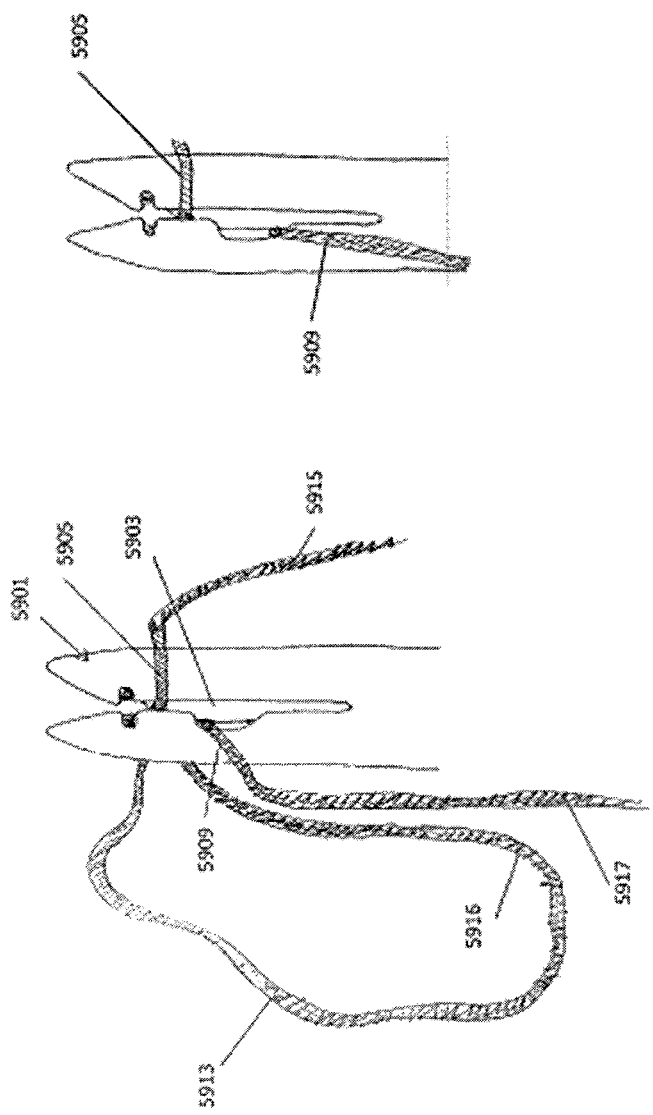
FIG. 22A shows a top view of one variation of a jaw member in which to loops (bights) of suture have been loaded.
FIG. 22B shows a top views of the jaw member of FIG. 22A in which the second suture bight is held taught by a suture management element.

Thus, in variations in which multiple bights of suture are loaded in to the device, a suture management feature may be used to hold and/or tension a second length of suture within the lower jaw member so that it may engage with the tissue penetrator after the first loop of suture has been passed. For example, FIG. 22A shows a distal portion of a lower jaw member 5901 and tissue penetrator 5903 into which two loops of a suture have been loaded. A first loop 5905 has been loaded into the tissue penetrator, and a second loop 5909 has been loaded into a suture loading region of the jaw, as described in FIGS. 18A-18E. The ends 5915, 5917 are loose, as is the length of suture between the two bights 5913. In some instances it may be beneficial to secure the free ends of the bight 5909 that is loaded in the suture loading region 5917, 5913. It may also be advantageous to hold the second bight under tension. By securing the ends 5917, 5916 of this second loop/bight 5909, and by holding it in tension, it may be primed for automatically loading into the needle after the needle has passed the first bight to the opposite jaw, as described above. This is illustrated in FIG. 22B, showing the second bight 5916 held taught with the ends of the bight 5916, 5917 (not visible in FIG. 22B) secured to a suture cleat.

Figure 22D:
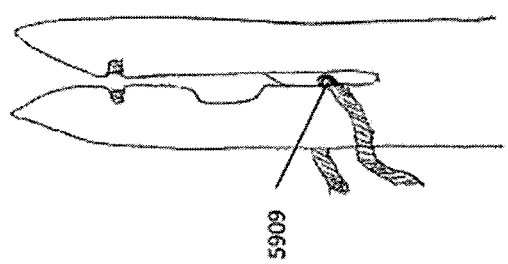
FIG. 22D shows the same view of the jaw member after the suture management element has released the suture bight.
Figure 22C:
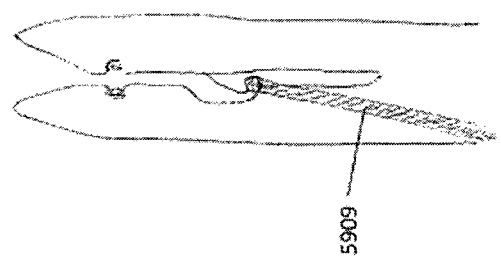
In FIG. 22C the suture bight has been automatically loaded into the suture retainer region of a tissue penetrator.

Pulling this second suture bight taught as shown in FIG. 22B by holding the ends of the suture bight in the cleat may help with automatically loading the second bight into the tissue penetrator, as illustrated in FIG. 22C. In this example, the tissue penetrator has been retracted proximally, exposing the opening of the suture retainer region. Tension on the suture loop, as well as the shape of the suture holder region on the jaw has driven the suture loop 5909 into the suture retainer region. Thereafter, the tissue penetrator may be withdrawn further proximally, and the suture cleat automatically (or manually) disengaged, releasing the ends of the second bight so that the second loop is loose, though held in the suture retainer region of the tissue penetrator, as shown in FIG. 22D.

Figure 22E:
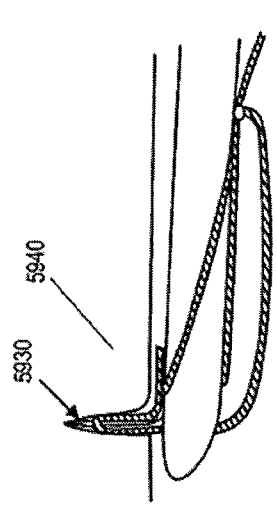
FIGS. 22E-22H illustrate the use of a suture management feature to secure and apply tension to one of the loops of suture loaded into the jaw member of FIG. 22A during loading and operation of a suture passer.
Figure 22F:
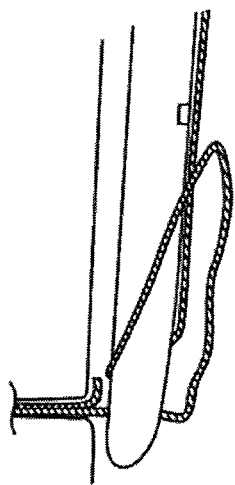
Figure 22G:
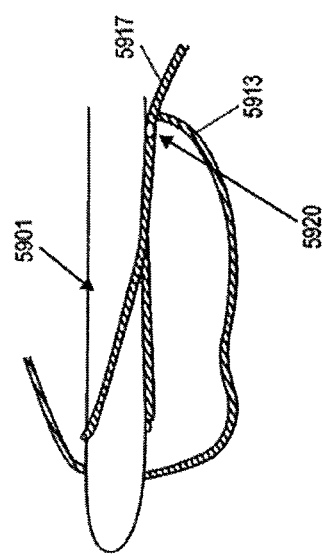
Figure 22H:
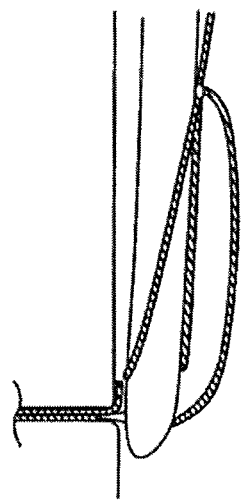

FIGS. 22E-22H show a side view of the distal end of the lower jaw region shown in FIGS. 22A-22D, in which the loose ends of the second bight are secured (with slight tension) using a cleat. In FIG. 22E, which is a side view of a jaw member corresponding to the top view shown in FIG. 22B, the free ends of the second suture bight are held in tension against the lower jaw 5901 by a cleat 5920. The loop of suture is held in slight tension, pulling the suture bight proximally within the suture holding region and preventing it from falling out of the suture loading region which may also help pull it into the suture holding region of the tissue penetrator after passing the first bight. For example, in FIG. 22F the lower jaw is shown adjacent to a region of tissue 5940; the upper jaw is presumed to be positioned on the opposite side of this portion of tissue (not shown). The tissue penetrator 5930 is shown extending though the tissue, pushing the first bight through the tissue, while the second bight is held securely in the lower jaw by the cleat. FIG. 22G shows the device and tissue after withdrawing the tissue penetrator, leaving the first bight in the tissue. The side view of FIG. 22G corresponds to FIG. 22C. Thereafter, the tissue penetrator may be retracted proximally to engage the second bight so that it may be passed through a different region of the tissue. After retracting the tissue penetrator and reloading it with the second bight, one or both ends of the second bight may be released from the cleat. In some variations the cleat holding the second bight may be configured to automatically release one or both ends of the suture, as illustrated in FIG. 22H. FIG. 22H is a side view corresponding to the top view of FIG. 22C. In this example, retraction of the tissue penetrator (not visible) proximally may trigger release of the suture from the cleat; in FIG. 22H, the cleat has been retracted into the lower jaw, dropping the lengths of suture. In some variations the cleat may pinch or engage the length(s) of suture by a friction or grasping mechanism, and retraction of the tissue penetrator and/or loading of the second bight onto the suture passer may cause the release of the lengths of suture from the cleat.

Figure 23:
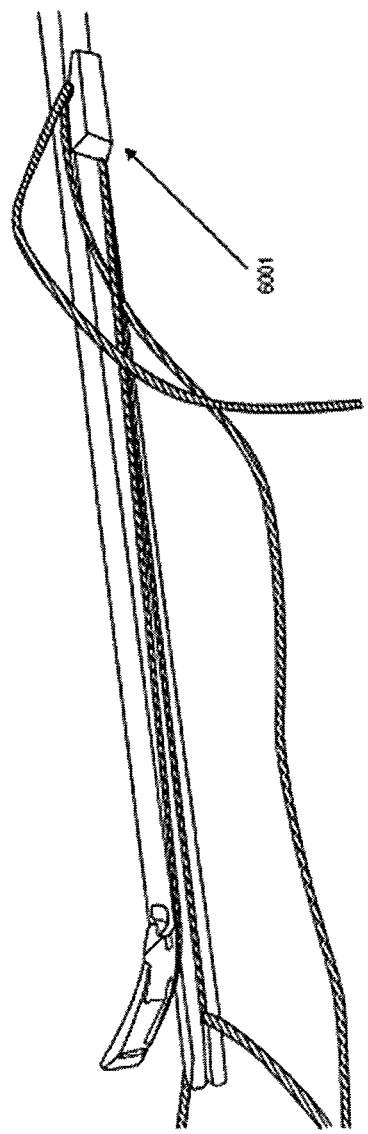
FIG. 23 shows a bottom perspective view of one variation of a suture passer device including a suture cleat holding a suture.

FIG. 23 shows a bottom view of one variation of a suture passer device similar to the variation shown in FIGS. 1A and 1B, including a suture management feature (a suture cleat in this example) securing the end of a bight of suture that has been loaded into the suture passer. In this example, a suture cleat 6001 is located on the lower or second jaw member that is axially movable in the long axis of the device. Thus, as the lower jaw is extended or retracted, the cleat moves with the lower jaw. In some variations the cleat is a tensioning member that may adjust the tension on the suture and/or suture loop. One or more suture management features may be included on any appropriate region of the suture passer, including the first jaw member, second jaw member, tissue penetrator, elongate member, handle, etc.

Figure 24A:
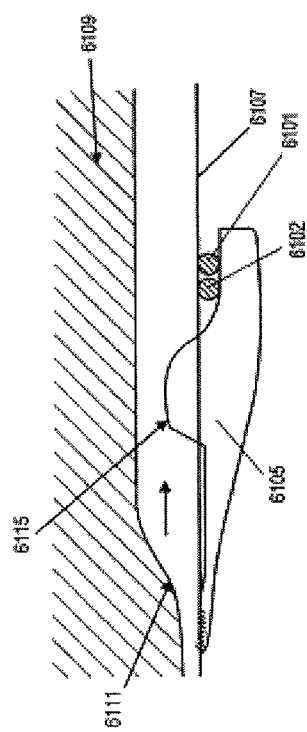
FIGS. 24A and 24B illustrate one variation of a suture management feature (e.g., cleat) configured to automatically release one or more lengths of suture during operation of a suture passer.
Figure 24B:
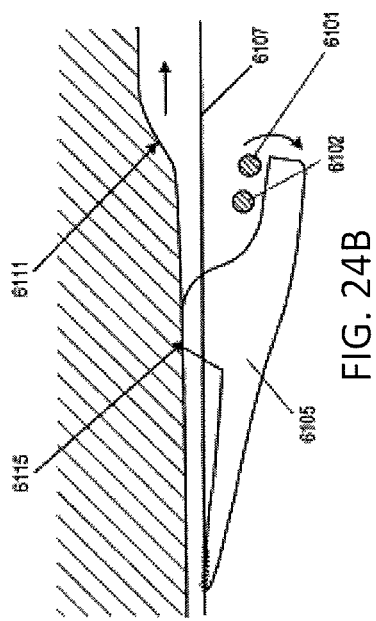

As mentioned, a suture cleat may be configured to automatically release a length(s) of suture, or reduce or release tension on the suture, when the second length of suture is ready to be loaded onto the tissue penetrator. One example of an automatic release cleat is illustrated in FIG. 24A. In this example, the cleat holds two lengths of suture 6101, 6102 securely against the outer surface of the lower jaw. In FIGS. 24A and 24B the suture is shown only in cross-section, where they are held and released by the cleat. For example, in FIG. 24A, the cleat 6105 pinches the lengths of suture 6101, 6102 against the wall 6107 of the lower jaw member. In this example, the cleat is configured as a leaf spring that is pre-biased against the lower jaw member; the distal end of the cleat is secured to the lower jaw. The cleat includes an internal cam surface 6115. Pushing against this cam surface may drive the cleat away from the wall of the lower jaw member, allowing the lengths of suture to be released, as shown in FIG. 24B. In this example, the cleat is automatically released when the cam surface 6115 is driven against a complimentary release cam surface 6111 within the lower jaw. In some variations, this release cam surface is part of the tissue penetrator. Thus, as the tissue penetrator is drawn proximally to load the second bight, this release cam surface (formed as a region of the tissue penetrator) drives release of the lengths of suture from the cleat. In some variations, a separate lever or other mechanism may be used. The cleat may also include a more active release mechanism, in which the lengths of suture are driven out of the cleat. For example, a release cam surface may be driven into the cleat proximally as the tissue penetrator is withdrawn proximally to load the second bight onto the tissue penetrator, and this release cam surface may drive the sutures out of the cleat.

FIGS. 25A and 25B illustrate another variation of a suture cleat, similar to the variation shown in FIG. 24A. In this example, the suture cleat 6201 is also attached at one side to the lower jaw of the suture passer 6203, and a suture 6205 is held (clamped) in the jaws at the opposite end of the suture cleat 6201. The clamping region of the cleat may be deflected away from the lower jaw, as shown in FIG. 25B. In this example, the suture (or multiple lengths of suture) can be clamped or held in the long axis of the clamping region of the cleat. Opening the clamp region allows the suture to be released, as shown in FIG. 25B. The clamp region of the cleat may be deflected by pushing against a cam surface that is connected to the clamping region. In FIG. 25B, the cleat includes a region 6209 that can be used to deflect the clamping region. Thus, as just described, a suture passer may place two legs of a circumferential stitch with only a single insertion of the instrument. In some variations, the suture passer device may be loaded with two ends of a length of suture into one jaw (i.e. the lower jaw), inserting the suture passer into the knee, having a tissue penetrator pass one suture end up to the other jaw (i.e. the upper jaw) where it is removed off of the tissue penetrator. The tissue penetrator may then return to the lower jaw and pick up the second end of the length of suture. The instrument is placed in another location, and the tissue penetrator is again advanced, passing the suture off onto the upper jaw. With both ends of the suture having traveled from the lower jaw to the upper jaw, removing the suture passer will result in a circumferential stitch around the tissue.

In the above embodiment, one configuration for loading two ends of a single suture into the suture passer so that a single tissue penetrator can pass them with sequential advances of the tissue penetrator involves specific jaw features. For example, the lower jaw may contain a track for guiding the tissue penetrator. One section of the track is cut out leaving a space for a second suture to reside beyond the width of the needle. The space (suture holding region 1803) is identified in FIG. 18A.

In some variations the device includes a control (e.g., switch, lever, button, etc.) that moves the tissue penetrator to assist in loading. For example, a suture passer including a proximal handle is shown in FIGS. 1A and 1B.

The procedure for loading a suture passer may include first loading one end of the suture into a notch contained on the tissue penetrator (e.g., FIGS. 18A-18C). A suture can be pinched in place by pulling the tissue penetrator back. Next the other end of the suture may be loaded into the space that is cut out of the tissue penetrator guiding track. This second end of the suture is pulled taught away from the tissue penetrator as shown in FIG. 18D. While the second end is pulled taught into this space away from the tissue penetrator, the user flips a switch on the handle causing the needle to move distally a small amount.

In some variations, the suture passer is configured to be loaded with one or more sutures so that the bights of the two ends of the suture both reside on the superior surface of the lower jaw. FIGS. 19A and 19B illustrate schematically two variations in which both legs of a loop of suture are held on the same side of the device (e.g., the superior surface of the lower jaw) when loaded. These embodiments may include tissue penetrators that have two notches, allowing a suture can wrap around the tissue penetrator so that the suture can originate on the superior surface of the lower jaw, wrap around the tissue penetrator, and return on the superior surface of the lower jaw. FIG. 19A shows a tissue penetrator having two notches (adjacent to each other) on one side of the tissue penetrator, and FIG. 19B shows a tissue penetrator having two notches on opposite sides of the tissue penetrator. In both cases the suture loop may wrap around the tissue penetrator so that the length of suture before and after the loop region extends on the same side or surface of the suture passer. In both examples, the jaw in which the tissue penetrator resides is also adapted for loading the two or more sutures, and may include a suture loading region (or regions) to hold a suture loop until the suture holder in the tissue penetrator is empty of another suture.

Figure 21:
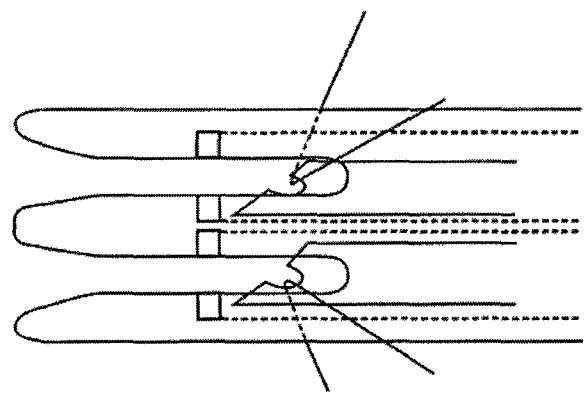
FIG. 21 shows another variation of a suture passer configured to pass two lengths of suture.
Figure 20:
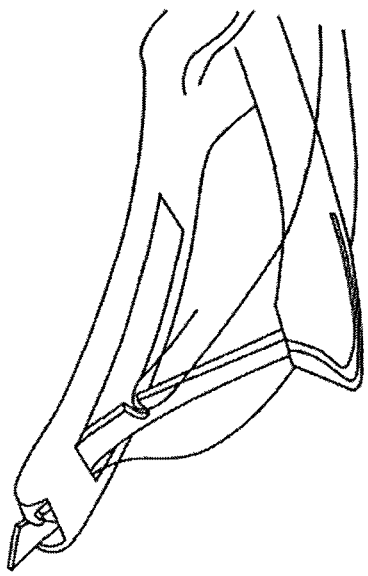
FIG. 20 shows another variation of a suture passer configured to sequentially pass two lengths of suture.

In some variations multiple loops of suture may be sequentially delivered with a tissue penetrator in which the tissue penetrator has multiple suture retainer regions. In some variations the suture retainer regions are configured as one or more notches. The suture retainer regions may be positioned along the proximal to distal length of the tissue penetrator. For example, in some variations, a second suture retainer region is positioned proximal to a first suture retainer region along the length of the tissue penetrator. In this variation, an example of which is shown in FIG. 20, the proximal handle of the suture passer may coordinate travel of the tissue penetrator so that to pass the first loop of suture in the distal most suture retainer region of the tissue penetrator, the distal suture retainer (e.g., notch) passes the suture stripper in the upper jaw while the second suture does not (by limiting the distal extension of the tissue penetrator). This is shown in FIG. 20. The second loop of suture is passed by (e.g., via a control on the handle or automatically) advancing the tissue penetrator more distally so that the more proximal suture retainer region on the tissue penetrator extends past the suture stripper in the upper jaw, trapping both the first and second loops of suture. Another variation of a suture passer adapted for passing at least two loops of suture (either sequentially or simultaneously) is shown in FIG. 21. In this example, two tissue penetrators are included in parallel, each one loaded with a suture. In some variations the tissue penetrators are side-by-side as shown in FIG. 21; alternatively, the tissue penetrators may be atop each other. The sutures may be delivered by extending each (or both) of the tissue penetrators across the tissue and into the second jaw member where a suture stripper can retain the suture(s).

In operation, the preloaded suture passers described herein may be used to suture any appropriate tissue, not limited to knee (e.g., meniscus, ACL, etc.), hip (e.g., hip labrum, etc.), shoulder (e.g., rotator cuff), etc. For example, FIGS. 26A-26L illustrate one method, including optional steps, of using a preloaded suture passer to repair tissue; in this example, the meniscus includes a tear 2609 which may be circumferentially stitched by placing a first end of the suture through the meniscus on one side of the tear, and placing the opposite end of the suture on the other side of the tear.

Figure 26B:
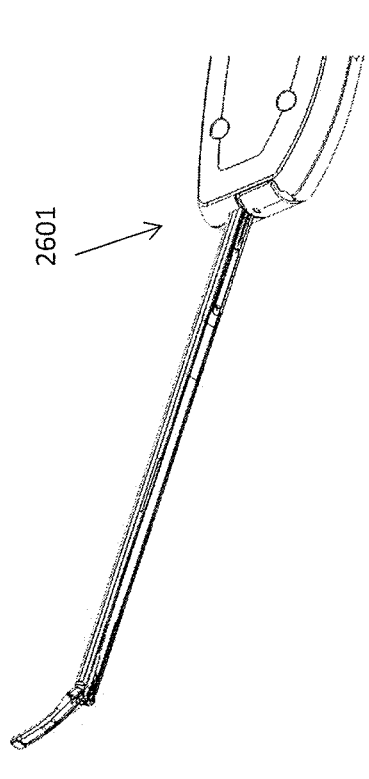
FIGS. 26A-26L illustrate one method (including optional steps) of operating a system such as the systems described herein including a preloaded and automatically reloadable cartridge to repair tissue.
Figure 26D:
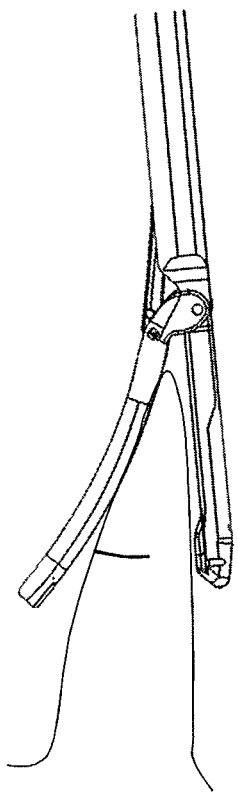
Figure 26A:
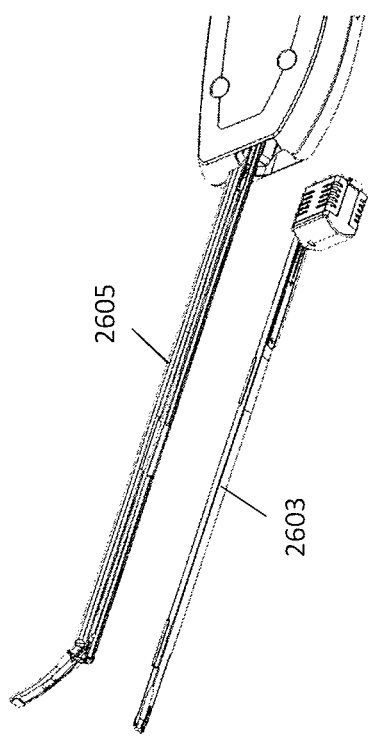
Figure 26C:
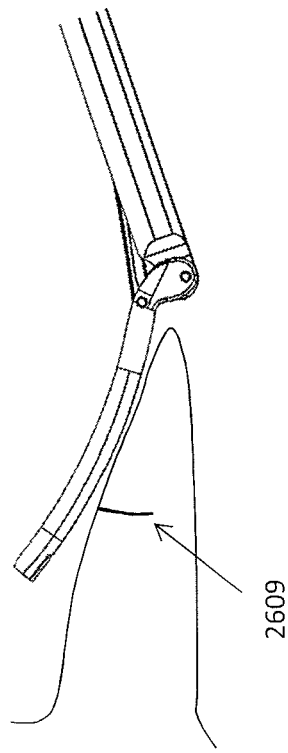
Figure 26E:
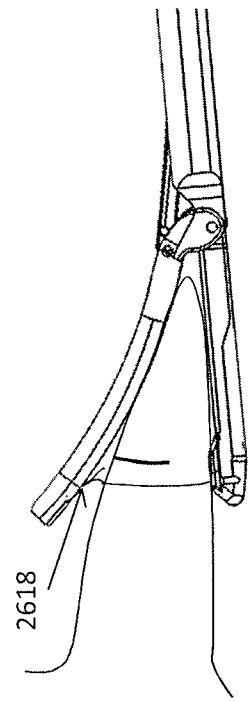
Figure 26F:
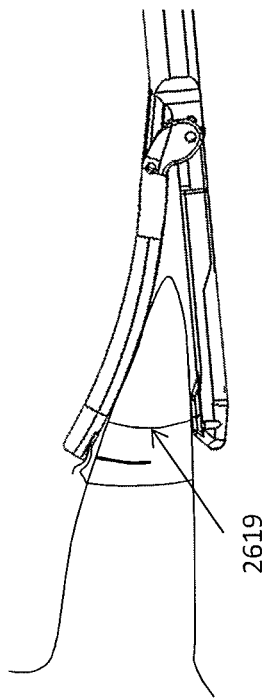

In FIGS. 26A and 26B, the suture passer is first assembled by coupling a preloaded cartridge 2603 with a durable assembly 2605 to form a suture passer 2601. In FIG. 26C, the suture passer is positioned adjacent to the target (torn meniscus) tissue; in this example, the upper jaw of the suture passer is pivotable/bendable relative to the elongate axis of the device, and the lower jaw is axially retracted (proximally) so that the tip of the suture passer has a very narrow profile and can fit into the narrow confines of the anatomy. In FIG. 26D, the lower jaw is extended distally to surround the torn meniscus. In FIG. 26E the tissue penetrator 2611 is extended from the lower jaw (from the cartridge) to the upper jaw while pushing a first bight region of suture. The tissue penetrator is then retracted, leaving the first bight region of suture at a first end of the suture held in the suture retainer region 2618 of the upper jaw, as shown in FIG. 26F. The suture 1615 then extends from the upper (superior) side of the meniscus and the upper jaw to the lower (inferior) side of the meniscus and the lower jaw. Withdrawing the tissue penetrator into the lower jaw housing (shown in FIG. 26E) may automatically re-load the tissue penetrator with the second bight of suture near the distal end of the suture, as discussed above. For example, when the second bight of suture is held in a fixed position and the distal end region of the suture next to the second bight is held in a releasable hold on the tissue penetrator, the tension pulling the second bight proximally may pull the second bight into the suture engagement region (now empty) on the tissue penetrator. This automatically re-loads the tissue penetrator with a second bight of tissue.

Figure 26G:
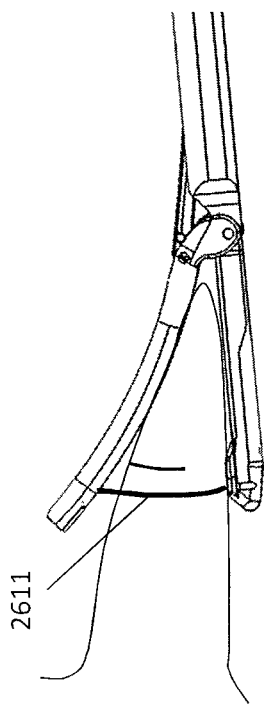
Figure 26H:
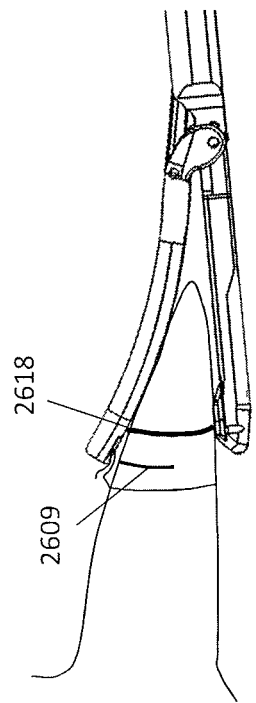
Figure 26J:
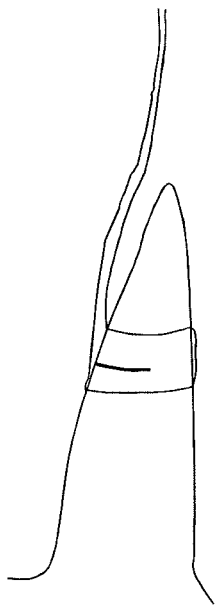
Figure 26L:
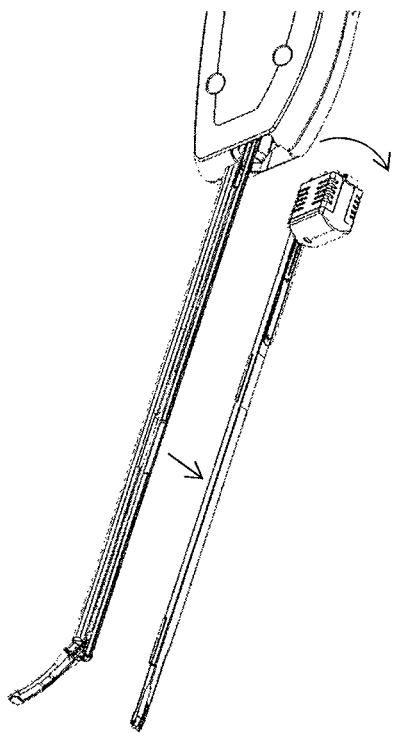
Figure 26I:
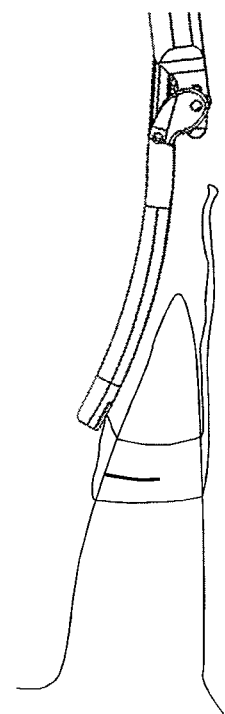
Figure 26K:
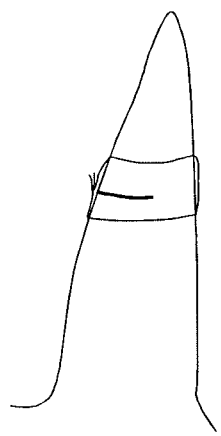

In FIG. 26G the suture passer is repositioned on the meniscus so that it can suture on the more apical side of the tear 2609. Once positioned, the suture passer is again activated (e.g., by actuating the lower jaw/needle extension control on the handle) to drive the tissue penetrator from the lower jaw through the tissue to the upper jaw, where the second bight region also engages with a suture retainer 2618 in the upper jaw. The same or a different suture retainer may be used. Withdrawing the tissue penetrator again leaves the second length 2619 of suture behind in the meniscus, as shown in FIG. 26H. Thereafter, the lower jaw can be retracted, leaving the suture "slack" 2622 (the suture body) on the inferior side of the meniscus, and allowing the loop to be closed by withdrawing the suture passer (including the upper jaw) from the knee, as shown in FIG. 26J. A knot pusher (not shown) can then be used to tighten and tie a knot in the loop of suture, repairing the tear, as shown in FIG. 26K. The cartridge may then be removed from the durable assembly, as shown in FIG. 26L, and another (new) cartridge may be applied.

Pre-tied Suture Knots

Also described herein are pre-tied suture knots that may generally be used with any of the suture passers (including suture cartridges) described herein. In some variations, a suture having a pre-tied knot (and the knotted apparatus forming the pre-tied knot) may be loaded into the device, e.g., in the cartridge of the device, so that the suture may be passed through tissue using the suture passer as describe above. Once the length of suture (or multiple lengths of suture) has been passed through the target tissue, the pre-tide knot may be pushed down to secure the length of suture in the tissue. For example, an end region of one or both (in variations in which two lengths of suture are being passed) lengths of suture may include a pre-tied knot, and the suture including the pre-tied knot may be passed through the tissue by the tissue penetrator. In some variations the pre-tied knot includes a leader snare. For example two lengths of suture (from the same elongate suture) may be passed through a tissue; in some variations, both lengths may be pre-knotted (e.g., may include a pre-tied knot), however only one of the pre-tied knots may include a leader snare and may be configured to allow another length of suture to be pulled through using the leader snare.

Any of the cartridges described herein may be pre-loaded with a length of suture and a length of "snare" material so that a loop or bight of snare and a loop or bight of suture may each be passed and may be consecutively and automatically loaded into the needle for passing by the suture passer. In general, a snare may be a filament material, similar or identical to the suture material, or in some variations a different material (e.g., having a different composition and/or diameter and/or surface property). The snare may be configured so that it forms a loop or bight, and the loop cannot be opened as with the bight of suture that is passed. For example the loop forming the snare may be closed at both ends, or at one end forming the loop.

The pre-tied knot systems described herein may also include a knotted region ("knot" or "knot system" or "knot former") that can be pushed down the suture to secure (knot, tie, or form the knot or tie). The knot forming may formed of a suture or suture material, or it may be formed of a differnet material. See, e.g., US20140074157, herein incorporated by reference in its entirety. The knot or knot former may also be referred to as a pre-tied knot body and may be formed from suture material at a region on the pre-loaded suture. The knot or knot former (aka pre-tied knot body) may be formed of one or more loops of the suture material, wherein each loop has at least one crossing point; and the leader and/or the suture forming the bight of suture within the cartridge may pass through the pre-tied knot body (e.g., the loops).

Figure 51A:
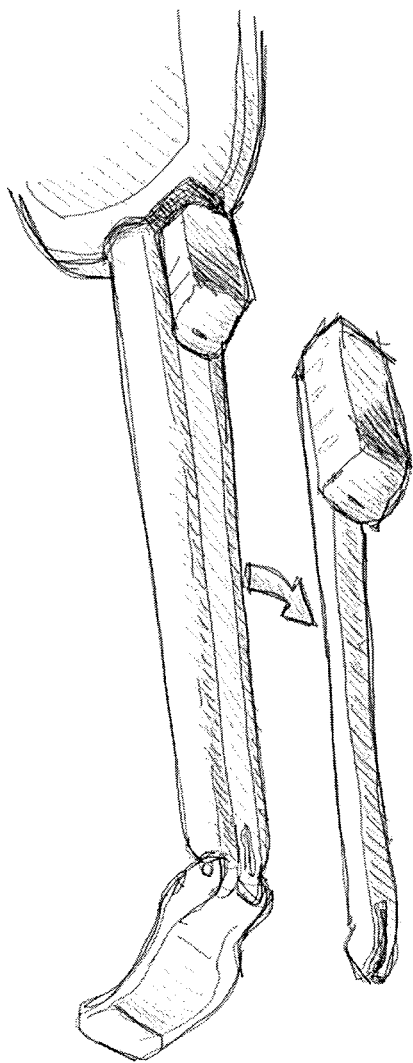
FIG. 51A shows a side perspective view of an example of a pre-loaded and automatically re-loading cartridge that includes a pre-tied knot.
Figure 51B:
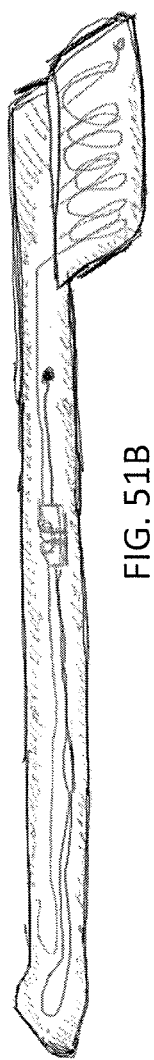
FIG. 51B shows one example of a side sectional view through a pre-loaded cartridge similar to the variation shown in FIG. 51A.
Figure 51C:
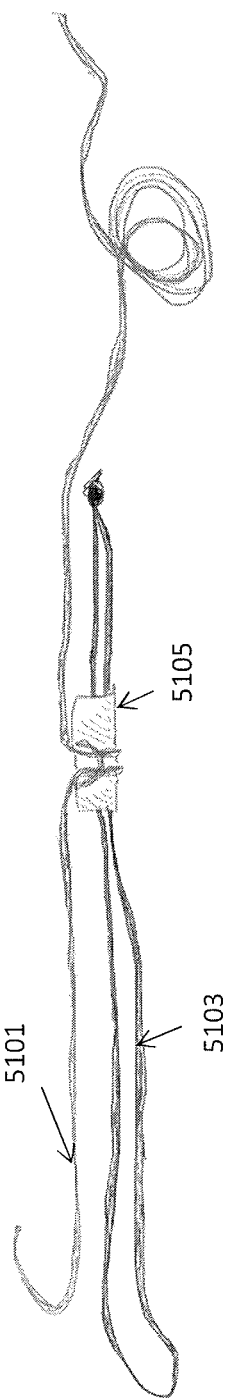
FIG. 51C illustrates one variation of a pre-tied suture knot system that may be loaded into a cartridge such as the one shown in FIG. 51A.

For example, FIG. 51A shows one example of a pre-loaded suture cartridge as described above. In this example, the pre-loaded cartridge is configured to connect to a suture passer to form the movable, e.g., slideable, lower jaw member. A pre-tied knot system, including a suture, a snare (aka leader) and a pre-tied knot body, is loaded into the replaceable cartridge, as illustrated in FIGS. 51B and 51C. In FIG. 51B, the pre-tied suture knot system shown within the cartridge. In FIG. 51C, this pre-tied knot system includes a primary suture 5101 and a snare 5103, as well as pre-tied knot 5105. The suture and snare are connected within the cartridge by the pushable pre-tied knot body 5105. The cartridge is configures so that the snare is preloaded (and will be passed first) into the tissue penetrator (needle) and the suture is poised to be automatically loaded after the snare (bight) is passed.

Thus, in some variations, the snare 5103 may form a first bight and the primary suture 5101 may form the second bight (or vice-versa). To operate a suture passer having a cartridge pre-loaded with a pre-tied suture knot (knot system), the first and second bights (e.g., both the snare and the primary suture) may be passed through different regions of the tissue and a free end of the primary suture may be manually or automatically be threaded into the snare and the snare withdrawn from the tissue to pull the suture back through the tissue a second time, along the path formed by the snare, looping around the tissue and through the pre-tied knot, so that the pre-tied knot can be pushed (or pulled) down to cinch the suture around the tissue. For example, a first bight of the snare loop may be passed through the tissue in a first location by the tissue penetrator of the suture passer. The suture passer can then be moved and the tissue penetrator automatically re-loaded with a bight of the primary suture; the bight of primary suture may then be passed (pushed and/or pulled) through the tissue at a different, e.g., adjacent, location by the tissue penetrator of the suture passer, and the distal end of the suture may be withdrawn (including withdrawn completely out of the tissue) and passed through the loop region of the snare (e.g., in some variations, the bight region of the snare that has been passed through the tissue). The snare may then be withdrawn from the tissue, pulling the end of the primary suture back through the tissue; the snare may also be pulled through the pre-tied knot, pulling the distal end of the primary suture with it. Once the snare is removed, the pre-tied knot can then be pushed distally to cinch the knot. This is illustrated in FIGS. 52-54C and (as a view from within the tissue) in FIGS. 55A-55E.

Figure 54B:
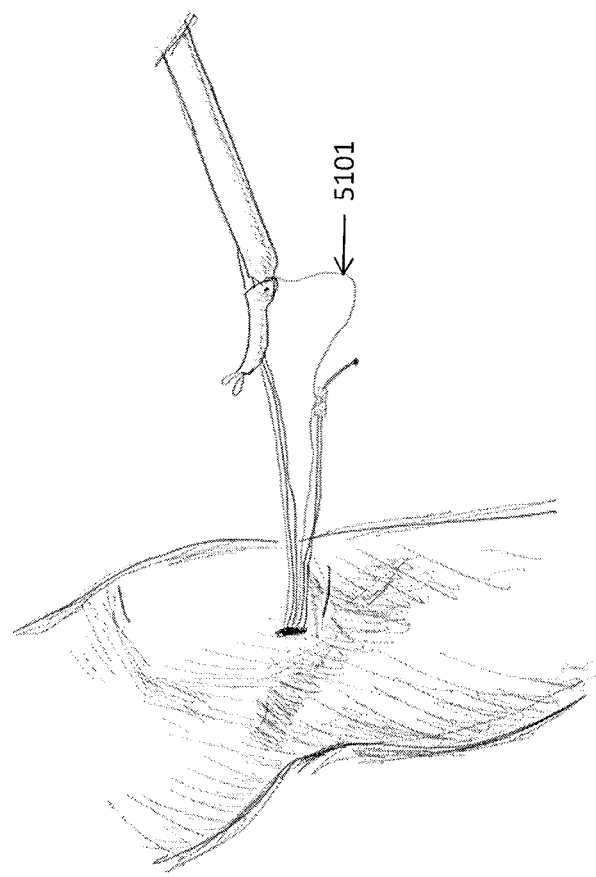
Figure 54A:
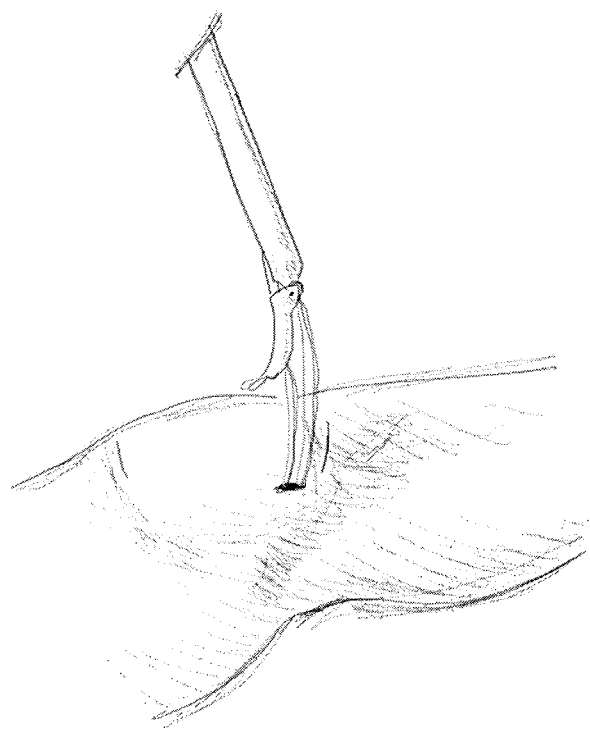

For example, in FIG. 52, the suture passer having a pre-loaded cartridge that is loaded with a pre-tied knot system such as the one shown in FIG. 51A-51C, is inserted into the body so that the tissue passer can be paced adjacent and/or around a target tissue. In this example, the target tissue is a meniscus, though it should be understood that any appropriate target tissue may be treated, including shoulder, hip (labrum), tendon, etc. The distal end of the suture passer device, with the cartridge pre-loaded with both suture and knot pushing system is inserted into an opening in the tissue as illustrated. As shown in FIG. 52A, the suture may then be operated as described above to pass a first bight (e.g., a bight of snare or "leader" portion 5103) through the tissue. Thereafter, the distal mouth of the suture passer may be positioned around a different region of the tissue, as shown in FIG. 53B, so that the suture passer can pass a second bight of tissue (e.g., a bight of the primary suture) through the target tissue at a different region. This example illustrates the tissue passer passing the suture bight from the inferior to the superior surface, so that the bight is captured by the upper arm of the suture passer after leaving the superior surface of the meniscus. Once both loops (bights) are passed, the suture passer can then withdraw slightly or completely out of the patient, as shown in FIG. 53C. As the suture passer device is withdrawn from the tissue (e.g., knee), one end of the primary suture 5101 may be pulled free. For example, the distal end of the primary suture may be released from the tissue penetrator, either manually (e.g., using a hand/finger or assisted by a probe or other tool). As shown in FIG. 54B, the pre-tied knot may also be pulled from the cartridge. The free end of the primary suture may be passed through the loop of the snare, snaring the primary suture, allowing the snare to be withdrawn from the tissue, and to pull the free (e.g., distal in this example) end of the suture back through the tissue in the path taken by the snare and then through the pre-tied knot, as shown in FIG. 54C. The suture (e.g., the proximal and/or distal end of the suture) may then be held taut while the pre-tied knot is pushed down to tighten over the tissue. This is shown in detail in FIGS. 55A-55E. In FIG. 55A, the snare 5505 is used to pull the primary suture 5503 through the tissue, as shown in FIG. 55B. The primary suture 5503 can then be pulled through the pre-tied knot 5507, as shown in FIG. 55C. In FIG. 55D the knot may be pushed to slide down the primary suture until it is secured near the tissue, which as shown in FIG. 55E in this example is a meniscus in the knee. In this example, the knot is formed on the underside (inferior surface) of the meniscus, which may be beneficial.

Also described herein are features and improvements that may generally be used with suture passers having upper and lower jaws, even where neither jaw is configured to be removable/reloadable.

In some variations a knot of suture may be passed through tissue using a suture passer as describe above in which a pre-tide knot is used to help secure the length of suture being passed to the device. For example, in some variations an end region of one or both (in variations in which two lengths of suture are being passed) lengths of suture are knotted, and this pre-tied knot may be passed through the tissue by the tissue penetrator. The pre-tied knot may or may not include a leader snare. For example, in some variations two lengths of suture (from the same elongate suture) may be passed through a tissue; both lengths may be pre-knotted, however only one of the pre-tied knots may include a leader snare and be configured to allow another length of suture to be pulled through using the leader snare.

In some variations, the suture passers described herein may include a second (e.g., lower) jaw that is thin (e.g., <0.11 inches in diameter at the widest point). In general, thinner second jaws may be inserted into narrower and difficult to access body regions. In some variations, in which the second jaw houses the tissue penetrator and the tissue penetrator extends across the distal-facing opening formed between the first and second jaw, the second jaw may include a deflection ramp or deflection structure to help deflect the tissue penetrator out of the jaw and across the distal-facing opening. The deflection ram or deflection structure in some variations may form a widened region of the second jaw. Although it was initially believed that this enlarged deflection region was necessary to provide sufficient deflection and control of the motion of the tissue penetration, recent information suggest that this may not be necessary, particularly when using a pre-bent or pre-biased shape memory material to form the tissue penetrator. Thus, as shown in FIGS. 27A to 27C, second jaws housing a tissue penetrator may be used, wherein each one has a different thickness and/or different size deflection region. For example, in FIG. 27A the second jaw includes a deflection region 2707 distal to the opening from which the tissue penetrator may be extended (extension of a tissue penetrator is illustrated in FIG. 27D). The widest diameter portion 2701 of the jaw in this example is the deflection region 2707. In some variations the widest diameter region is less than approximately 0.15 inches (e.g., less than about 0.14 inches, less than about 0.13 inches, less than about 0.12 inches, less than about 0.11 inches, less than about 0.10 inches).

Although a protruding deflection region may be helpful for steering the tissue penetrator/needle as it leaves the jaw, surprisingly, in some variations a protruding deflection member is not necessary, allowing the diameter of the jaw to be thinner. For example, in FIG. 27B, a jaw housing a tissue penetrator is shown without a protruding deflection member. FIG. 27E shows the jaw of FIG. 27B with a tissue penetrator 2705 extending from the side of the jaw. In this example, the jaw is thinner than the example shown in FIG. 27A; the maximum diameter (e.g., maximum height) of the jaw 2711 is less than about 0.10 inches (e.g., less than 0.09 inches, less than 0.08 inches, less than 0.07 inches, less than 0.06 inches, etc.). FIG. 27C shows another example in which the jaw is even thinner (e.g., less than 0.06 inches, less than 0.05 inches, less than 0.04 inches, less than 0.03 inches, etc.). In any of these examples the jaw may have a width. For example in some variations the width is between about 0.01 inches and about 0.15 inches. The tissue penetrator is typically thinner and narrower than the jaw so that it may fit within the jaw; the tissue penetrator (e.g., needle) may have a square, round, rectangular, or other cross-sectional area. In general, the tissue penetrator may be configured as a ribbon-shaped tissue penetrator, having a sharp (e.g., pointed, beveled, etc.) distal tip region, and a suture retaining region (e.g., hook, eyelet, etc.).

Any of the jaws illustrated in FIGS. 27A-9F may be used as a second or lower jaw for a suture passer as illustrated above (e.g., FIGS. 5A-6B). In general, any of the suture passers described herein (including those with removable jaws) may include first and second jaws having atraumatic (e.g., non-tissue penetrating) distal tip regions. Thus, as illustrated in these figures, the distal tip region of both jaws (first and second) may be rounded and atraumatic so that they do not readily penetrate or cut the tissue. However, in some variations, the distal tip region of a jaw is tissue penetrating, allowing the jaw to be inserted into the tissue. In particular, it may be beneficial to have the axially slideable jaw (e.g., the second jaw) be tissue penetrating so that it can be extended into the tissue. This may allow the suture passer to pass a suture in an angle within the tissue (including at a right angle, e.g., to form an approximately "L" shape).

A mentioned above, it may be beneficial to minimize the height of the distal end, and particularly the lower jaw and/or upper jaw at the distal end of the device. It may also be beneficial to reduce the height of the elongate body of the device. Described herein are designs configured to provide minimal height to the elongate body and/or lower and/or upper jaw.

For example, in some soft tissue repair situations, getting access into tight spaces is necessary for accessing the soft tissue requiring repair and for preserving the tissues adjacent to the repair site. An example is a torn meniscus where the knee ligaments can limit the space between the femur and tibia to as little as 3.5 mm. The femur and tibia are covered in cartilage which must be preserved in order to maintain proper joint health. Therefore a suture passer that has a shaft height of 3.5 mm or less provides significant clinical utility to the surgeon. In a suture passer embodiment that contains a sliding lower jaw, as described above, the minimum height is dictated by minimizing specific dimensions. For example, FIG. 43A shows a cross-section through a variation of a suture passer having a sliding lower jaw. Exemplary dimensions that contribute to the overall device height include: the height of the lower jaw 4305 in order to contain the needle pathway, the height of the needle shaft 4311, the height of the clamp rod 4309, the height of the shaft 4307 necessary to maintain appropriate strength, and the height of the clamp link 4313. These heights are illustrated in the enlarged views of the lower jaw (FIG. 43B), elongate body (FIG. 43C), and clamp link 4306 region (FIG. 43D). Even a small reduction in any of these heights, without sacrificing the performance parameters, may provide substantial gains in how and where the suture passer may be used.

For example, in one variation, a number of architectural changes may be made that facilitate a shorter overall height of the instrument. First, the lower jaw pathway may be truncated so that the arc in the lower jaw does not turn fully to 90 degrees, as previously described. See, e.g., FIG. 43B. If, instead, the needle may be configured to exit the lower jaw at a shallower angle (<90°, such as approximately 80°, approximately 70°, approximately 60°, etc.) while still contacting the upper jaw in a region sufficient for deflection distally to pass the suture as described above.

In some variations, a structural portion of the shaft that connects the two sides of the shaft together has been moved from the top to the bottom. This change is facilitated by breaking the lower jaw into two pieces, a first (e.g., distal) end part that contains all of the features of the needle pathway, and second (e.g., proximal) part that serves to translate the position of said distal end. The second, more proximal, piece is not as tall as the distal piece so that it can nest within the shaft. The jog in height is shown in FIG. 44. In this example, the distal end 4407 of the lower jaw contains the needle pathway, while the proximal end 4405 include the strucutre spine of the shaft. The transition between the two 4409 allows for a very flat profile.

In some variations, the height of the needle shaft and clamp rod are reduced. The clamp rod may move to actuate the hinged upper jaw. For example, the clamp rod 4501 may be made flat and attached to the shaft 4509 using a tongue-in-groove configuration while communicating through the open top in the shaft 4509, as illustrated in FIG. 45A. The needle shaft 4503 passes below the clamp rod over this protion of the elongate body. The lower jaw translation shaft 4505 is a U-shaped element within the shaft 4509 that partially surrounds the needle shaft 4503. The combination of these features minimize the amount of material needed to keep the necessary strength and rigidity.

Figure 45B:
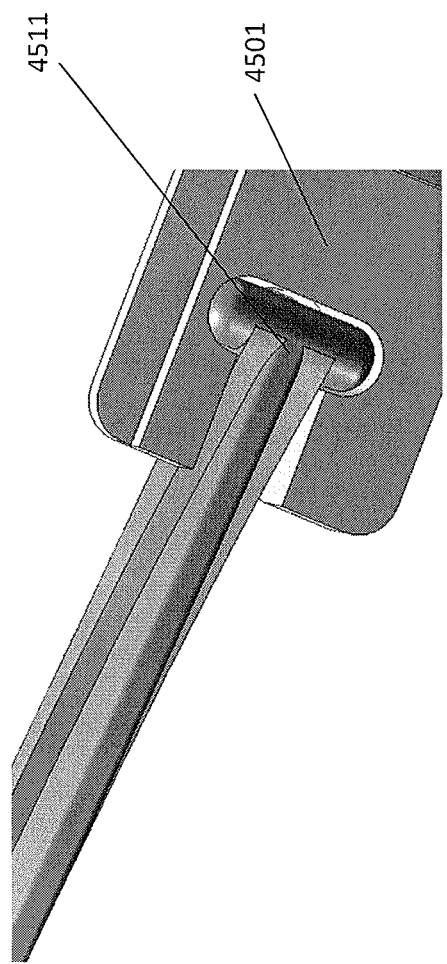
Figure 46A:
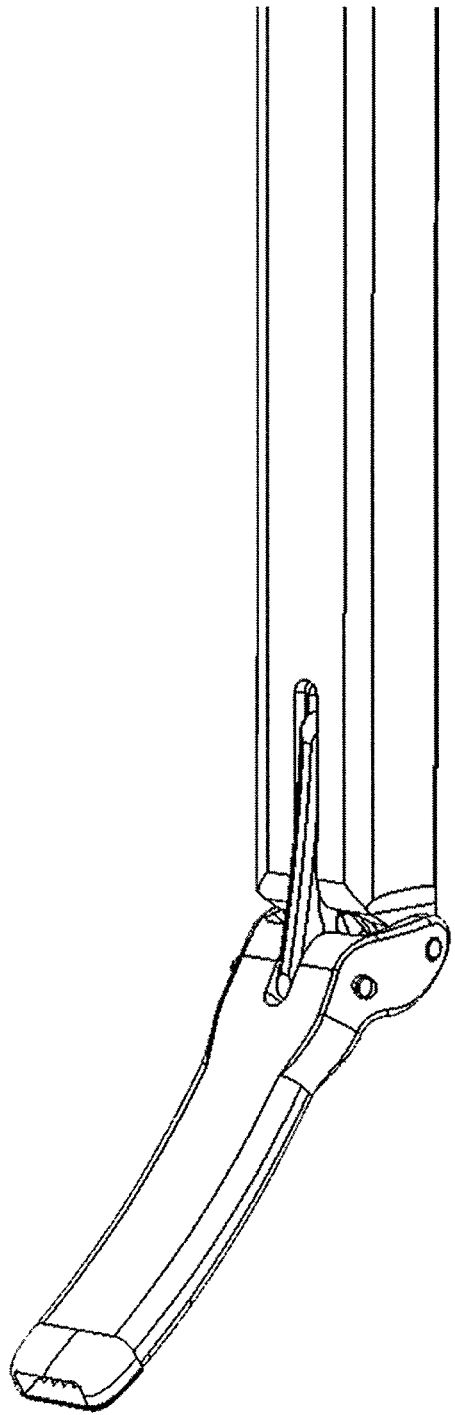
FIGS. 46A and 46B show examples of suture passers having full elongate body housing (FIG. 46A) and a partial or c-shaped elongate body housing (FIG. 46B) from a top perspective view.
Figure 46B:
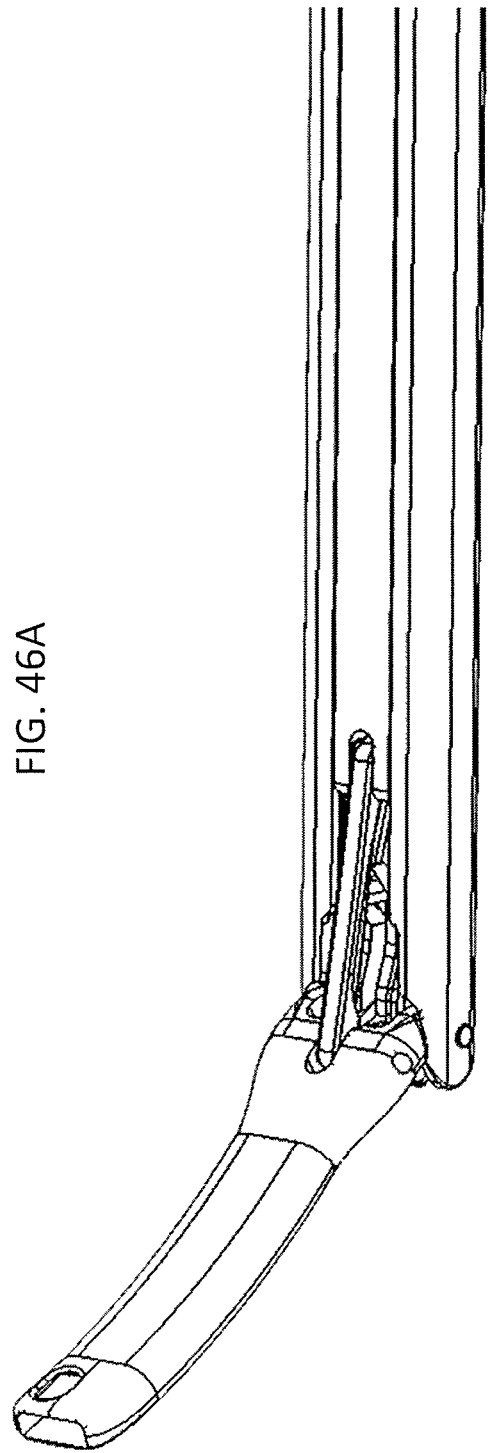
Figure 47A:
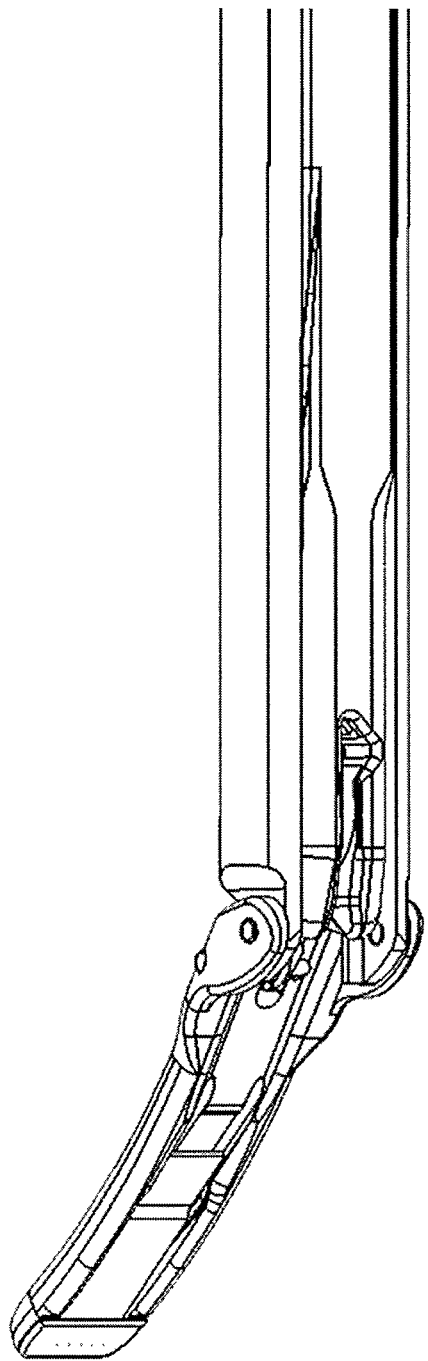
FIGS. 47A and 47B show bottom perspective views of the same suture passers of FIGS. 46A and 46B, respectively.
Figure 47B:
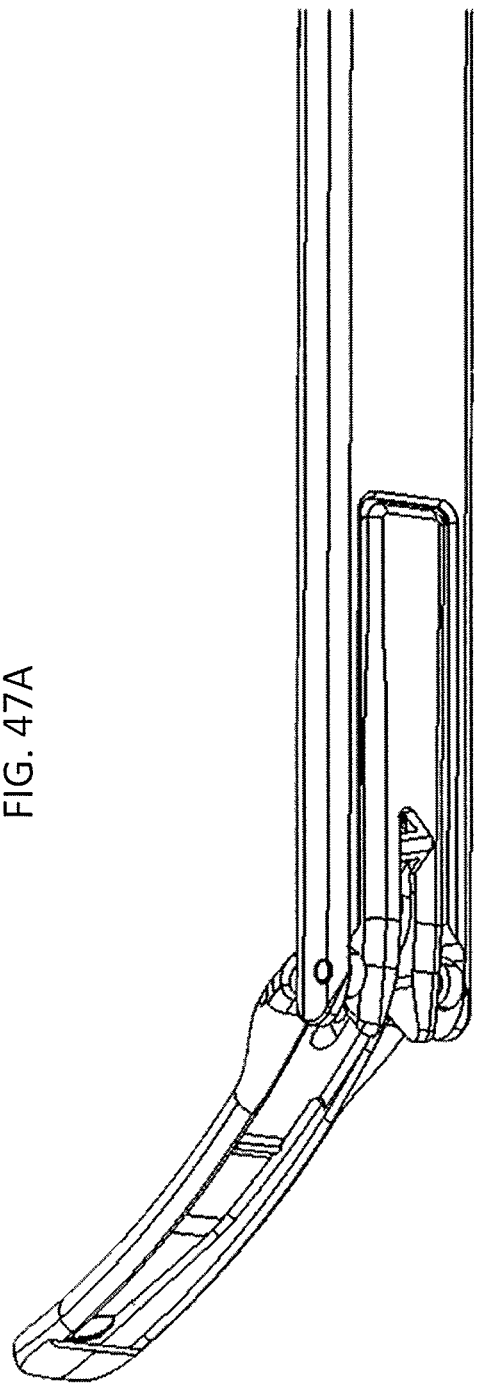

In some variations, the clamp link (which contributes to the hindged motion for the upper jaw) is changed from having two holes with pins through them as shown in FIG. 6D to an alternate design that replaces the more proximal hole with a pin that is integrated into a the clamp link such that it mates with the clamp rod in a the manner shown in FIG. 45B.

Thus, any of these features may be combined to reduce the height of the suture passer devices having an elongate shaft, as shown. For example, the elongate body may have a U-shaped cross-section. The upper jaw actuator ("clamp rod") may be coupled to the hinge (clamp link) via a recessed connection within the footprint of the elongate shaft at one end, and within the upper jaw at the other end, as shown in FIG. 45A. Further the lower jaw member may include a distal region that controls the needle actuation and a proximal region that includes the linear actuating components.

FIGS. 46A-46B and 46A-47B compare a device that does not include the U-shaped outer housing and recessed hinge (FIGS. 46A, 47A) with a device that does (FIGS. 46B, 47B) in top (FIGS. 46A-46B) and bottom (47A-47B) perspective views.

Passing a Loop of Suture Through Tissue

Any of the suture passers described herein may be used to pass a suture in a loop though tissue, so that the ends of the suture can be approximated (e.g., tied together, anchored, etc.). In some variations the suture passer may be loaded with a first length of suture, the first length of suture passed through the tissue, then the suture passer can be reloaded with a second length of the suture and repositioned, and the second length of the suture can then be passed through the tissue again.

Figures 28A, 28B, 28C, 28D, 28E, 28F, 28G, 28H:
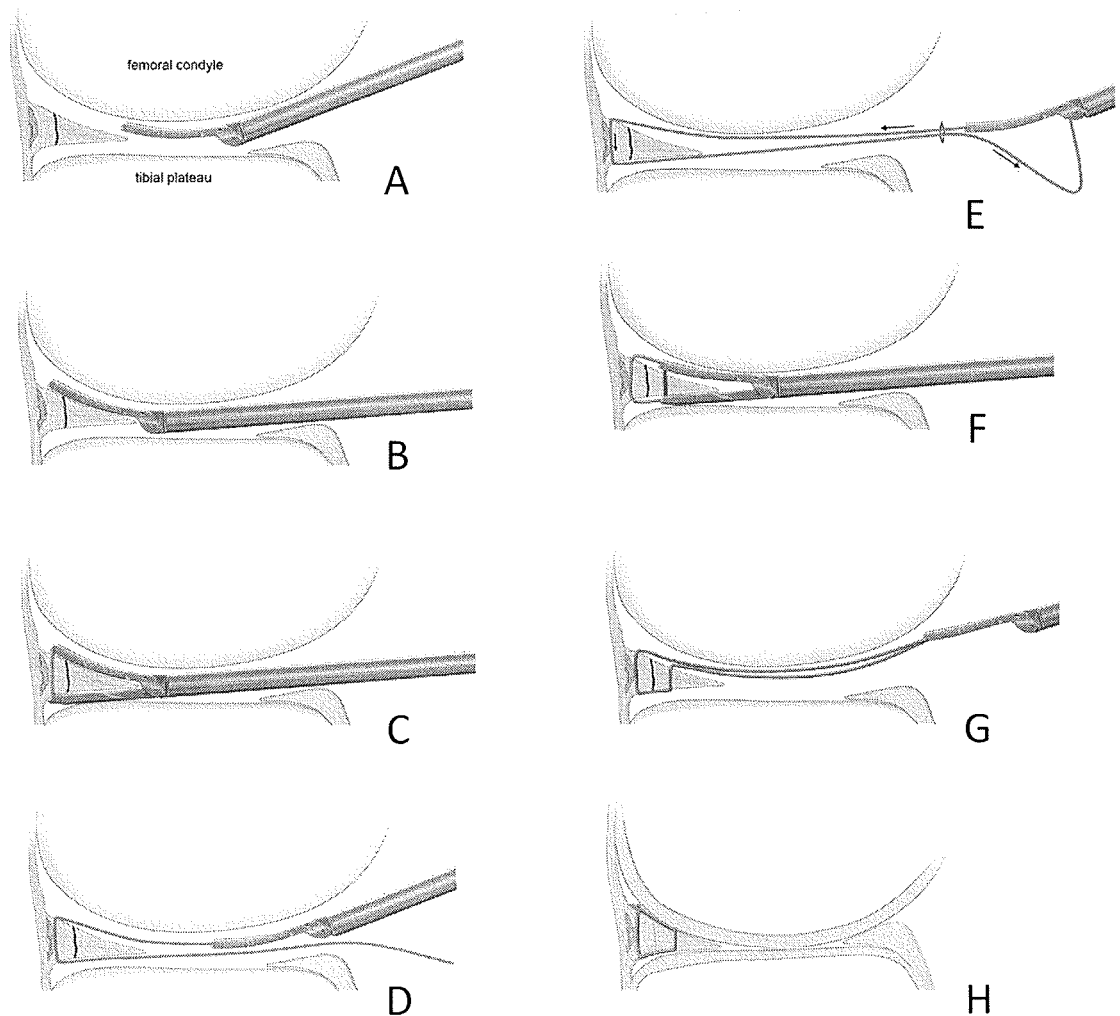
FIGS. 28A-28H illustrate use of a suture passer described herein to form a loop around a target tissue.

For example, FIGS. 28A-28K illustrate on method of forming a loop through tissue in a meniscus using a device that only passes a single length (e.g., bight) of suture. As illustrated, a suture passer can be inserted through a working portal and advanced until the upper jaw is between the superior surface of the meniscus and the articular surface of the femoral condyle (FIGS. 28A-B). The lower jaw is then extended forward so that it moves under the meniscus and the tissue penetrator (needle) trigger is actuated to complete the peripheral pass of the suture from the lower jaw to the upper jaw where it is atraumatically self-retained (FIG. 28C). The lower jaw is retracted and device is removed (FIG. 28D). The suture passer is then re-loaded with the opposite suture strand and re-inserted while gently pulling on the suture such that the upper jaw is lead into the exact same tissue plane (FIG. 28E) the suture is again passed from lower jaw to upper jaw, this time positioned on the opposite side of the tear (FIG. 28F), and the lower jaw is again retracted and the device removed (FIG. 28G). A knot can then be tied on the peripheral femoro-synovial junction (shown in FIG. 28H). No cannula or sled is required for this technique, and the method avoids tissue bridging that can occur if the suture re-enters the tissue in a slightly different location.

As described above, the suture passer may be adapted so that the device does not need to be withdrawn out of the tissue to be loaded with the second suture, including pre-loading the first and second (or more) lengths of suture. In addition, or alternatively, the suture passer may be adapted so that the tissue penetrator (needle) is adapted for both pushing a suture from the lower jaw to the upper jaw and pulling suture from the upper jaw back to the lower jaw (or vice-versa).

The suture passer devices described herein may be configured so that the end of the suture, or a suture linked element connected to the suture, is first pushed by the tissue penetrator through the tissue from the first (e.g., lower, axially moving) jaw to the second (e.g., upper, bending) jaw, then the device is moved relative to the tissue and the tissue penetrator is then extended to collect the end of the suture or the suture linked element, and retracted back through the tissue to pull the suture back through the tissue. Thus, a full stitch may be passed through the tissue. In the meniscus, the full stitch may be passed within the joint capsule without removing the device between passes.

An exemplary sequence of operation is as follows: with a suture loaded onto the device, the device is inserted into the joint capsule and place the device in position for the first pass; pass ("fire") the first leg of the suture; move the device to the second location; fire the device to retrieve the suture, and remove the device from the joint capsule. The suture can then be released from the device and the knot tied (closing the suture loop). This method and devices for implementing it may be referred to as "push/pull" since one end of the suture is first "pushed" through tissue by the needle and captured in the upper jaw, and it is then moved to the second position, and the needle comes up through the tissue to retrieve the captured end and pulls it back down into the lower jaw.

In a first variation shown in FIGS. 29A-29D, a suture that is loaded into the suture passer containing a suture retaining plate on the second jaw that is configured to releasably hold the distal end of a suture, where the plate is adapted to have a "keyhole" passage 2901 through which the suture may be entered and temporarily retained. In some variations this retaining plate with the keyhole is a stripper plate as shown and described above, but with the addition of the keyhole structure. In some variations the keyhole retaining plate is positioned adjacent to a suture stripper. This keyhole suture retainer on the plate and/or suture stripper has an opening at one end that has a larger diameter than the suture; the passage connecting the edge of the suture (which may have a large mouth 2905 that narrows to the narrower passage) typically has a narrower diameter ($D_p$). The keyhole passage typically includes a bend or bends (elbow region) before opening into the large opening mentioned. The elbow region may retain the suture in this narrow region until the tissue penetrator extends back across to retrieve it, as will be described below. FIG. 29A illustrates one variation of a suture stripper 2901 with such a keyhole passage. This variation may be used with a suture having an enlarged distal end feature, such as a knot, ferrule, or other enlarged region attached to the distal end (or near the distal end) of the suture. One embodiment of this enlarged distal end feature of the suture is an overhand knot tied at the end of the suture. A second embodiment is a plastic or metal part that is overmolded, glued, tied or otherwise affixed to the end of the suture. In this embodiment, the stripper with the keyhole cutout may capture the enlarged region of the suture on the end of the suture. As described above, the adapted suture stripper is attached to the inferior surface of the upper jaw. See, e.g., FIGS. 29A-29C. The keyhole cutout region 2905 is shaped in a fashion that allows it to hold the suture at various states while facilitating release of the suture during the second phase (pull) of the procedure. The keyhole-adapted stripper 2901 may be made from any appropriate material, including plastic or sheet metal.

FIG. 29B shows the distal end of a suture with an upper jaw member that includes the plate having a keyhole opening. In this example, a separate suture stripper 2909 is positioned above the plate with the keyhole feature. A tissue penetrator may pass under the suture stripper and the plate with the keyhole feature and the stripper scrapes the suture off the tissue penetrator as the tissue penetrator retracts. FIG. 29C illustrates a top view of the upper jaw of FIG. 29B, showing the distal end of the jaw, with the opening 2905 into the keyhole region that narrows to guide the suture into the bend/elbow region and eventually to the larger opening. FIG. 29D shows the distal end of the suture passer after the suture with the enlarged distal end feature 2905 has been deposited into the keyhole cutout 2901 of the upper jaw.

FIGS. 30A-30B illustrate operation of the plate with the keyhole cutout feature 3001 and a suture with an enlarged distal end feature 3005. In FIG. 30A, the needle is shown beneath the trap feature (the keyhole cutout 3001), which has been made transparent to show the needle position. The enlarged distal end feature 3005 enters the keyhole cutout through the large opening at the edge. The needle passes the first leg of the suture and the knot at the end of the suture (enlarge distal end feature 3005 of the suture). The needle then retracts, leaving the knot and suture behind, and tension is applied to the suture to locate it securely in the correct position, as shown in FIG. 30B. FIG. 30C shows a side perspective view of the method being applied in a meniscal tear (tissue 3011 with tear 3014). The suture passer may be placed in a second location on the meniscus (e.g., without removing it from the knee joint or having to reload) where the second suture leg is intended to be passed. The needle may then be passed through the tissue, and the angled region 3016 at the tip of the needle pushes the suture into the release pathway of the keyhole cutout region 3001, which is shown as an en enlarged circular region. The release pathway is typically an opening having a larger diameter than the enlarged distal end feature of the suture. The release pathway may also include a channel or ramp on the plate that guides the suture to the enlarged opening. This is illustrated in FIGS. 30G and 30H. FIG. 30H shows the needle just before it picks up the suture on its way back to the lower jaw. FIG. 30I shows the needle with the suture (and enlarged distal end feature 3005) held within the hook region of the needle.

Figure 30F:
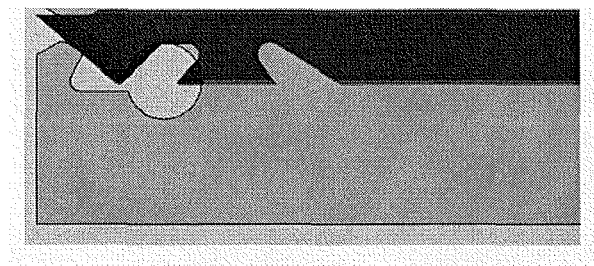
Figure 30E:
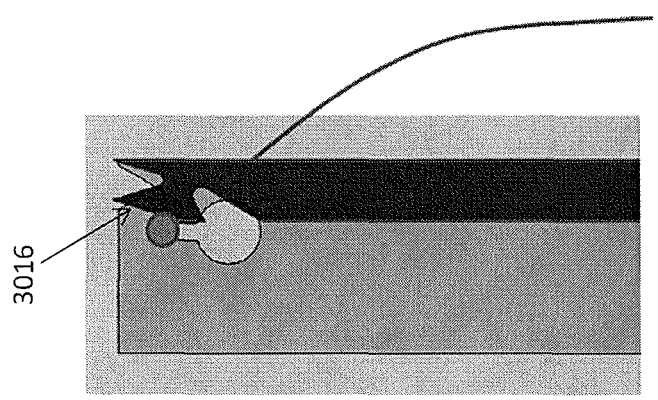
Figure 30D:
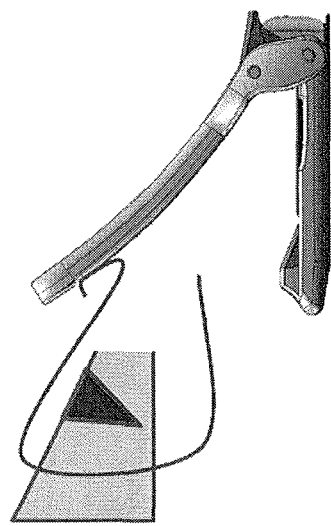

As illustrated above, the needle (tissue penetrator) used for any of these procedures may be adapted to include a suture "pushing" region (hook region, etc.) and a suture "pulling region" (hook region). The suture pushing region is typically located more distally than the pulling region. In FIG. 30E, the needle has a distal-end adapted with a pushing region in which a notch is cut out of the distal end to hold the suture (and enlarged distal end region) as it pushes through the tissue. Proximally along the needle, a hook region, which is oriented so that the hook opening extends distally, is adapted for pulling the suture (and enlarged distal end region) back through the tissue towards the lower jaw. FIG. 30F illustrates another example of a needle in which the pushing region is not at the distal-most end, but is located proximal to the distal end. The needle includes a ramped region at the distal end.

Figure 31A:
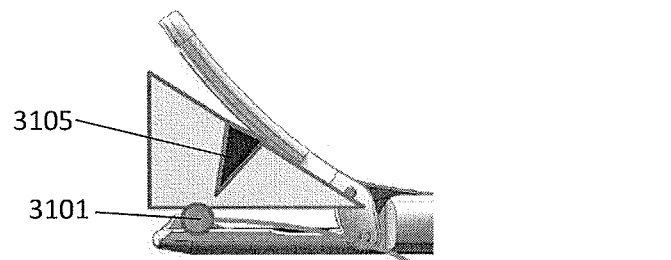
FIGS. 31A-31D illustrate operation of a suture passer as described in FIGS. 30A-30I.

FIGS. 31A-31D show a profile view of the procedure using the keyhole cutout plate and the suture having an enlarged distal end feature. In FIG. 31A the suture passer is positioned around the meniscus, as previously described.

Figure 31B:
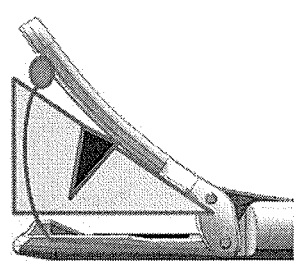
Figure 31C:
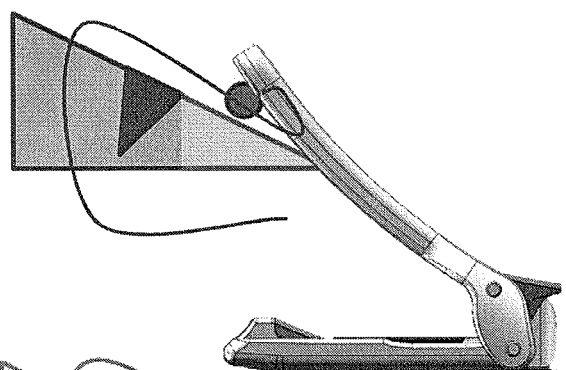
Figure 31D:
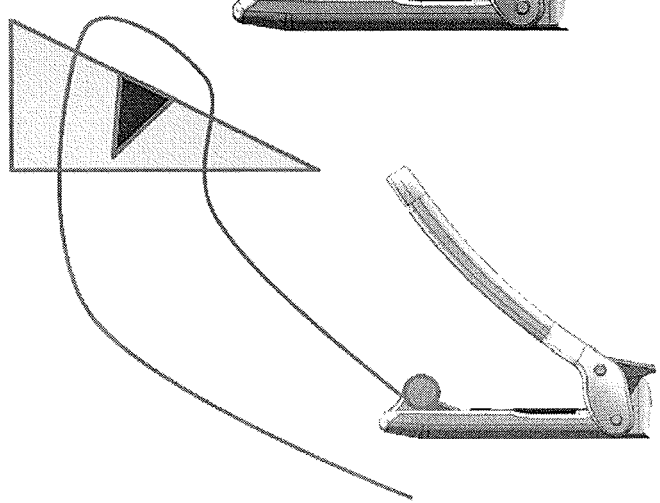

Once the lower jaw is extended, preloaded with the suture with a knot (e.g., enlarged distal end region 3101, not shown to scale), the tissue penetrator may be extended, as shown in FIG. 31B, to push the suture through the meniscus on a first side of the tear in the meniscus 3105. The suture is retained in the keyhole cutout plate, and the suture passer may be repositioned on the meniscus, as shown in FIG. 31C (also not shown to scale). The needle may be extended back through on a second side of the tear (e.g., opposite from the first side), so that the knot is pushed by the returning needle into the large opening of the keyhole cutout plate (not shown) and captured by the pulling hook of the needle and withdrawn back through the tissue with the retracting needle, as shown in FIG. 31D. It should be understood that the terms "needle" and "tissue penetrator" are used interchangeably in this disclosure, though the broader "tissue penetrator" term applies.

Figure 32A:
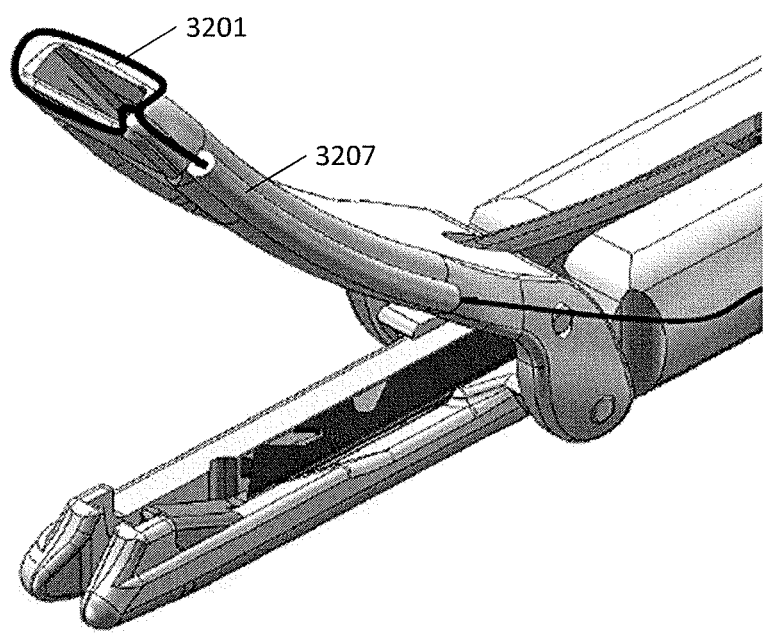
FIGS. 32A-32D illustrate another variation of a suture passer device including suture snaring (grasping) and release feature for passing a suture through a tissue to form a loop around the target tissue.
Figure 32B:
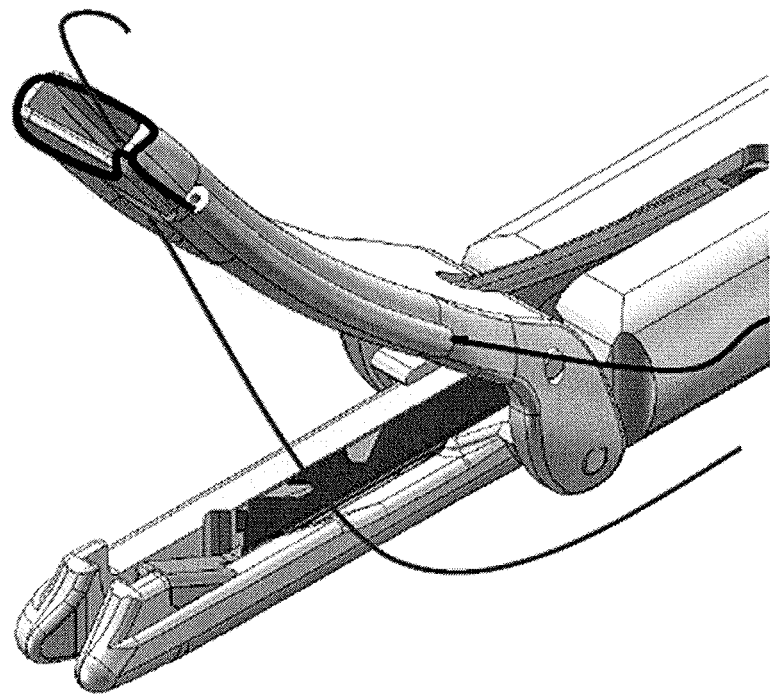
Figure 32C:
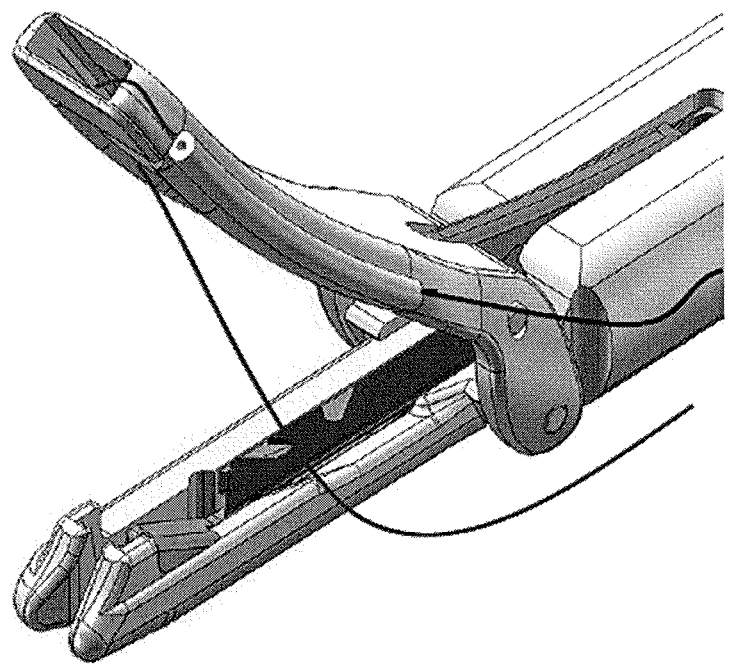
Figure 32D:
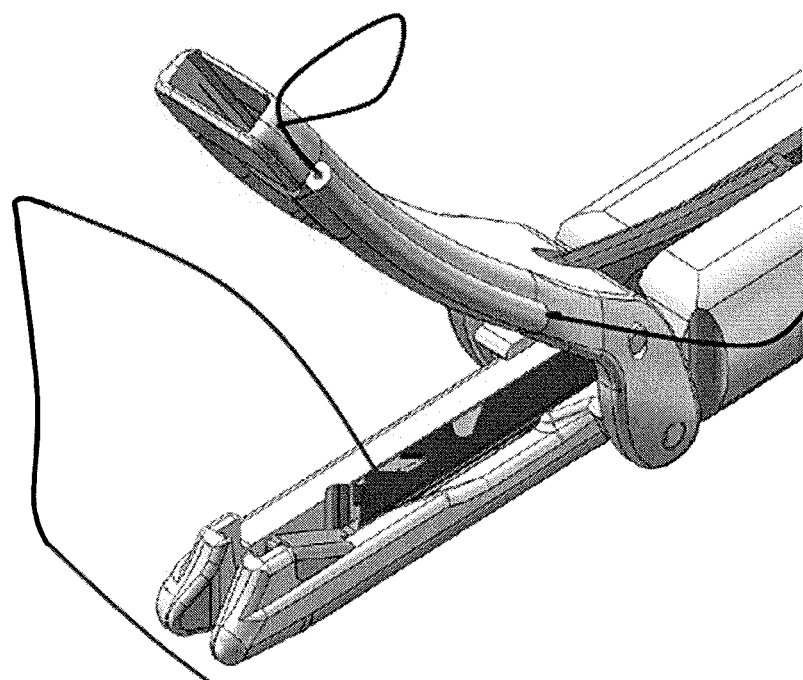

Another variation of a suture passer configured as a push/pull suture passer for forming a loop is shown in FIGS. 32A-32D. In the variation, the device includes a suture passer similar to those described above in FIGS. 5A-6D, but adapted to include a releasable snare. In FIG. 32A, the snare is shown having an open loop 3201 around the distal-facing opening of the upper jaw. The snare may be housed on the side of the device and retractable into this housing (e.g., snare guiding tube 3207). The opening of the snare loop 3201 may be positioned to accept the first leg of a suture. After the first leg is passed, the snare loop 3201 can be tightened and cinch the suture, thereby securing it to the device as it moves to the next position. The loop of the snare may be cinched by pulling the snare proximally so that the loop enters into the housing and closes over the suture, as described below. Once in position, the needle comes up again through tissue to retrieve the suture. The snare then then release, and the needle may be pulled back through the tissue to the lower jaw. FIGS. 32B-32D illustrate these steps. In this variation, the snare may be a wire snare (e.g., Nitinol, stainless steel, etc.), which runs through tubing alongside of the device. In FIG. 32B, the first leg of the suture has been passed through the tissue (not shown) and up through the snare opening. In FIG. 32C, the snare is pulled so that it retreats into the tunnel (snare guiding tube) along the side of the device, bringing the suture with it, and securing the suture in the closed loop, at least partially held within the narrow constrains of the snare guiding tube, while the device is repositioned. Finally, in FIG. 32D the snare loop may release its hold on the suture by extending the wire snare out of the snare guiding tube. The needle may be "fired" (sent across the tissue to the upper jaw) this time hooking the suture. Since the suture has been released by the snare, the suture is free to be pulled back through the tissue by the tissue penetrator and into the lower jaw.

Figure 33B:
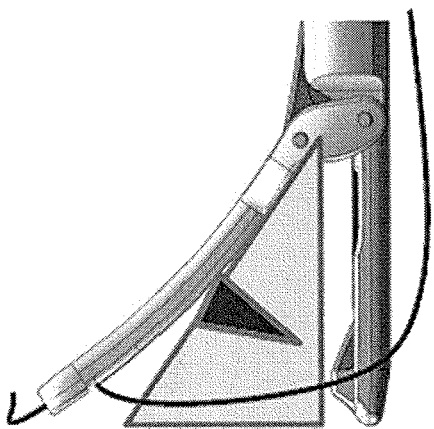
FIGS. 33A-33D illustrate operation of a suture passer as shown in FIGS. 32A-32D.
Figure 33D:
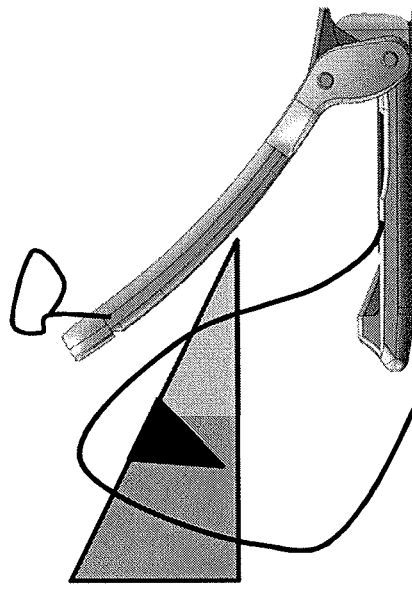
Figure 33A:
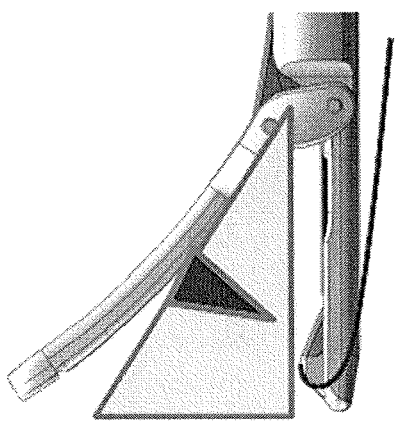
Figure 33C:
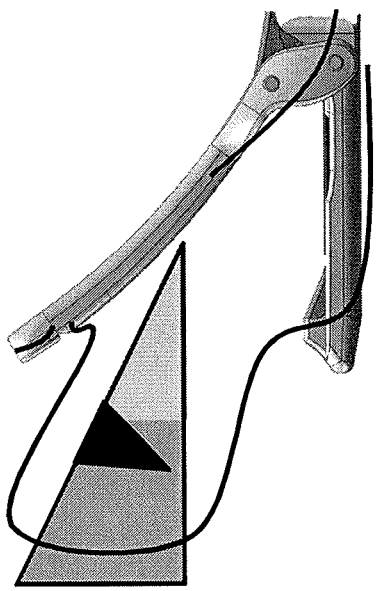

FIGS. 33A-33D show an illustration of this method applied to a meniscus. After positioning the suture passer around the meniscus (shown in FIG. 33A), the suture is pushed through the tissue to the upper jaw, where the suture passes through the snare opening (not shown) and the snare is pulled distally to capture the suture and hold it in the upper jaw while the suture passer is repositioned, as shown in FIG. 33C. Finally, the tissue penetrator is passed through the tissue again, the snare loop is released, and the tissue penetrator hooks and retracts the suture, withdrawing it back through the tissue to the lower jaw (FIG. 33D).

FIGS. 34A-34G illustrate another variation of a system and device for passing a loop of suture through the tissue. In this example, the suture is coupled at or near its distal end with an expandable capture element that makes it easier for the needle to recapture the end of the suture and pull it back through the tissue after it has already been passed through the tissue a first time. The capture element is typically expandable and collapsible, so that it present a small profile within the suture passer and/or within the tissue as it is being passed, but expands or opens to form a relatively large, and easy to capture profile once it has been passed through the tissue a first time. The suture passer may be adapted to hold and grab the expandable capture element. The capture element may be connected to a suture in any appropriate manner, including by tying, gluing, crimping, etc.

Any appropriate capture element may be used, including loops, baskets, coils, etc. The capture element may be flexible, and may be formed of metal, plastic, or the like. For example, in some variations the capture element is formed of a Nitinol wire. A flexible loop or basket (e.g., made of Nitinol), may be used to connect to the suture and be passed by the tissue penetrator which can grab the capture element in order to make a complete circle around a tear. The capture element, connected to the suture, would then shuttle a suture in its place through the tissue.

Figure 34A:
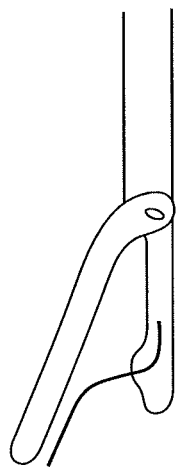
FIGS. 34A-34G illustrates a suture passer device and suture capture element passing a suture twice through a target tissue to form a loop of suture around the target tissue.

FIG. 34A shows an example of a suture passer that may be used, with the tissue penetrator extended. The tissue penetrator may be similar to that shown in FIGS. 5A-6D. In some variations the tissue penetrator is adapted to hold and release a capture element coupled to a suture in the lower jaw, and to allow the capture element to expand when released into the upper jaw. FIGS. 34B-34G are simplified illustrations of a method of forming a loop of suture around a tear in a meniscus (lateral tear 3409). For simplicity, the upper and lower jaws (which are extended around the meniscus) are not shown in FIGS. 34B-34G, although the suture, collapsible capture element and tissue penetrator are shown. In FIG. 34B, the suture passer is preloaded with the expandable capture element, and pushes it through the meniscus, from the inferior to the superior side. Once passed, the tissue penetrator retracts back through the meniscus to the lower jaw, and the collapsed capture element is free to expand. In FIGS. 34B-34G the capture element is a loop of wire that is biased open; as the tissue penetrator retracts back to the lower jaw, as shown in FIG. 34C, the loop expands open on the superior side of the meniscus. The capture element in this example is large enough to expand across the tear in the meniscus; the anatomical constraints of the tissue around the meniscus allow the expandable capture element to expand only on the superior surface in the predictable direction. Because the tissue penetrator pushed distally (up the superior surface of the meniscus) the loop expands in this direction. Re-orienting the suture passer may allow it to direct how and where the expandable capture element expands.

Figure 34D:
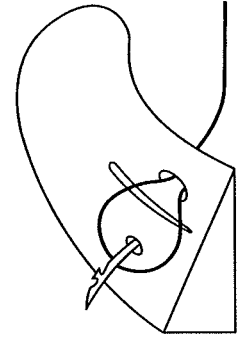
Figure 34C:
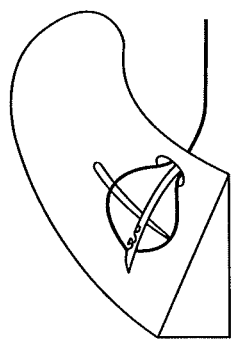
Figure 34B:
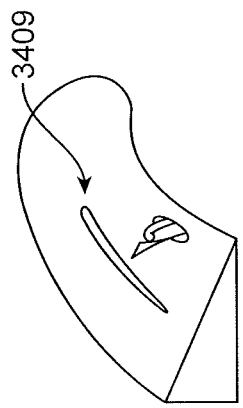
Figure 34G:
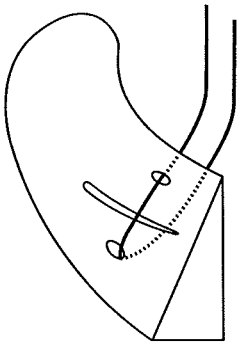
Figure 34F:
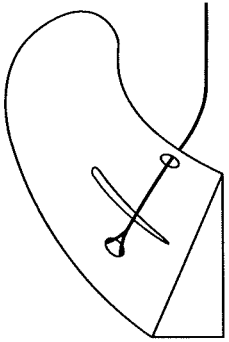
Figure 34E:
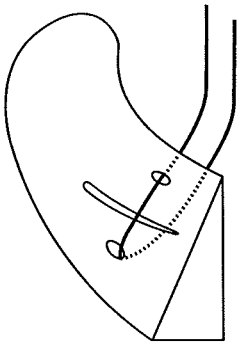

In FIG. 34D, the suture passer has been repositioned relative to the tear in the meniscus, so that the tissue penetrator may pass on the opposite side of the tear, as illustrated. The tissue penetrator extends out of the superior side of the meniscus and though the loop of the capture element. In FIG. 34E, the proximal end of the suture (which is attached distally to the capture element) is pulled proximally to tighten the loop around the tissue penetrator. The tissue penetrator is then retracted, pulling the capture element with it, as shown in FIG. 34F. As the capture element is drawn through the tissue, it again collapses. Once it has been withdrawn through the tissue, pulling the suture behind it, the capture element may be removed, and the ends of the suture secured, as shown in FIG. 34G.

In the example shown in FIGS. 34A-34G, a single tissue penetrator is shown placing the loop and then retrieving the loop. An alternative embodiment could have a lower jaw that contains two tissue penetrators (e.g., needles), one for placing the loop and another for retrieving the loop. Additionally, a third embodiment could contain two independent lower jaws, each containing its own needle. As in the second embodiment, one needle would place the loop and the other needle would retrieve the loop. By placing the needles in separate lower jaws, the two lower jaws could be independently actuated to allow the surgeon to adjust the distance between the two vertical legs of the stitch.

Figure 35A:
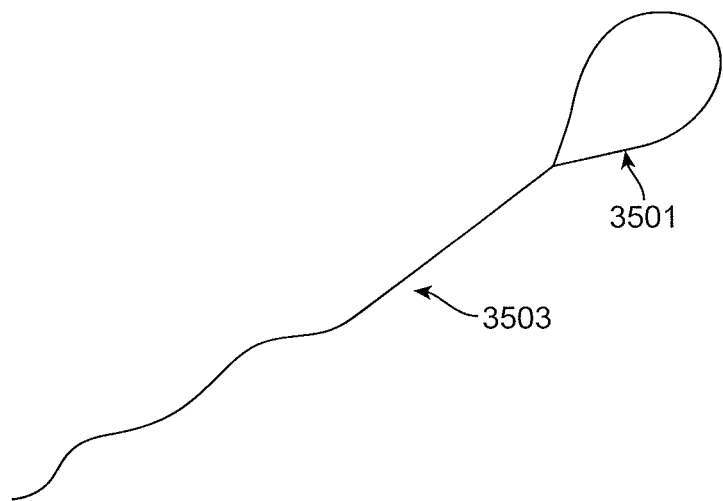
FIGS. 35A and 35B illustrate variations of suture capture elements as described herein.
Figure 35B:
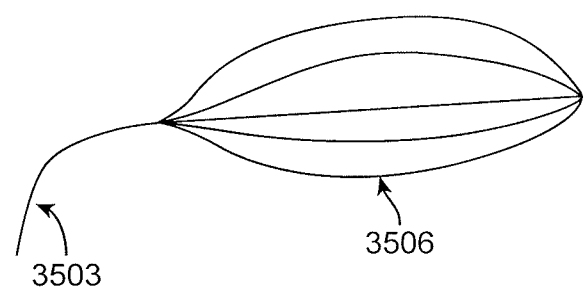

FIG. 35A shows one variation of an expandable capture element that is connected to a suture. In this example, the expandable capture element is configured as a nickel-titanium (e.g., Nitinol) wire that forms a loop but is biased in the open configuration. The suture 3503 is connected to the loop 3501 (either directly or through a leader); for example, the suture may be tied to the flexible loop. FIG. 35B shows another variation of an expandable capture element, configured as a plurality of loops 3506 that are flexible but biased open (expanded). A suture 3503 may be affixed to the plurality of loops ("basket") 3506. The plurality of loops may help ensure that the tissue penetrator hook (e.g., pulling hook) catches the capture element; this feature may alleviate the need to cinch the suture (e.g., pull the suture proximally).

In some variations the expandable capture element is not extended substantially from the upper jaw member, but remains within the jaw member and is held by the upper jaw member after withdrawing the tissue penetrator so that when the tissue penetrator is again extended through the jaw, the tissue penetrator will pass through it, and the capture element can be pulled onto the tissue penetrator to engage with it so that it can be withdrawn back through the tissue.

Figure 36A:
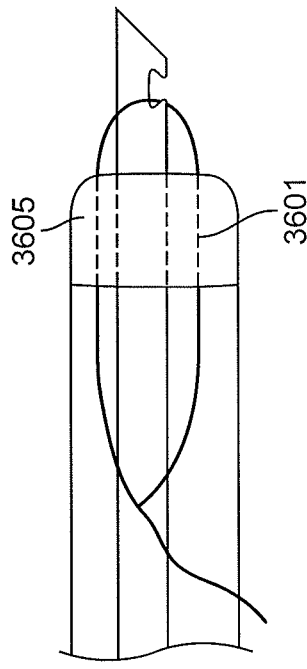
Figure 36B:
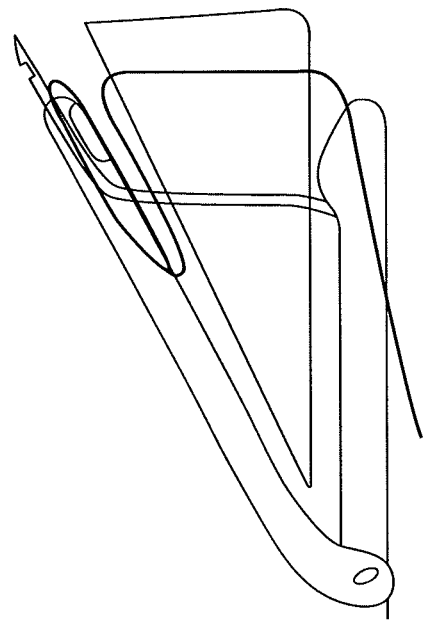
Figure 36C:
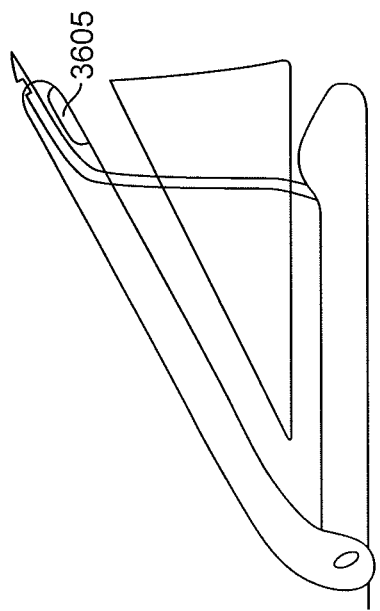
Figure 36D:
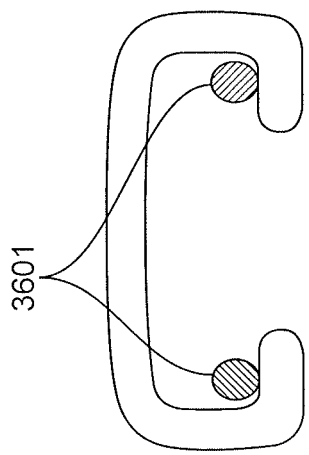

FIGS. 36A-36C illustrate this variation. In FIG. 36A, the tissue penetrator has an upper jaw member that includes a holding region 3605 for the capture element; in FIG. 36A, the holding region is defined on the underside of the upper jaw by a retaining plate 3605, as also illustrated in FIG. 36B. The Nitinol loop 3601 is pushed by the needle so that the expandable capture element expands into the space under the upper jaw defined by the plate, as shown in FIG. 36B. The holding region may be defined by the upper jaw so that the capture element (e.g., loop) is held with an orientation that prevents the capture element from engaging with the needle when it is pushed fully distally. FIG. 36C shows a section through the holding region of the upper jaw, where a capture element 3601 is being held. After retracting the needle and repositioning the device, the needle/tissue penetrator can again be extended through the tissue and into the upper jaw, as shown in FIG. 36D. The needle may pass through the loop of the capture element held in the upper jaw. The suture may then be pulled proximally, reorienting the capture element and pulling it onto the needle so that it engages the needle and is pulled back through the tissue when the needle is withdrawn back though the tissue. This is illustrated in FIG. 36E (showing cinching of the loop of the capture element) and FIGS. 36F-36H, showing the capture element being withdrawn back to the lower jaw. In FIG. 36E, the suture 3603 is pulled to cinch the loop of the capture element onto the needle. In FIGS. 36F and 36G, the needle 3615 is shown capturing the loop of the capture element 3601. Finally, FIGS. 36H and 36I show the tissue penetrator completely withdrawn (holding the capture element) into the lower jaw (FIG. 36H), and the device being withdrawn from the tissue, as shown in FIG. 36I, which pulls the rest of the collapsed loop from the meniscus, and pulls the suture into position.

Figure 37A:
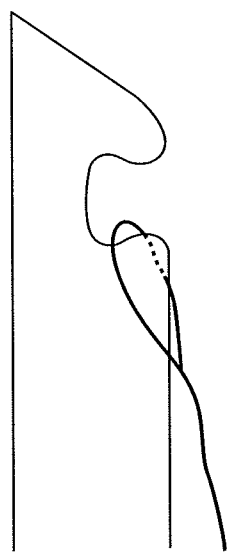
FIGS. 37A and 37B show alternative suture capture elements engaging a tissue penetrator.
Figure 37B:
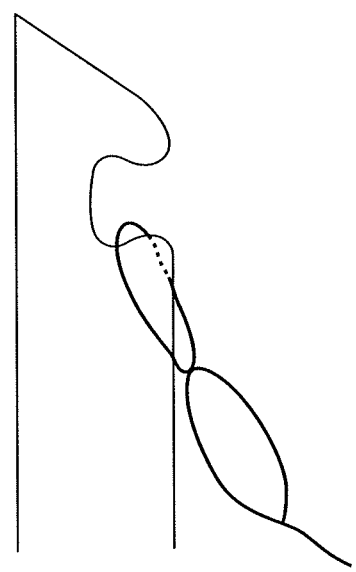

FIGS. 37A and 37B illustrate variations on the interaction between the capture element and the tissue penetrator. In FIG. 37A, the tissue penetrator couples with a loop of the capture element; thus the flexible loop can be preloaded onto the tissue penetrator before it is retracted into the lower jaw and primed to "fire" across the tissue. In some variations it may be beneficial to have the capture element be coupled to the tissue penetrator via a loop of suture material or other material that does not self-expand, such as the expandable capture element does. This may help with pre-loading the capture element onto the tissue penetrator, and may also help in reducing the force needed to pass the capturing element through the tissue. FIG. 37B illustrates one example in which a loop of suture is connected to the capture element that is also connected to a length of suture, as shown.

Enhancing Suturing Accuracy

Although the suture passers described herein may be used to pass sutures though tissue (and particularly meniscal tissue) having various thicknesses and dimensions by adjusting the bite (e.g., the angular distance between the upper and lower distal-facing jaws), adjusting the bite size may change the contact position of the needle/tissue penetrator as it extends from the lower jaw to the upper jaw. Note that in any of the variations described herein, the lower jaw may refer to either the first jaw or second jaw, as the orientation may be relative; similarly the upper jaw may refer to the opposite jaw, in any orientation. Although the devices describe herein are configured so that the devices tolerate changes in the contact point between the needle and the upper jaw, while still deflecting the needle distally as described above, it may be beneficial to know where on the upper jaw the needle will exit the tissue and contact the upper jaw. This may be referred to as targeting. It may be relatively less certain where the needle may exit the tissue when the bite size of the needle is smaller (e.g., when the jaws are more closed).

Figure 38B:
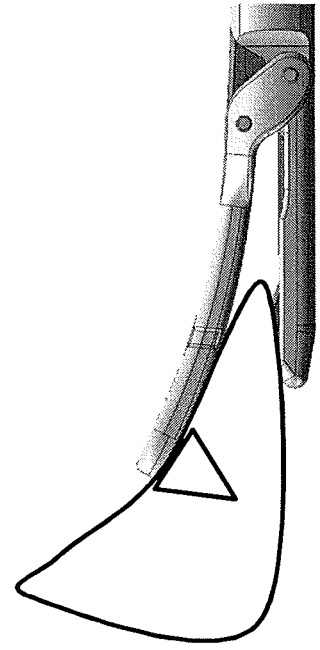
FIGS. 38A and 38B illustrate clamping of tissue (e.g., meniscus tissue) between the jaws of a suture passer.
Figure 38A:
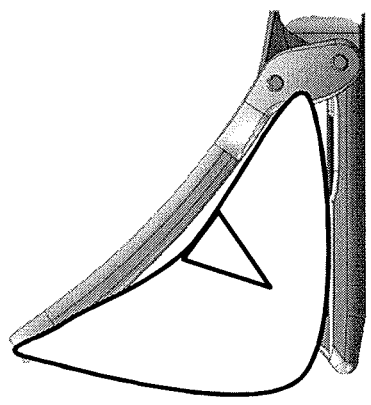

Described herein are methods and devices that allow the user to place a stitch in an intended location even when the jaws are relatively "closed" (e.g., small bite size), as when passing a suture in the more central regions of the meniscus. This uncertainty does not typically arise when placing a stitch at the periphery of the meniscus, when the bite size is relatively large, because the user can position the device as distal as it will go and blindly fire (see FIG. 38A). However, the when a stitch is placed on the middle of the meniscus or near the apex of the meniscus (see FIG. 38B), it is less certain where the needle may exit the tissue relative to the upper jaw. FIG. 38A shows the placement of a stitch near the periphery of a meniscus. A user can just push device past the tear and deliver stitch without worrying about accuracy of where the needle will contact the upper jaw. FIG. 38B shows a stitch near the apex of the meniscus. The surgeon is placing a stitch between the tear and the apex. However if the stitch is placed too close to the apex, the stitch won't grab enough tissue to be secure, too close to the tear and the stitch could be sent up through the tear. When the device is placed in a joint, such as the knee joint, the lower jaw may be completely covered by tissue, and the needle exit is invisible to the user. A stationary mark on the upper jaw is problematic because it may not predict where the needle with exit/hit; the needle may hit the upper jaw in different locations based on clamp height.

Described below are methods and device (e.g., adaptations to devices) that may be used to target stitch placement.

In some variations the lower (sliding) jaw is configured to move conjugally with the clamping of the upper jaw, so as to maintain an approximate relative striking distance between the tissue penetrator and the upper jaw when passing the tissue penetrator across the jaws.

Figure 39B:
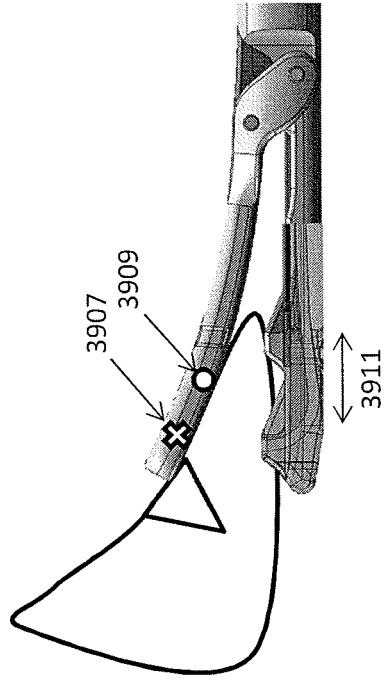
FIGS. 39A and 39B illustrate the contact points of a suture passer with and without conjugate motion when clamping tissue between the jaws of the suture passer.
Figure 39A:
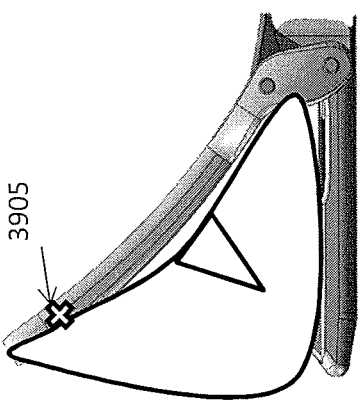

FIG. 39A shows a jaw moving though a large tissue thickness (e.g., a thick meniscus in this example). An exemplary "thick" tissue thickness may be 7.5 mm. At this size thickness, the needle will hit the upper jaw at a given location shown in FIG. 39A by the "X" 3905. Without conjugate motion between the upper and lower jaw (e.g., moving the lower jaw distally/proximally as the upper jaw bends to change the bite angle), the location of this contact point will vary, as illustrated by the more proximal contact point "o" 3909 in FIG. 39B. If, however, when the upper jaw clamps down, the lower jaw would move forward 3911, the contact point may be corrected to ensure that the needle hits the upper jaw in the same location, 3907. In this example, the lower jaw may move to the left 3911, relative to the shaft, to deliver the suture to the "X" target on the upper jaw 3907.

Thus, the suture passer may be configured as described above so that the lower jaw can be moved axially (distally/proximally relative to the elongate axis), both independently (to form the distal-facing opening, and also in conjugate motion when clamping/unclamping the upper jaw to change the bite angle of the suture passer.

In some variations, the movement of the upper jaw and the conjugate motion of the lower jaw can both be controlled by the clamp trigger (refer to FIGS. 5A-5B, for example). As the upper jaw clamps down, the axial distance of the "X" may move at a nonlinear rate distally. In order for the lower jaw to match that axial distance, it may also travel at the same rate. This can be accomplished by having the lower jaw motion controlled by a cam profile on the needle trigger. An example of such a cam profile is shown in FIG. 40.

Figure 40:
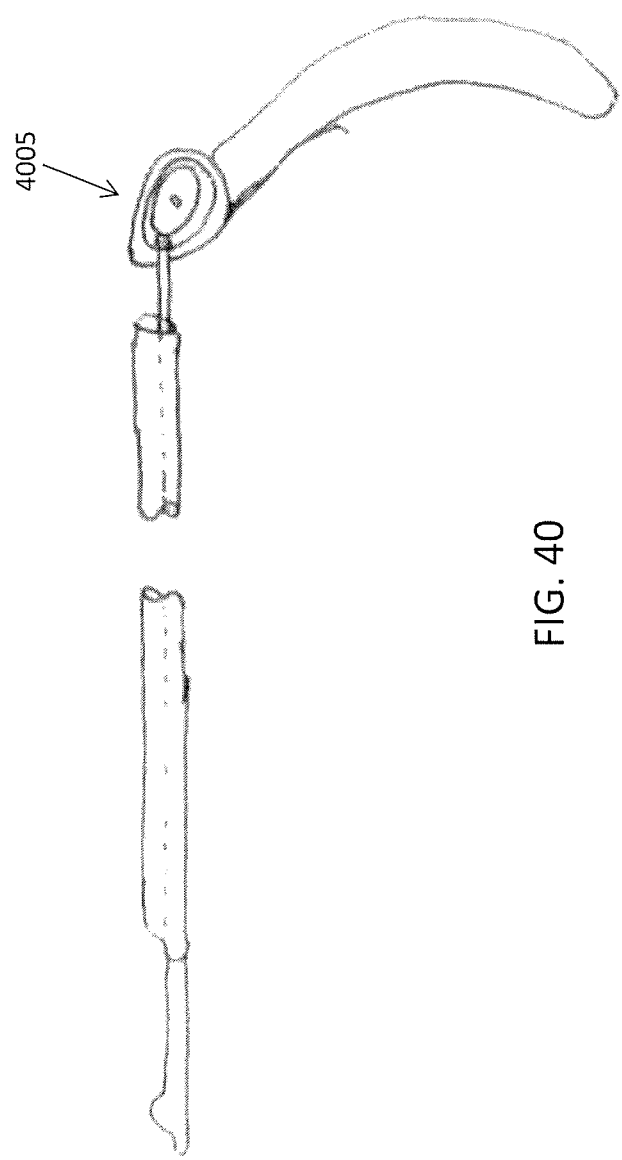
FIG. 40 illustrates a mechanism for achieving conjugate motion between an axial moveable lower jaw and a hinged/pivoting upper jaw.

In FIG. 40, the lower jaw include a cam follower 4005 that includes a camming surface that may also drive axial motion of the lower jaw when the upper jaw is moved. In this manner, motion of the upper jaw may be configured so that the axial position is adjusted based on the angle of the upper jaw with the elongate, long axis, of the device. The lower jaw may still be manually and independently axially movable to extend/retract axially. In some variations the lower jaw moved in conjugate motion with the upper jaw only when the lower jaw member is fully extended first (e.g., manually fully extended). Further, in some variations the conjugate motion between the upper jaw member and the lower jaw member may be turned "on" or "off" for the device.

Figure 41:
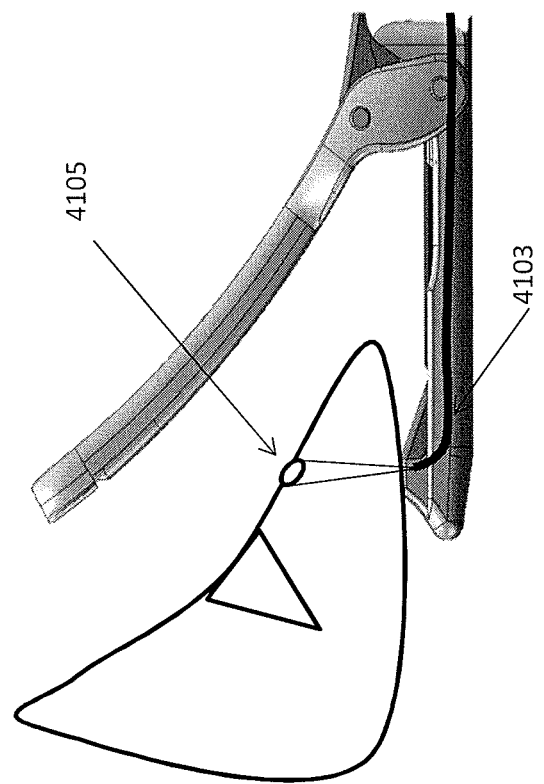
FIG. 41 illustrates operation of a suture passer device including a visual marking/notification element that projects light though the tissue to indicate the path that the needle (tissue penetrator) will take.

Also described herein are methods and devices for informing a user where the tissue penetrator may be passing through the tissue. As discussed above, it may be advantageous to provide an indicator to the operator of where the tissue penetrator (e.g. needle) will exit the tissue. In some variations the device may include an optical marking element (e.g., light) that indicates on the tissue and/or on the device, such as the upper jaw of the device, where the tissue penetrator will exit the tissue or where it will contact the upper jaw. FIG. 41 illustrates on variation of a device including an optical fiber 4103 extending with (and part of) the lower jaw that project a spot of light (e.g., visible or visualizable light) through the tissue. This light may be from an LED, laser, or other appropriate source. For example, a light source is placed on the lower jaw pointing toward the upper jaw to indicate where the needle will exit. In thin sections of tissue, if the light is strong enough, there should be a visible spot on top of the tissue that the user can use to place the stitch with confidence.

Tactile/Audible Feedback

Also described herein are devices configured to provide tactile and/or audible feedback to the user that the lower jaw and/or needle have been fully extended. For example, for certain suture passers, the grip force required to actuate the needle may be great enough that it is difficult for the user to feel the needle trigger's end of travel because the actuation force already placed high demands on the user's grip strength. Thus, it is hard for the user to detect that they are pushing up against something immovable, the travel limiter, because the force required to actuate the needle trigger feels may be great. In these cases, a suture passer device that provides an audible "click" or some other cue is helpful to the surgeon to ensure that he or she has fully actuated the device. For suture passers with slightly lower actuation forces, coupling the audible feedback with tactile feedback, whereby the surgeon feels a click or a detent just prior to the needle trigger hitting its travel limiter, could provide additional assurance to the user that he or she has properly completed actuation.

Figure 42A:
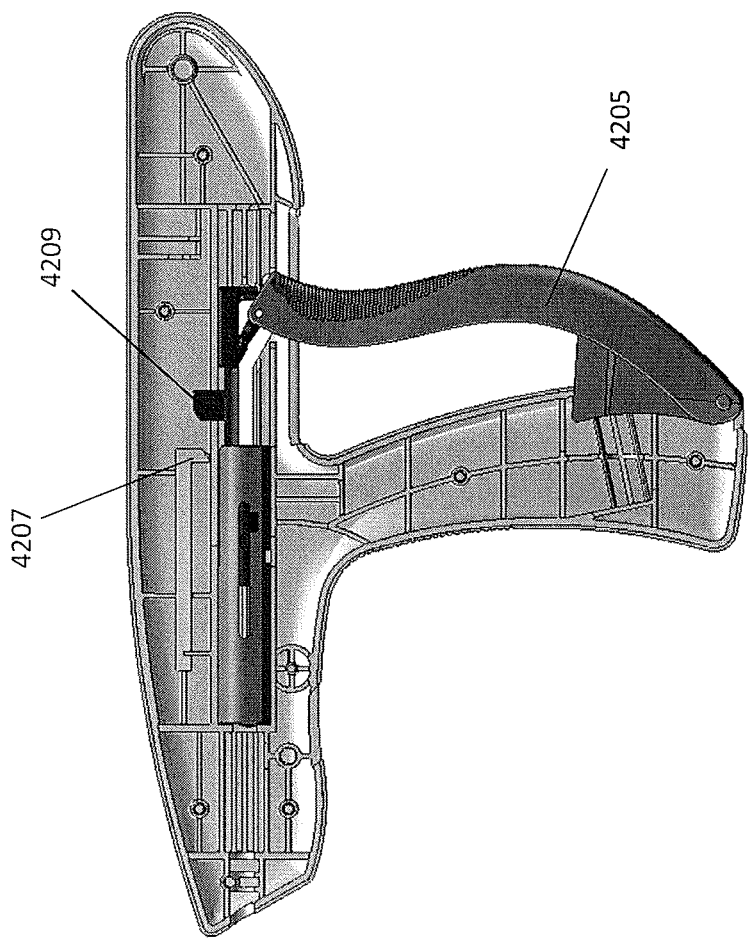
FIGS. 42A-42C illustrate a suture passer device having an audible/tactile feedback indicating the extension of the tissue penetrator.

One method for providing both an audible and tactile cue is shown in FIG. 42A. FIG. 42A shows a cutaway view of the suture passer handle mechanism. In this example, the needle driver 4209 is rigidly attached to the needle (not shown). As the surgeon grips the needle trigger 4205, the needle driver 4209 translates forward. Because it is rigidly attached to the needle driver, the needle also translates forward as the needle trigger is gripped.

Figure 42B:
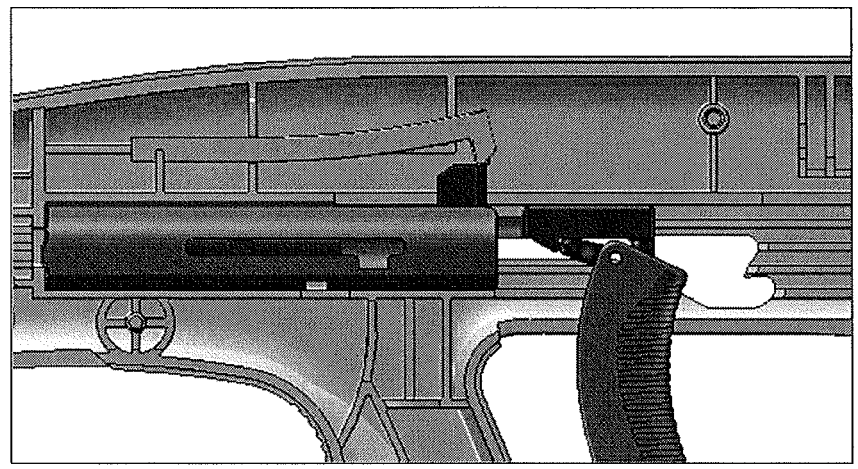
Figure 42C:
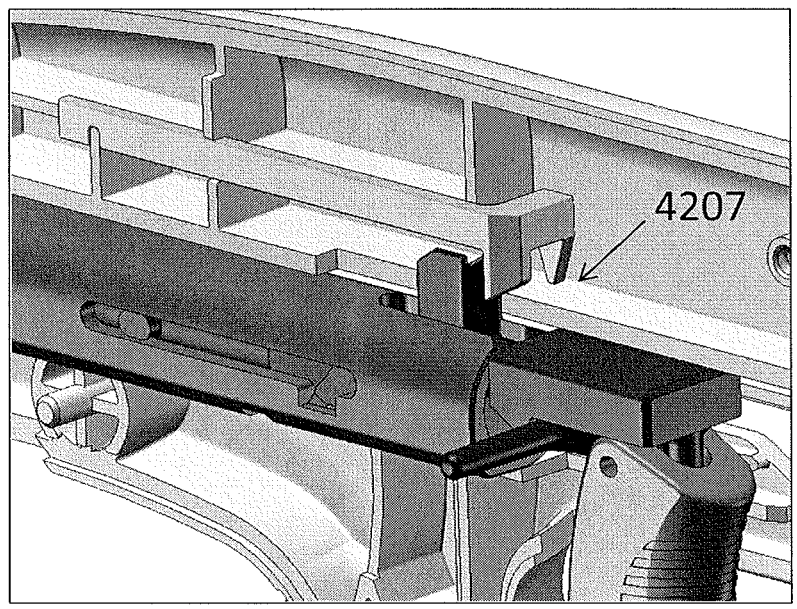

The needle driver contains a boss that, as it moves past a clicking element 4207, bends the Clicking Element upward as shown in FIG. 42B. Once the boss has moved distally past the interfering portion of the clicking element, the clicking element is free to snap back down where it impacts a feature 4215 on the handle (see FIG. 42C). This impact is enough to create an audible click that can also be felt in the user's hand.

Any other appropriate feedback actuator for providing audible and/or tactile feedback at or near the maximum extension of the needle and/or lower jaw may be used. The configuration described above in FIG. 42 is a mechanical feedback actuator; in some variations the system may use one or more optical encoders and a piezo or other electronic technique for providing feedback to the user (e.g., electrical feedback actuator).

Upper Jaw Shape

Figure 48A:
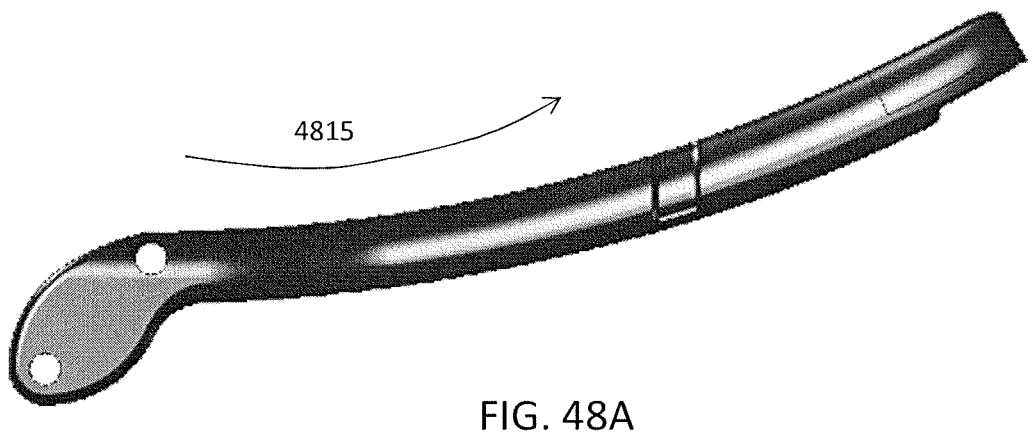
FIG. 48A shows an upper jaw having a radiused (curved) outer surface near the proximal region and a uniform thickness along much of the length.

Any of the devices described herein may include an upper jaw that is adapted to fit within the confines of a joint such as the knee. For example, the upper jaw, which may be hinged relative to an elongate body of the suture passer, as described above, may be radiused (e.g., curved) upwards slightly, particularly over the proximal region of the upper jaw, near the hinge connection. FIG. 48A illustrates one variation of an upper jaw having an upwards curvature 4815 on the outer/upper surface. In the context of the knee joint, this upper jaw member (which may also be referred to as an upper jaw or upper arm) may match the curvature of the femoral region of the joint surrounding the meniscus. Examples of upper jaws including radiused outer surfaces may be see in FIGS. 1A, 1B, 3A, 15A-E, 26C-I, and 29B, for example.

Thus, the upper jaw of a suture passer adapted for passing suture in the knee around the meniscus may be shaped for joint access such that the superior (upper) surface of the upper jaw has a gentle curve that approximates the curvature of the femoral head, as shown in FIG. 48A. An upper jaw with this shape can be easily inserted into the knee joint space so that the upper jaw is superior to the meniscus in order to facilitate suture passing. However, one potential disadvantage of an upper jaw with the shape shown in FIG. 48A is that the convex surface on the inferior side (inner, tissue-contacting surface) may have help push the meniscus distally out of (and away from) the distal-facing opening between the jaws when the upper and lower jaws are closed over the meniscal tissue, as discussed above in reference to FIGS. 38A-39B. This phenomena is disadvantageous when trying to pass a tissue penetrator (e.g., needle) through the meniscus in a precise manner, as it can cause the meniscus to be displaced out of the jaws, and/or may cause the needle to miss the suture retention feature in the upper jaw.

Figure 48B:
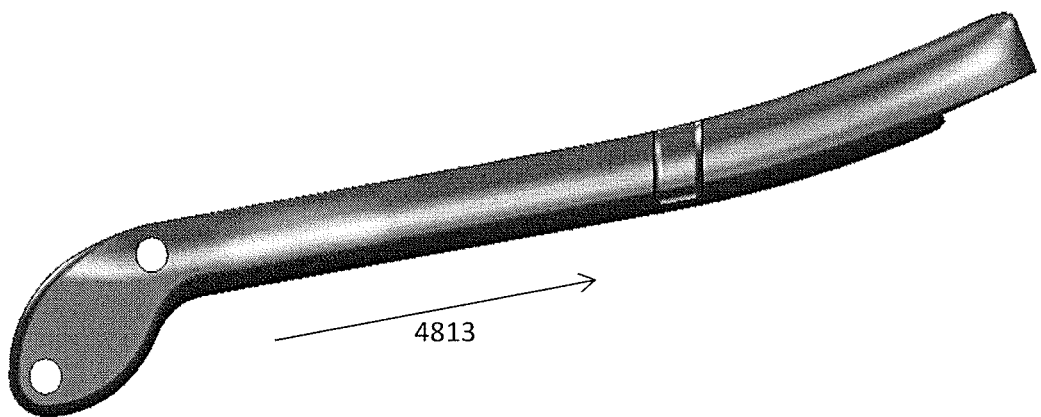
FIG. 48B shows an upper jaw having a straight (uncurved) proximal region and a uniform thickness along much of the length.
Figure 48C:
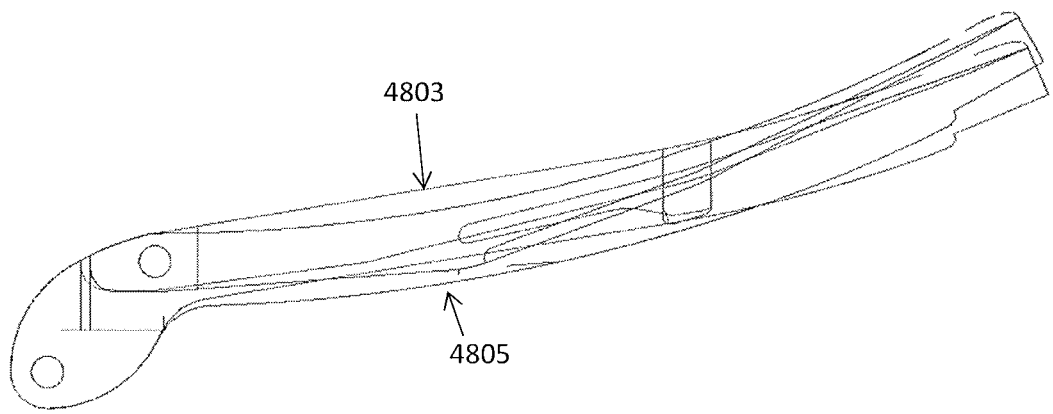
FIG. 48C shows an overlaid view of the upper jaws of FIGS. 48A and 48B, showing the differences in curvature near the proximal end regions.

Although this issue may be addressed, at least in part, by the conjugate motion of the upper and lower jaws described above, a modified version of the upper jaw, having a flat or less curved inferior (tissue-contacting) surface may also address this issue. For example, FIG. 48B shows an upper jaw having a geometry with a straighter profile 4813 in its proximal region (near the hinge). The proximally straight variation shown in FIG. 48B may have a significantly lower propensity for pushing the meniscus out of the distal-facing mouth formed by the upper and lower jaws when the closing the jaws around the tissue, which may help keep the meniscus from being displaced when passing a suture with the device, improving locational precision and suture capture reliability. Unfortunately, this configuration may not be optimally shaped for joint access, because of the overhead constraint of the femur and the lower "slope" of a straight upper jaw. Thus, the distal tip of the upper jaw may be less able to clear the meniscus on the superior side as easily as the radiused outer surface. The differences between the proximally curved upper jaw of FIG. 48A and the proximally straight upper jaw of FIG. 48B are shown in FIG. 48C, showing both upper jaw geometries overlaid on top of each other. In FIG. 48B, the superior surface of the straight upper jaw 4803 is opposite the inferior curved surface of the radiused 4805 upper jaw. When looking at the overlay, the superior surface of the proximally straight upper jaw variation may contact the femoral head sooner than the superior surface of the proximally curved jaw variation. However, when the proximally straight jaw variation contacts the femoral head, its distal end is not as high, and may have less ability to clear a tall meniscus.

Figure 48D:
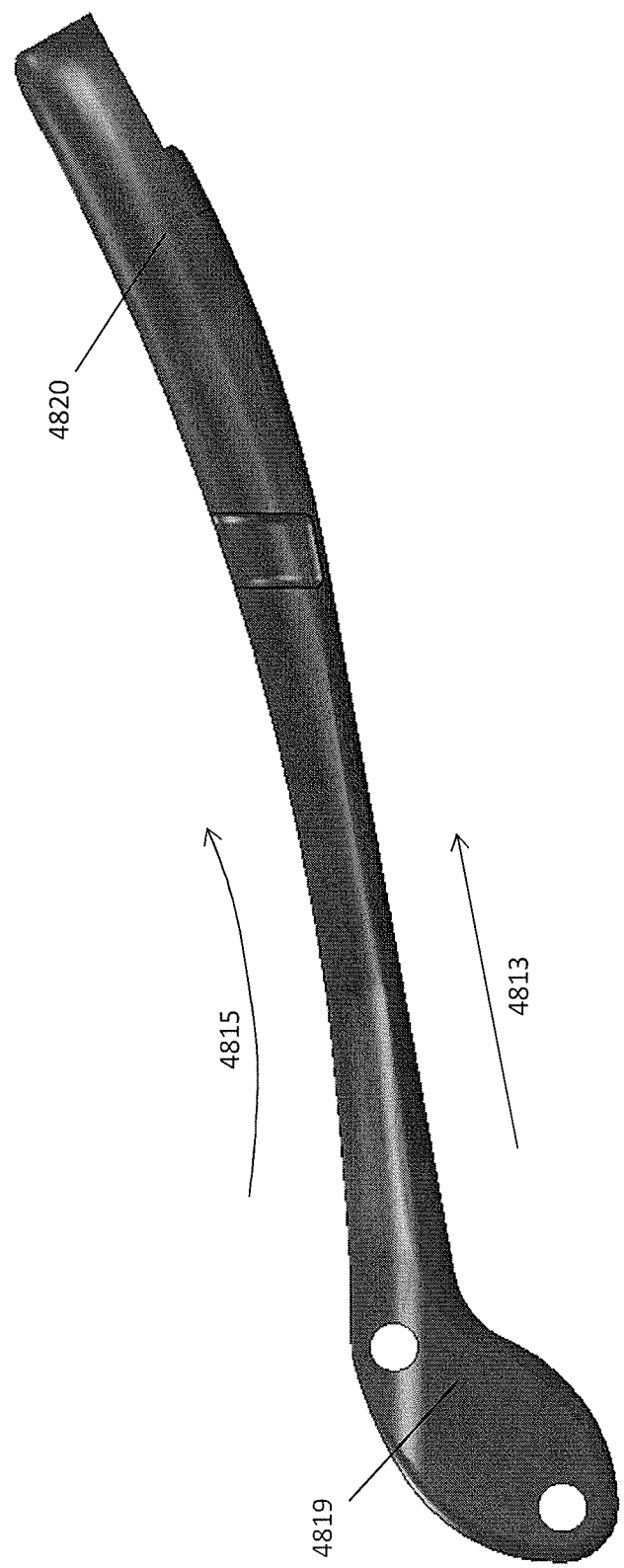
FIG. 48D shows a hybrid upper jaw having a curved (radiused) upper surface and a straight lower, tissue-contacting, surface. The hybrid upper jaw is thinner in width proximally than distally.

FIG. 48D shows a side view of a hybrid upper jaw having both a radiused/curved proximal superior surface 4815 and a straight (or less curved relative to the superior surface) inferior, tissue-contacting surface 4813. In this example, the upper jaw has a thinner proximal region (between the hinge 4819 and the distal region 4820.

The hybrid upper jaw shape adapts the proximally radiused superior surface with the relatively straight inferior (lower) surface; using the profile of the curved upper jaw shown in FIG. 48A for the superior surface and the distal half of the inferior surface, and the inferior profile of the proximally straight upper jaw shown in FIG. 48C. This hybrid profile combines the excellent access shape along with the features necessary to mitigate the probability that the meniscus is pushed peripherally during clamping.

Thus, any of the suture passers described herein may have hinged upper jaw extending in a proximal to distal axis, with a hinge region at or near the proximal end. The upper jaw may have an outwardly curved (radiused) superior surface extending distally from the hinge region. The inferior, tissue-contacting, surface opposite this outwardly curved superior surface may be configured to extend straight in the proximal to distal axis. Thus, the thickness of the upper jaw as it extends from the hinge region distally may be narrower (thinner) more proximally than distally, as shown in FIG. 48D.

Asymmetric Needles

The tissue penetrators (needles) described herein typically have a sharp distal tip that is adapted to penetrate tissue. The sharp distal tip may be located anywhere along the width of the tissue penetrator. For example, the sharp distal tip may be centered relative to the width, as shown in FIG. 7A, or it may be laterally offset from the midline of the tissue penetrator (where the midline extends in a proximal to distal direction).

Figure 49A:
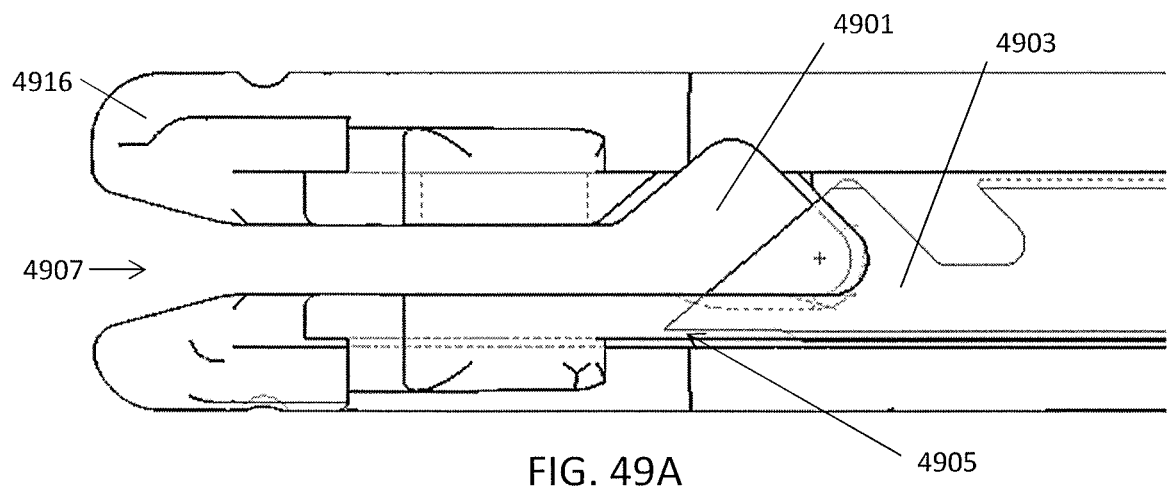
FIG. 49A shows a top view of a lower jaw member having a tissue penetrator with a laterally positioned sharp tip (relative to the width of the tissue penetrator).

In some variations, it may be desirable to have the sharp distal tip region laterally offset from the midline of the width, as illustrated in FIG. 49A. In particular, in variations in which the jaw member in which the tissue penetrator is housed include a longitudinal suture loading channel (as shown and described in FIGS. 18A-18E, above). However, a needle having a centered sharp distal tip may snag or catch on the suture when loading the suture into the central channel. For this reason, a laterally offset sharp distal tip (as shown in FIG. 18A and 37A-37B) may be used. An asymmetric needle tip offers advantages for loading suture when there is a central suture loading channel in the lower jaw, because having the needle tip off to one side of the loading groove may ensure that the sharp tip of the needle is not exposed to the suture, mitigating the chances that the suture will snag on the needle tip, as shown in FIG. 49A. The central suture-loading channel 4907 in the jaw 4916 is continuous with a suture holding region 4901 and the entire channel (and thus any suture held within the channel) is protected from the sharp distal tip 4905, as the sharp distal tip 4905 of the tissue penetrator 4903 is laterally displaced and is held within the jaw 4916.

Figure 49B:
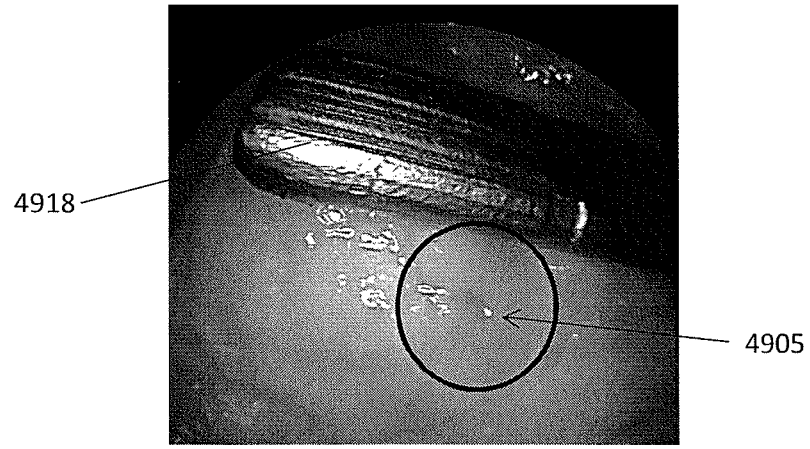
FIG. 49B shows an example of a needle tip that is miss-directed lateral to the upper jaw when extending through the tissue because of the normal force exerted against the angled, asymmetric tip as it passes through the tissue.

Unfortunately, asymmetric needle tips may have a tendency to drift laterally (e.g., toward the side of the needle tip) when passing through tissue, because the force of driving the needle through the tissue results in a normal force on the angled needle edge. With enough needle drift, the needle can miss the suture retention feature in the opposite jaw, as shown in FIG. 49B. In FIG. 49B, the tissue penetrator has a sharp distal tip that is laterally offset from the midline of the width, similar to the needle 4903 shown in FIG. 49A. The tip of the needle 4905 has drifted (been driven) lateral to the opposite jaw 4918.

Figure 49C:
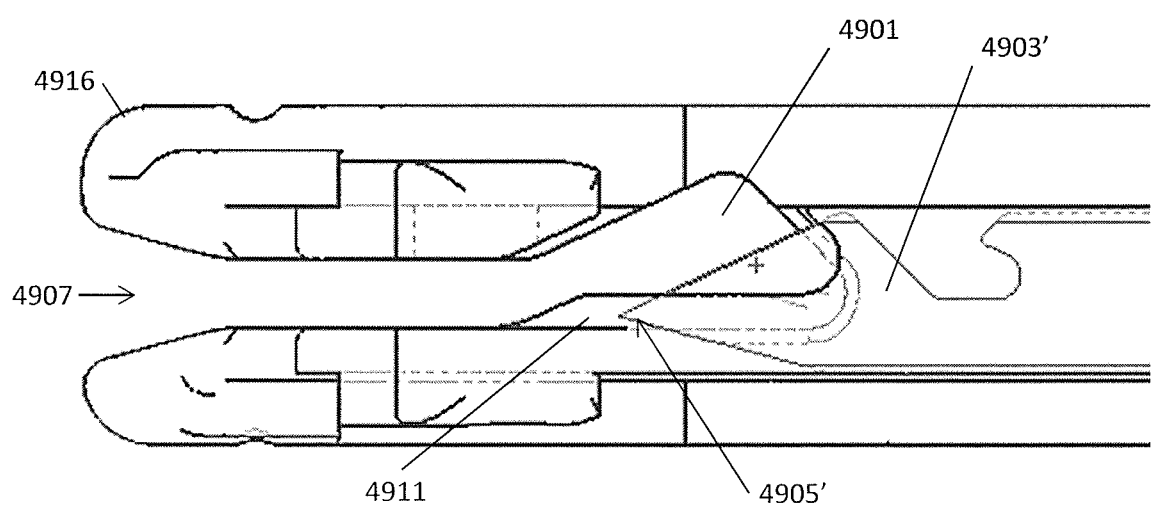
FIG. 49C shows an example of a lower jaw including a tissue penetrator having a distal tip region that is less than 40% off-center. The lower jaw member includes a tip shield region in the central suture loading channel to prevent a suture from snagging on the sharp distal tip when loading/unloading into the tissue penetrator.

In general, tissue penetrators having less asymmetrically located sharp distal tips (e.g., less laterally offset from the midline) may have less of a tendency to deviate laterally when extending through the tissue, and may therefore have a higher reliability when contacting the suture retention feature in the opposite jaw. However, to ensure that suture can enter the loading area of the suture passer without snagging on the needle tip, the shape of loading channel may be modified to cover the needle tip. For example, FIG. 49C illustrates one variation of a jaw having a central suture loading channel 4907 to load a suture into a tissue penetrator. The jaw includes a ramped cover 4911 housing the centrally (or slightly offset from the midline, e.g., less than 30% offset, less than 25% offset, less than 20% offset, less than 15% offset, etc. from the midline) located sharp distal tip 4905' of the tissue penetrator 4903'. Thus, a suture may be protected from snagging on the tissue penetrator tip when being loaded in the central channel 4907.

Any of the tissue penetrators described herein may also be adapted to prevent snagging of tissue (e.g., capsule or meniscal tissue) when extending through the tissue.

FIG. 50A illustrates one variation of a tissue penetrator (needle) having a side-opening suture retainer region 5005. The distal edge 5003 of the side opening 5005 extends the full lateral width of the tissue penetrator, w, as shown in FIG. 50A, as does the proximal edge 5002 of the side opening 5005 of the suture retainer region 5001.

When a surgeon is passing a suture through meniscus using a suture passer, the surgeon may wish to pass suture through the adjoining capsular tissue as well. The capsular tissue behaves much differently than meniscal tissue, and may have a high propensity for snagging on needle features rather than being punctured by the needle tip. Consequently, needle tip sharpness may be important; unfortunately, even if the tip of the needle is sharp other portions of the needle, and particularly the side opening suture retaining region may get caught on capsular tissue, impeding the forward motion of the tissue penetrator. FIG. 50B illustrates one example of a needle such as the needle shown in FIG. 50A extending though a meniscus and capsule; the capsule tends to collapse around the needle as the needle is extended distally, driving the capsule tissue into the suture retainer region and hooking it on the proximal side of the suture retainer region. This can potentially deflect the tissue penetrator or prevent it from advancing further distally.

To ensure that a needle can easily pass through the tissue, a needle may be adapted to prevent snagging by providing angled surfaces, so that any tissue being directed medially inwardly (e.g., into the suture retaining region) is directed laterally out of the suture retainer region.

For example, FIG. 50C show one variation of a tissue penetrator that has the proximal edge of the side opening for the suture retainer region forms a ramping region 5007 (e.g., an angle relative to the proximal long side of the needle) that is between about 100 degrees and 170 degrees (e.g., in FIG. 50C, the angle, α, is approximately 135 degrees, as shown in FIG. 50D) and has a ramp length that is sufficiently long to allow tissue to contract around the needle slightly but still land on the ramp region and be guided out of the suture retainer region. The ramp length may be between about 5% and about 50% (e.g., between 10% and 40%, between about 10% and 35%, etc.) of the width of the needle, w. In FIG. 5C, the length of the ramp 5007 is approximately 20% the width of the needle. In FIG. 50C, the proximal edge of the opening for the suture retainer region has a ramp shape near the proximal edge that moves the tallest point of the suture retention feature on the needle closer to the midline of the needle and away from the side. By moving this feature inward (forming the ramp region), there is less chance that tissue can snag on this location.

Any of the suture passers described herein could be used for repair of soft tissue in joints, to sew in allografts or artificial soft tissue constructs such as an artificial meniscal scaffold or graft, and/or for meniscus repair.

Although many of the variations of suture passer devices described herein are configured so that the tissue penetrator extends distally from an opening in a jaw, any of the suture passers described herein may be configured so that the tissue penetrator extends proximally after extending between the upper and lower jaws. Thus, the deflection features on the upper jaw could be set to facilitate the needle heading in the proximal direction. For example, in some variations the tissue penetrator extends proximally within (or out of) the upper jaw member after extending across the opening between the jaws.

Although the description above is broken into parts and includes specific examples of variations of suture passers, any of the features or elements described in any particular example or section may be incorporated into any of the other embodiments. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A suture passer system with a preloaded suture, the system comprising:
   an elongate body extending distally and proximally;
   a first jaw coupled to a distal end of the elongate body; and
   a second jaw removably coupled to the elongate body, wherein the second jaw comprises:
   a tissue penetrator configured to slide distally and proximally within the second jaw;
   a suture within the second jaw, the suture comprising a first bight region loaded in a suture engagement region at a distal end region of the tissue penetrator, and a second bight region loaded in a suture holding region within the second jaw; and a releasable hold on the tissue penetrator configured to cooperate with the suture holding region to adjust tension on a first end portion of the suture such that when the tissue penetrator is advanced distally, tension is reduced and when the tissue penetrator is withdrawn proximally tension is increased so that the second bight region is drawn into the suture engagement region after the first bight region has been removed.

2. The suture passer system of claim 1, wherein the second jaw includes an engagement region that is configured to releasably engage with a complimentary engagement region of the elongate body.

3. The suture passer system of claim 1, wherein the second jaw is configured to retain the suture in a preloaded configuration such that the first bight is loaded in the suture engagement region of the tissue penetrator when the second jaw is uncoupled from the elongate body.

4. The suture passer system of claim 3, wherein in the preloaded configuration, the second bight region is loaded in the suture holding region.

5. The suture passer system of claim 1, wherein the suture passer system further comprises a handle, wherein the second jaw is configured to releasably couple with the elongate body such that distal and proximal sliding of the tissue penetrator within the second jaw is controllable via a control of the handle.

6. The suture passer system of claim 1, wherein the releasable hold comprises a sled operatively coupled to the tissue penetrator and a handle of the suture passer, to facilitate the distal and proximal sliding of the tissue penetrator and releasably hold the first end portion of the suture.

7. A method of operating a suture passer that is preloaded with a suture, the method comprising:
coupling a jaw cartridge to an elongate body of the suture passer, wherein the suture passer includes a first jaw pivotally coupled to a distal end region of the elongate body, further wherein the jaw cartridge comprises a second jaw, a first bight of the suture, a second bight of suture, a tissue penetrator and a releasable hold configured to adjust tension on the second bight of suture;
forming a distal-facing opening between the first jaw and the second jaw by sliding the second jaw distally relative to the elongate body;
extending a distal tip of a tissue penetrator from within the second jaw and across the distal-facing opening, wherein the tissue penetrator comprises a suture engagement region that is preloaded with the first bight region of the suture, wherein while extending the tissue penetrator, tension on the second bight of suture is reduced;
holding the first bight region with the first jaw and retracting the distal tip of the tissue penetrator into the second jaw;
withdrawing the tissue penetrator within the second jaw to increase tension to the first length of suture, so that the second bight region is drawn into the suture engagement region of the tissue penetrator; and
extending the distal tip of the tissue penetrator from the second jaw and across the distal-facing opening, wherein the tissue penetrator is carrying the second bight region of the suture.

8. The method of claim 7, wherein coupling the jaw cartridge comprises engaging a housing engagement region on the jaw cartridge to the elongate body of the suture passer to slideably couple the cartridge to the elongate body.

9. The method of claim 7, wherein the jaw cartridge comprises the suture in a preloaded configuration prior to coupling the jaw cartridge to the elongate body.

10. The method of claim 9, wherein in the preloaded configuration, the second bight region of the suture is loaded in a suture holding region of the jaw cartridge.

11. The method of claim 7, wherein coupling the jaw cartridge comprises engaging an engagement region of the jaw cartridge with a complimentary engagement region of the elongate body.

12. The method of claim 7, further comprising uncoupling the jaw cartridge from the elongate body.

13. The method of claim 7 wherein coupling comprises aligning a keyed region of the cartridge with a keyed region of the elongate body, following by sliding the cartridge proximally wherein the entire jaw cartridge is proximally disposed relative to the upper jaw.

14. A method of operating a suture passer, the method comprising:
inserting a keyed region of a replaceable jaw cartridge with an engagement region of an elongate body of the suture passer and sliding the replaceable jaw cartridge proximally, so as to secure the replaceable jaw cartridge with the elongate body, wherein the elongate body includes a first jaw pivotally coupled to a distal end region of the elongate body and the step of sliding positions a distal-most end of the replaceable jaw cartridge proximally from the first jaw; the replaceable jaw cartridge comprising a second jaw, a first bight region of a suture, a second bight region of the suture, a tissue penetrator and a releasable hold coupled to both the tissue penetrator and to a length of the suture extending from the second bight region;
forming a distal-facing opening between the first jaw and the second jaw by sliding the second jaw distally relative to the elongate body;
extending the tissue penetrator and the first bight region from within the second jaw across the distal-facing opening, wherein while extending the tissue penetrator, the releasable hold cooperates with the tissue penetrator to reduce tension on the second bight region;
holding the first bight region with the first jaw and retracting the distal tip of the tissue penetrator into the second jaw;
withdrawing the tissue penetrator within the second jaw to increase tension on the second bight region, so that the second bight region is drawn into a suture engagement region of the tissue penetrator; and
extending the tissue penetrator from the second jaw and across the distal-facing opening, wherein the tissue penetrator is carrying the second bight region of the suture.

15. The method of operating the suture passer of claims 7 or 14 wherein the releasable hold comprises a sled configured to couple with the tissue penetrator to drive advancement and retraction of the tissue penetrator and to releasably hold the length of suture on the tissue penetrator.

\* \* \* \* \*